United States Patent [19]

Thompson

[11] Patent Number: 4,643,759
[45] Date of Patent: Feb. 17, 1987

[54] HERBICIDAL SULFONAMIDES

[75] Inventor: Mark E. Thompson, Wilmington, Del.

[73] Assignee: E. I. Du Pont de Nemours and Company, Wilmington, Del.

[21] Appl. No.: 743,303

[22] Filed: Jun. 13, 1985

Related U.S. Application Data

[63] Continuation-in-part of Ser. No. 630,895, Jul. 13, 1984, abandoned.

[51] Int. Cl.$^4$ .................. A01N 47/36; C07D 403/12; C07D 413/12; C07D 417/12
[52] U.S. Cl. .......................................... 71/90; 71/92; 71/93; 544/209; 544/212; 544/253; 544/278; 544/321; 544/331
[58] Field of Search ...................... 71/90, 92; 544/321, 544/331, 278, 253

[56] References Cited

FOREIGN PATENT DOCUMENTS 99339 1/1984 European Pat. Off. ................ 71/90

Primary Examiner—Robert Gerstl

[57] ABSTRACT

This invention relates to certain herbicidally active sulfonamide compounds, suitable agricultural compositions thereof and a method for their use as general and-/or selective preemergence or postemergence herbicides or plant growth regulants.

31 Claims, No Drawings

HERBICIDAL SULFONAMIDES

RELATED APPLICATION

This application is a continuation-in-part of copending application U.S. Ser. No. 630,895, filed July 13, 1984, now abandoned.

BACKGROUND OF THE INVENTION

This invention relates to herbicidally active sulfonamide compounds, suitable agricultural compositions thereof and a method for their use as a pre- or postemergence herbicide and/or plant growth regulant.

New componds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

A number of different types of N-[(heterocyclic-)aminocarbonyl]aryl- and heteroarylsulfonamides are known as herbicides.

U.S. Pat. No. 4,391,627 discloses herbicidal sulfonamides of formula

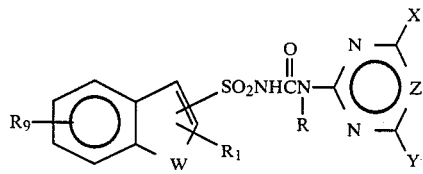

where W is O or S.

European Patent Application (EP-A) No. 70,698, published Jan. 26, 1983, describes herbicidal sulfonamides of formula

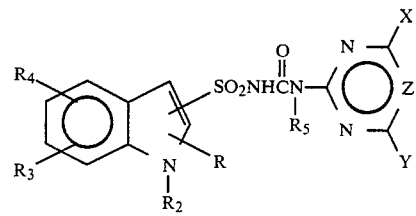

where $R_2$ is H, $C_1$–$C_3$ alkyl or $SO_2C_6H_5$.

EP-A No. 79,683, published May 25, 1983, discloses herbicidal sulfonamides of formula

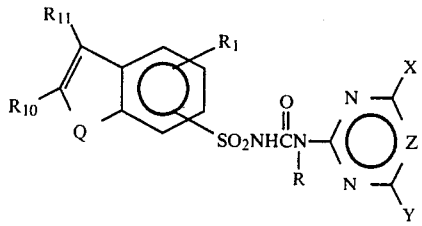

where Q is O, S or $SO_2$.

The current population explosion and concomitant world food and fiber shortage demand improvement in the efficiency of producing these crops. Preventing or minimizing loss of valuable crops by killing or inhibiting the growth of undesired vegetation is one way of improving this efficiency. Even though there are a wide variety of products useful for killing and inhibiting growth of undesired vegetation the need still exists for more effective herbicides.

SUMMARY OF THE INVENTION

This invention relates to novel compounds of Formula I, suitable agricultural compositions containing them and their method of use as general and/or selective preemergence and/or postemergence herbicides and/or plant growth regulants. In accordance with the invention the compounds of Formula I are

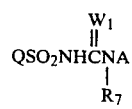

wherein
Q is

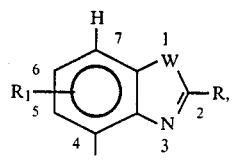   Q-1

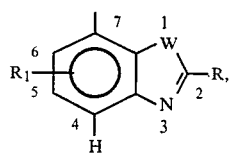   Q-2

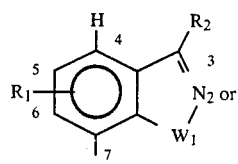   Q-3

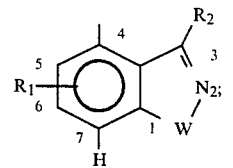   Q-4

$W_1$ is O or S;
$R_7$ is H or $CH_3$;

R is H, $C_1$–$C_4$ alkyl optionally substituted with 0–3 halogen atoms selected from 1–3 F, 1–2 Cl or 1 Br, $C_1$–$C_4$ alkylthio, $C_1$–$C_4$ alkoxy, $CH_2OCH_3$, $CH_2CH_2OCH_3$ or $CH_2SCH_3$;

$R_1$ is H, halogen, $C_1$–$C_4$ alkyl, $C_1$–$C_3$ haloalkyl, nitro, $C_1$–$C_3$ alkoxy, di($C_1$–$C_2$)alkylaminosulfamoyl, $C_1$–$C_3$ alkylthio, $C_1$–$C_3$ haloalkoxy, $C_1$–$C_3$ haloalkylthio, cyano, $C_1$–$C_3$ alkylsulfinyl, $C_1$–$C_3$ alkylsulfonyl, $C_2$–$C_3$ alkoxycarbonyl, $CH_2OCH_3$, $CH_2SCH_3$ or $CH_2CN$;

$R_2$ is H or $CH_3$;

W is O, S or $NR_3$;

$R_3$ is H or $CH_3$;

A is

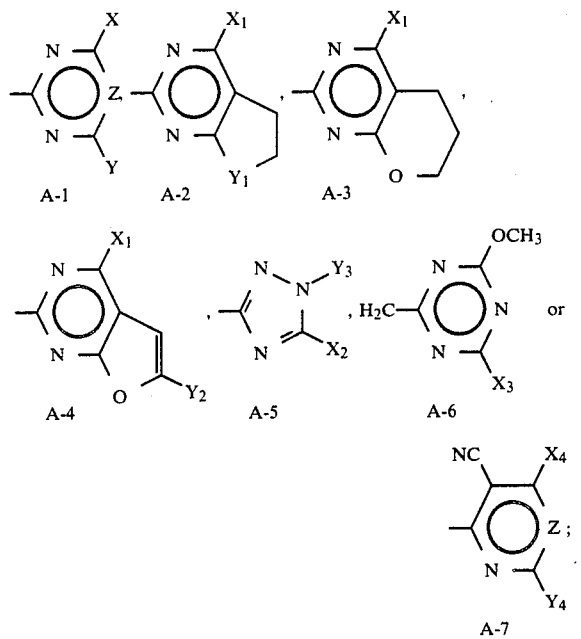

X is H, $C_1$–$C_3$ alkyl, $C_1$–$C_3$ alkoxy, $C_1$–$C_3$ haloalkoxy, $C_1$–$C_3$ haloalkyl, $C_1$–$C_3$ haloalkylthio, $C_1$–$C_3$ alkylthio, halogen, $C_2$–$C_3$ alkoxyalkyl, $C_2$–$C_3$ alkoxyalkoxy, amino, $C_1$–$C_3$ alkylamino or di($C_1$–$C_3$)alkylamino;

Y is H, $C_1$–$C_3$ alkyl, $C_1$–$C_3$ alkoxy, $C_1$–$C_3$ haloalkoxy, $C_1$–$C_3$ haloalkylthio, $C_1$–$C_3$ alkylthio, halogen, $C_2$–$C_3$ alkoxyalkyl, $C_2$–$C_3$ alkoxyalkoxy, amino, $C_1$–$C_3$ alkylamino, di($C_1$–$C_3$)alkylamino, $C_3$ alkenyloxy, $C_3$ alkynyloxy, $C_2$–$C_3$ alkynyl, $C_2$–$C_3$ alkylthioalkyl, $C_2$–$C_3$ alkylsulfinylalkyl, $C_2$–$C_3$ alkylsulfonylalkyl, $C_1$–$C_3$ haloalkyl, cyclopropyl, $C(O)R_4$,

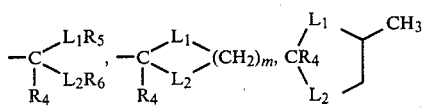

m is 2 or 3;

$L_1$ and $L_2$ are independently O or S;

$R_4$ is H or $CH_3$;

$R_5$ and $R_6$ are independently $C_1$–$C_2$ alkyl;

Z is CH or N;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$;

$Y_3$ is $CH_3$, $C_2H_5$ or $CH_2CF_3$;

$X_3$ is $CH_3$ or $OCH_3$;

$X_4$ is $CH_3$, $OCH_3$, $OC_2H_5$, $CH_2OCH_3$ or Cl; and $Y_4$ is $CH_3$, $OCH_3$, $OC_2H_5$ or Cl;

and their agriculturally suitable salts; provided that (a) when $W_1$ is S, then $R_7$ is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

(b) when X or Y is $OCF_2H$, then Z is CH;

(c) when X is F, Cl, Br or I, then Z is CH and Y is $OCH_3$, $OC_2H_5$, $OCF_2H$, $NH_2$, $NHCH_3$, $N(OCH_3)CH_3$ or $N(CH_3)_2$;

(d) when $R_1$ is di($C_1$–$C_2$)alkylaminosulfamoyl or $C_2$–$C_3$ alkoxycarbonyl, then Q is Q-1 and $R_1$ is in the 5-position; or Q is Q-2 and $R_1$ is in the 6-position; and (e) when the total number of carbon atoms of X and Y is greater than four, then the number of carbon atoms of R is less than or equal to two, and the number of carbon atoms of $R_1$ is less than or equal to two.

In the above definitions, the term "alkyl", used either alone or in compound words such as "alkylthio" or "haloalkyl", denotes straight chain or branched alkyl, e.g. methyl, ethyl, n-propyl or isopropyl.

Alkoxy denotes methoxy, ethoxy, n-propoxy or isopropoxy.

Alkenyl denotes straight chain or branched alkenes, e.g. 1-propenyl, 2-propenyl or 3-propenyl.

Alkynyl denotes 1-propynyl or 2-propynyl.

The term "halogen", either alone or in compound words such as "haloalkyl", denotes fluorine, chlorine, bromine or iodine.

Alkoxycarbonyl denotes methoxycarbonyl or ethoxycarbonyl.

Alkylsulfonyl denotes methylsulfonyl, ethylsulfonyl and the different propylsulfonyl isomers.

Alkylthio, alkylsulfinyl, alkylamino, etc. are defined in an analogous manner.

In terms such as $C_2$–$C_3$ alkylthioalkyl, the specified number of carbon atoms is meant to define the *total* number of carbon atoms in that substituent group. For example, $C_2$–$C_3$ alkylthioalkyl would designate $CH_2SCH_3$, $CH_2SC_2H_5$, $CH_2CH_2SCH_3$ or $CH(CH_3)SCH_3$, and $C_2$–$C_5$ alkoxyalkoxy would represent $OCH_2OCH_3$ through $O(CH_2)_4OCH_3$ or $OCH_2O(CH_2)_3CH_3$ and the various structural isomers embraced therein.

The preferred compounds for reasons of greater herbicidal efficacy and/or increased ease of synthesis are:

(1) Compounds of Formula I where $W_1$ is O, $R_7$ is H, X is $CH_3$, $OCH_3$, $OC_2H_5$, halogen, $OCF_2H$, $CH_2F$, $OCH_2CH_2F$, $OCH_2CHF_2$, $OCH_2CF_3$ or $CF_3$, and Y is H, $CH_3$, $OCH_3$, $OC_2H_5$, $CH_2OCH_3$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $C\equiv CH$, $C\equiv CCH_3$, $CH_2OC_2H_5$, $OCH_2CH_2OCH_3$, $CH_2SCH_3$,

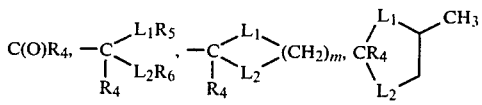

OCF$_2$H, SCF$_2$H or cyclopropyl;

(2) Compounds of Preferred 1 where R$_1$ is H, F, Cl, Br, CH$_3$, OCH$_3$, OCF$_2$H, CF$_3$, CH$_2$OCH$_3$ or CH$_2$SCH$_3$, R is H or C$_1$–C$_2$ alkyl, and Q is Q-1 or Q-2;

(3) Compounds of Preferred 2 where A is A-1, X is CH$_3$, OCH$_3$, Cl, Br or OCF$_2$H, and Y is CH$_3$, OCH$_3$, CH$_2$OCH$_3$, NHCH$_3$, C$_2$H$_5$, CH(OCH$_3$)$_2$, cyclopropyl, C≡CH or C≡CCH$_3$;

(4) Compounds of Preferred 3 where Q is Q-1 and R$_1$ is H;

(5) Compounds of Preferred 3 where Q is Q-2 and R$_1$ is H;

(6) Compounds of Preferred 4 where W is O;
(7) Compounds of Preferred 4 where W is S;
(8) Compounds of Preferred 4 where W is NR$_3$;
(9) Compounds of Preferred 5 where W is O;
(10) Compounds of Preferred 5 where W is S;
(11) Compounds of Preferred 5 where W is NR$_3$;

(12) Compounds of Preferred 1 where A is A-1, R$_1$ is H, F, Cl, Br, CH$_3$, OCH$_3$, OCF$_2$H, CF$_3$, CH$_2$OCH$_3$ or CH$_2$SCH$_3$, R is H or C$_1$–C$_2$ alkyl, X is CH$_3$, OCH$_3$, Cl, Br or OCF$_2$H, Y is CH$_3$, OCH$_3$, CH$_2$OCH$_3$, NHCH$_3$, C$_2$H$_5$, CH(OCH$_3$)$_2$, cyclopropyl, C≡CH or C≡CCH$_3$, and Q is Q-3 or Q-4;

(13) Compounds of Preferred 12 where Q is Q-3 and R$_1$ is H;
(14) Compounds of Preferred 12 where Q is Q-4 and R$_1$ is H;
(15) Compounds of Preferred 13 where W is O;
(16) Compounds of Preferred 13 where W is S;
(17) Compounds of Preferred 13 where W is NR$_3$;
(18) Compounds of Preferred 14 where W is O;
(19) Compounds of Preferred 14 where W is S;
(20) Compounds of Preferred 14 where W is NR$_3$.

Compounds of the invention specifically preferred for reasons of higher herbicidal efficacy and/or greater ease of synthesis are:

N-[(4,6-dimethoxypyrimidin-2-yl)aminocarbonyl]-2-methylbenzothiazole-4-sulfonamide, m.p. 187°–194° C.; and N-[(4-methoxy-6-methyltriazin-2-yl)aminocarbonyl]-2-methylbenzothiazole-4-sulfonamide, m.p. 182.5°–183° C.

Another embodiment of the present invention includes compounds of Formula I as defined above except wherein W$_1$ is O;
R$_7$ is H;
R is H or C$_1$–C$_5$ alkyl;
R$_1$ is H, F, Cl, Br, CH$_3$, OCH$_3$ or OCF$_2$H;
A is

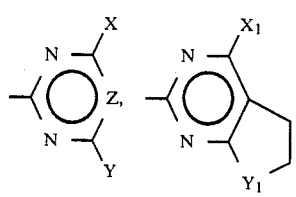

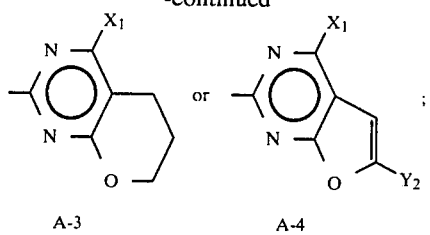

X is CH$_3$, OCH$_3$, OCH$_2$CH$_3$, Cl, F, Br, I, OCF$_2$H, CH$_2$F, OCH$_2$CH$_2$F, OCH$_2$CHF$_2$, OCH$_2$CF$_3$ or CF$_3$; and Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, OCH$_2$CH$_2$OCH$_3$,

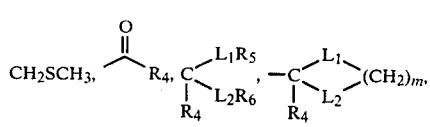

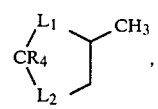

OCF$_2$H, SCF$_2$H or cyclopropyl;
provided that when X is Cl, F, Br or I, then Z is CH and Y is OCH$_3$, OC$_2$H$_5$, N(OCH$_3$)CH$_3$, NHCH$_3$, N(CH$_3$)$_2$ or OCF$_2$H; and their agriculturally suitable salts.

The compounds of this embodiment that are preferred for reasons of greater herbicidal efficacy and/or increased ease of synthesis are:

(1) Compounds of Formula I where Q is Q-1 and W is O or S;

(2) Compounds of Preferred 1 where A is A-1, R is H or CH$_3$ and R$_1$ is H, Cl, CH$_3$ or OCH$_3$;

(3) Compounds of Preferred 2 where Y is CH$_3$, OCH$_3$, CH$_2$OCH$_3$, NHCH$_3$, CH$_2$CH$_3$, CH(OCH$_3$)$_2$ or cyclopropyl;

(4) Compounds of Preferred 3 where X is CH$_3$, OCH$_3$, Cl, Br or OCF$_2$H.

The compounds of the invention that are most preferred for reasons of higher herbicidal efficacy and/or greater ease of synthesis are N-[(4,6-dimethoxypyrimidin-2-yl)aminocarbonyl]-2-methyl-4-benzothiazolesulfonamide; and N-[(4-methoxy-6-methyl-triazin-2-yl)-aminocarbonyl]-2-methyl-4-benzothiazolesulfonamide.

DETAILED DESCRIPTION OF THE INVENTION

Synthesis

The compounds of Formula I can be prepared by one or more of the procedures shown below in Equations 1, 2, and 3.

Equation 1 depicts the reaction of sulfonyl isocyanates of Formula II with the appropriate heterocyclic amines III to give the desired products of Formula I.

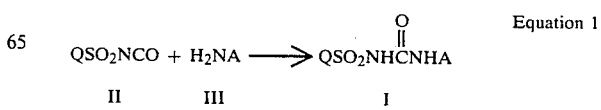

wherein

Q and A are as previously defined.

The reaction of Equation 1 is best carried out in an inert aprotic solvent such as methylene chloride, tetrahydrofuran, or acetonitrile at a temperature between 20° and 80° C. A catalytic amount of 1,4-diazabicyclo[2.2.2]octane (DABCO) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, diethyl ether, or methanol, and filtration.

Compounds of Formula I can also be prepared as shown in Equation 2 by treating sulfonamides of Formula IV with the methyl ester of a pyrimidine or triazine carbamic acid of Formula V in the presence of an equimolar quantity of trimethylaluminum.

Equation 2

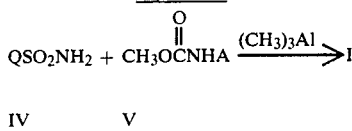

IV    V wherein

Q and A are as previously defined.

The reaction of Equation 2 is best carried out at temperatures between 25° and 83° C. in a solvent such as methylene chloride or 1,2-dichloroethane for 12 to 96 hours under an inert atmosphere. After being allowed to cool to room temperature, the reaction mixture is acidified and the desired products are isolated by either filtration or extraction with a solvent such as methylene chloride or ethyl acetate. The methyl carbamates, V, can be conveniently synthesized by treatment of the corresponding heterocyclic amines of Formula III with dimethyl carbonate or methyl chloroformate in the presence of a base such as sodium hydride or pyridine.

Alternatively, compounds of Formula I may be synthesized as shown in Equation 3 by the reaction of sulfonamides of Formula IV with the phenyl ester of an appropriate carbamic acid, VI.

Equation 3

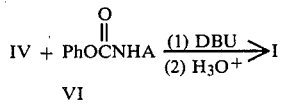

VI wherein

Q and A are as previously defined.

The reaction shown in Equation 3 is best carried out at 25° C. in a solvent such as dioxane or acetonitrile in the presence of an equimolar quantity of a tertiary amine base such as 1,5-diazabicyclo[5.4.0]undec-5-ene (DBU). After being stirred at room temperature for one to three hours, the reaction mixture is acidified and the desired product isolated either by filtration or extraction with a solvent such as ethyl acetate or methylene chloride. The phenyl carbamates, VI, can be synthesized by treating the corresponding heterocyclic amines of Formula III with diphenyl carbonate or phenyl chloroformate in the presence of a base such as sodium hydride, pyridine, or potassium carbonate in tetrahydrofuran solution.

Sulfonyl isocyanates of Formula II can be prepared as shown in Equation 4 by the reaction of sulfonamides of general structure IV with phosgene in the presence of n-butyl isocyanate and a catalytic amount of 1,4-diazabicyclo[2.2.2]octane (DABCO).

Equation 4

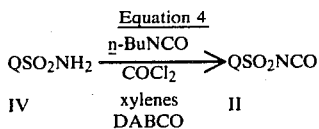

IV    xylenes    II
        DABCO wherein

Q is as previously defined.

The reaction shown in Equation 4 is best carried out according to the method taught in U.S. Pat. No. 4,238,621.

The requisite sulfonamides of Formula IV can be synthesized from the corresponding sulfonyl chlorides of Formula VII as outlined below in Equation 5.

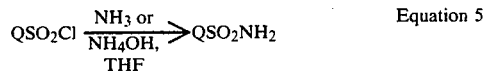

Equation 5

VII        IV wherein

Q is as previously defined.

The reaction shown in Equation 5 is most conveniently carried out by adding either excess anhydrous ammonia or concentrated ammonium hydroxide to a solution of the sulfonyl chloride, VII, in a suitable solvent such as tetrahydrofuran or diethyl ether at −30° C. to 0° C. The desired sulfonamide of Formula IV is isolated by removal of the solvent in vacuo and either crystallization from a solvent such as 1-chlorobutane or ethyl acetate, or extraction with methylene chloride or ethyl acetate; residual ammonium chloride can be removed by washing with water.

Sulfonyl chlorides of Formula VII can be prepared by one or more of the methods shown below in Equations 6, 7, 8, or 9.

Equation 6 depicts the oxidative chlorination of alkyl thioethers of Formula VIII, where W is O or $NR_3$, to give sulfonyl chlorides VIIa.

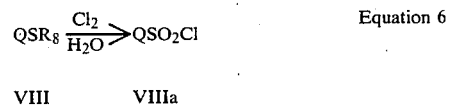

Equation 6

VIII    VIIIa wherein $R_8$ is $C_2$-$C_4$ alkyl or benzyl, Q is Q-1, Q-2, Q-3, or Q-4, and W is O or $NR_3$.

The reaction shown in Equation 6 is best effected in a suitable solvent such as chloroform or methylene chloride; in some cases, it is advantageous to use acetic acid as solvent. The reaction is carried out in the presence of at least 2.5 equivalents of water and three equivalents of chlorine gas at temperatures between 0° and 30° C. for one to five hours. The products are most conveniently isolated by removal of the solvent in vacuo and are normally carried on to the next step without purification.

Another method for the preparation of sulfonyl chlorides, VIIb, is outlined in Equation 7 and involves the reaction of unsubstituted compounds of Formula IX with chlorosulfonic acid.

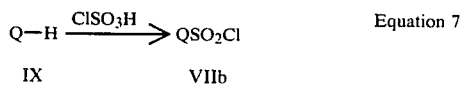

Equation 7 wherein
Q is Q-1, Q-2, Q-3, or Q-4, and W is S or $NR_3$.

The reaction of Equation 7 is best carried out by addition of the compounds IX to excess chlorosulfonic acid. The reaction mixture is then typically heated to 100°–150° C. for one to five hours, cooled to 25° C., and cautiously poured onto crushed ice. The desired sulfonyl chlorides, VIIb, are isolated by extraction with a suitable solvent such as ether, methylene chloride, or benzene, and can be carried on to the next step without purification. In cases where the sulfonyl chlorides VIIb are obtained as crystalline solids, it is often possible to remove impurities and undesired isomers by recrystallization from a solvent such as petroleum ether or hexane.

A third procedure for the synthesis of sulfonyl chlorides of Formula VIIc involves the diazotization of aniline derivatives, X, and coupling with sulfur dioxide in the presence of cupric chloride as shown in Equation 8.

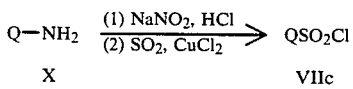

wherein
Q is Q-1, Q-2, Q-3, or Q-4, and W is S or $NR_3$.

The reaction shown in Equation 8 is accomplished by treating a solution of the aniline X in concentrated hydrochloric acid with an aqueous solution of sodium nitrite at −5° to 5° C. After being stirred for 10–30 minutes at about 0° C. to ensure complete diazotization, the solution is added to a mixture of excess sulfur dioxide and a catalytic amount of cuprous or cupric chloride in glacial acetic acid at about 10° C. The temperature is maintained at about 10° C. for 0.25–1 hour, and is allowed to rise to 25° C. where stirring is continued for 2 to 24 hours. This solution is then poured into a large excess of ice-water. The sulfonyl chlorides VIIc can be isolated by filtraton or by extraction with a solvent such as diethyl ether, methylene chloride, or 1-chlorobutane.

Alternatively, sulfonyl chlorides of Formula VIId can be prepared as shown below in Equation 9 by treatment of aryl bromides, XI, with an organometallic reagent followed by reaction with sulfuryl chloride.

Equation 9

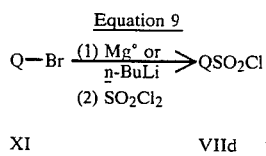

wherein
Q is Q-1 or Q-2, R is $C_2$–$C_5$ alkyl, and
$R_1$ is H, F, Cl, $CH_3$, or $OCH_3$.

The reaction of Equation 9 is most conveniently carried out according to the procedure of S. N. Bhattacharya, et al., J. Chem. Soc. (C), 1265 (1968). Thus, a solution of the aryl bromide, XI, in a solvent such as diethyl ether or tetrahydrofuran is cooled to −78° C. under an inert atmosphere and treated with a slight excess of an organometallic reagent such as n-butyllithium or phenyllithium (magnesium can also be employed to generate the Grignard reagent). The mixture is stirred at temperatures between −78° and 0° C. for 30 minutes to one hour and is then quenched with excess sulfuryl chloride. After being stirred at room temperature for one to three hours, the reaction mixture is poured onto ice and the desired sufonyl chlorides, VIId, are isolated by extraction with a suitable solvent such as methylene chloride or diethyl ether. Alternatively, the reaction mixture can simply be concentrated in vacuo to give the products VIId in a state sufficiently pure to be carried directly on to the next step.

The requisite aniline derivatives of Formula X can be prepared in a straightforward manner by reduction of the corresponding nitro compounds of Formula XII as shown in Equation 10.

Equation 10

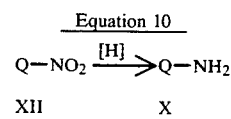

wherein
Q is Q-1, Q-2, Q-3, or Q-4, and W is S or $NR_3$.

There exists a wide variety of methods for effecting the reduction of aromatic nitro derivatives to the corresponding anilines. One of the more common procedures involves treating the nitro compounds of Formula XII with a slight excess of stannous chloride dihydrate in concentrated hydrochloric acid or ethanol solution at temperatures between 25° and 80° C. Alternatively, reduction can be accomplished with iron powder in glacial acetic acid solution as described by Hazlet and Dornfeld, J. Am. Chem. Soc., 66, 1781 (1944). For a general review, see Groggins, "Unit Processes in Organic Synthesis", McGraw-Hill Book Co., New York, 1947, pp. 73–128.

Many of the requisite intermediates mentioned above are either known in the literature or can be synthesized by methods known to one who is skilled in the art. For example, alkyl thioethers of Formula VIIIa, where Q is Q-1, can be prepared as shown in Equation 11(a) by the reaction of an appropriately substituted aniline of Formula XIIIa with a carboxylic acid or its derivatives. Similarly, compounds of Formulas IXa, XIa, and XIIa can be synthesized by the reactions shown below in Equations 11(b), 11(c), and 11(d), respectively.

Equation 11

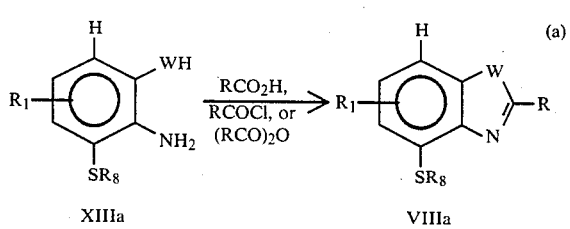

-continued
Equation 11

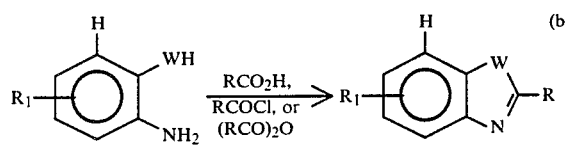
XIVa → IXa (b)

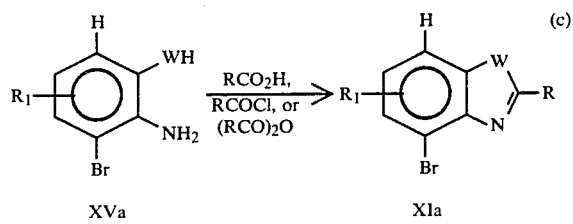
XVa → XIa (c)

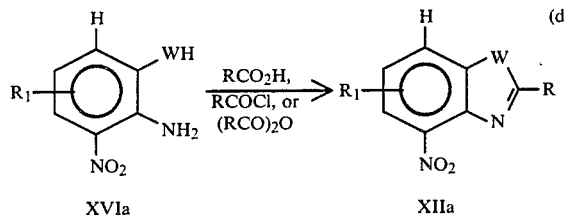
XVIa → XIIa (d)

wherein

R, $R_1$ and W are as previously defined, and $R_8$ is $C_2$–$C_4$ alkyl or benzyl.

This type of procedure can also be applied to the synthesis of alkyl thioethers of Formula VIIIb, where Q is Q-2, and to the preparation of compounds of Formulas IXb, XIb, and XIIb as shown in Equation 12 (a–d).

Equation 12

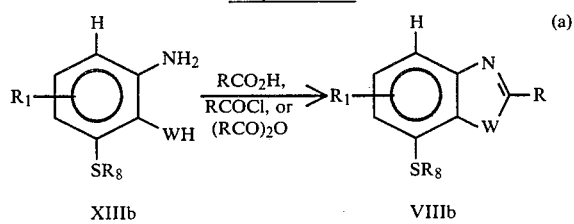
XIIIb → VIIIb (a)

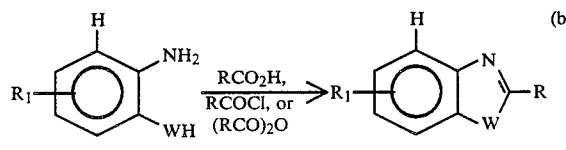
XIVb → IXb (b)

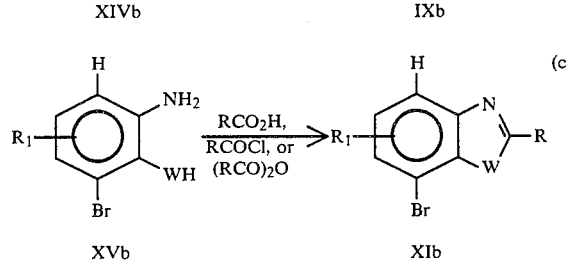
XVb → XIb (c)

-continued
Equation 12

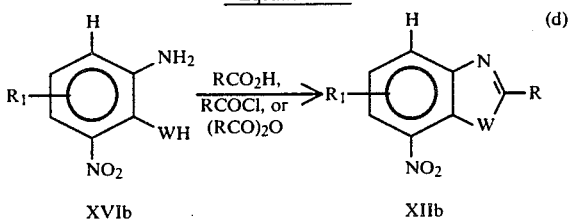
XVIb → XIIb (d)

wherein

R, $R_1$ and W are previously defined, and $R_8$ is $C_2$–$C_4$ alkyl or benzyl.

The reactions outlined above in Equations 11(a–d) and 12(a–d) have received a great deal of study and are well precedented in the literature. Benzothiazoles (Q=Q-1 or Q-2, and W=S) can be prepared according to the procedure of Hofmann, Ber., 12, 2359 (1879); 13, 8, 1223 (1880); 20, 1798 (1887). For an excellent compilation of references dealing with the synthesis of benzothiazoles, see J. M. Sprague and A. H. Land in "Heterocyclic Compounds", Vol. 5, ed. R. C. Elderfield, John Wiley and Sons, Inc., New York, 1957, pp. 506–518. Benzoxazoles (Q=Q-1 or Q-2, and W=O) can be prepared in an analogous fashion by treatment of the appropriate o-aminophenols with a carboxylic acid or its derivatives. For a general overview of the methods known for the synthesis of benzoxazoles, see J. W. Cornforth in "Heterocyclic Compounds", Vol. 5, ed. R. C. Elderfield, Wiley, New York, 1957, pp. 420–434. Finally, benzimidazoles (Q=Q-1 or Q-2, and W=$NR_3$) can be prepared by similar methods as described by E. S. Schipper and A. R. Day in "Heterocyclic Compounds", Vol. 5, ed. R. C. Elderfield, Wiley, New York, 1957, pp. 274–284.

An alternate synthesis of benzothiazoles of Formulas VIIIa, IXa, XIa, XIIa, and VIIIb, IXb, XIb and XIIb, where W is S, involves an oxidative cyclization of thioamides XVIIa and XVIIb as shown below in Equation 13(a,b).

Equation 13

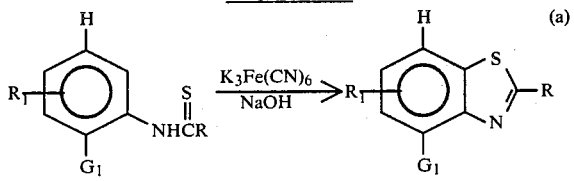
XVIIa → (a)

VIIIa ($G_1$ = $SR_8$)
IXa ($G_1$ = H)
XIa ($G_1$ = Br)
XVIa ($G_7$ = $NO_2$)

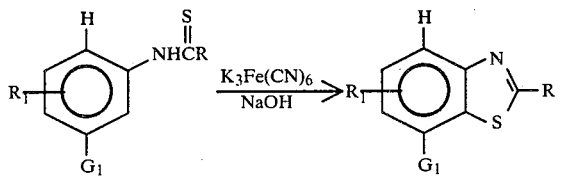
XVIIb →

VIIIb ($G_1$ = $SR_8$)
IXb ($G_1$ = H)
XIb ($G_1$ = Br)
XVIb ($G_1$ = $NO_2$)

wherein

R and $R_1$ are as previously defined, and $R_8$ is $C_2$–$C_4$ alkyl or benzyl.

The reaction of Equation 13 is best effected according to the procedure of Jacobson, *Ber.*, 19, 1067, 1811 (1886); 20, 1895 (1887); 22, 904 (1889); 26, 2363 (1893). This reaction often affords mixtures of regioisomeric benzothiazoles which can be separated by chromatography or recrystallization.

Many of the requisite indazoles of Formulas VIIIc, IXc, and XIIc, where Q is Q-3 or Q-4 and W is $NR_3$, are either known in the literature or can be synthesized by methods known to one who is skilled in the art. Equation 14(a) shows one of the more common procedures which involves cyclization of the appropriate hydrazones, XVIIIa, in the presence of a suitable base such as sodium hydroxide or potassium carbonate to give the desired products VIIIc, IXc, and XIIc. This same type of reaction can be applied to the synthesis of indazoles of Formulas VIIId, IXd, and XIId, starting from the corresponding hydrazones, XVIIIb, as shown in Equation 14(b).

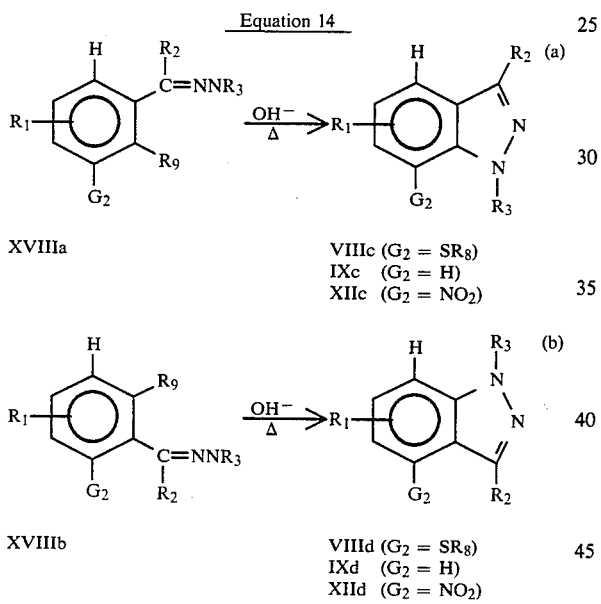

wherein $R_1$, $R_2$, and $R_3$ are as previously defined, $R_9$ is $NO_2$, Cl, or Br and $R_8$ is $C_2$–$C_4$ alkyl or benzyl.

When $R_9$ is $NO_2$, the reactions of Equations 14 (a and b) can be most conveniently carried out according to the procedure of Reich and Gaigailian, *Ber.*, 46, 2380 (1913); Meyer, *Ber.*, 22, 318 (1889); and Dittrich and Meyer, *Ann.*, 264, 131 (1891). When $R_9$ is Cl or Br, the reactions of Equation 14 (a and b) are best performed according to the procedure of Fries and Tampke, *Ann.*, 454, 270 (1927). For alternate syntheses of indazoles such as VIII(c,d), IX(c,d), and XII(c,d), refer to Elderfield in "Heterocyclic Compounds", Vol. 5, ed. R. C. Elderfield, Wiley, New York, 1957, pp. 163–182.

1,2-Benzisoxazoles of Formulas VIIIe and VIIIf, where Q is Q-3 or Q-4, and W is O, can be prepared by any one of a number of well-known methods. Equation 15(a,b) outlines the reaction of ortho-substituted benzoyl compounds, such as XXa and XXb, with hydroxylamine to give the corresponding oximes, XIXa and XIXb, which are directly treated with alkali to afford the desired products, VIIIe and VIIIf, respectively.

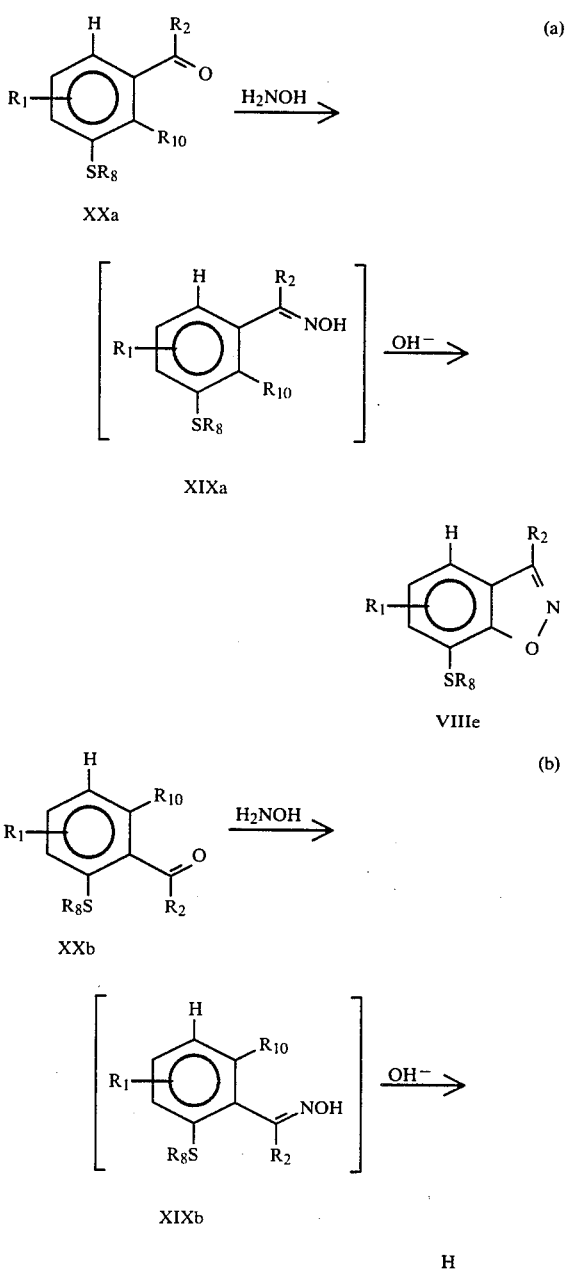

wherein $R_1$ and $R_2$ are as previously defined, $R_8$ is $C_2$–$C_4$ alkyl or benzyl, and $R_{10}$ is Br, Cl, I, F, or $NO_2$.

The reaction of Equation 15 is best accomplished by the procedure of Cathcart and Meyer, *Ber. Deut. Chem. Ges.*, 25, 1498(1892). A modification of this general type of reaction can also be applied to the synthesis of 1,2- benzisoxazoles; see Lindemann and Thiele, *Ann. Chem.*, 449, 63 (1926). For a review of alternative syntheses, refer to K. -H. Wunsch and A. J. Boulton, *Adv. Heterocyclic Chem.*, 8, 277 (1967).

1,2-Benzisothiazoles of Formulas IXe, XIIe, IXf, and XIIf, where Q is Q-3 or Q-4, and W is S, can also be prepared by one or more of several possible procedures; one such method is shown below in Equation 16(a,b). Thus, aminothiols of Formulas XXIa or XXIb are treated with an oxidizing agent such as iodine, bromine, or potassium ferricyanide to give the desired products IXe, XIIe, IXf or XIIf.

Equation 16

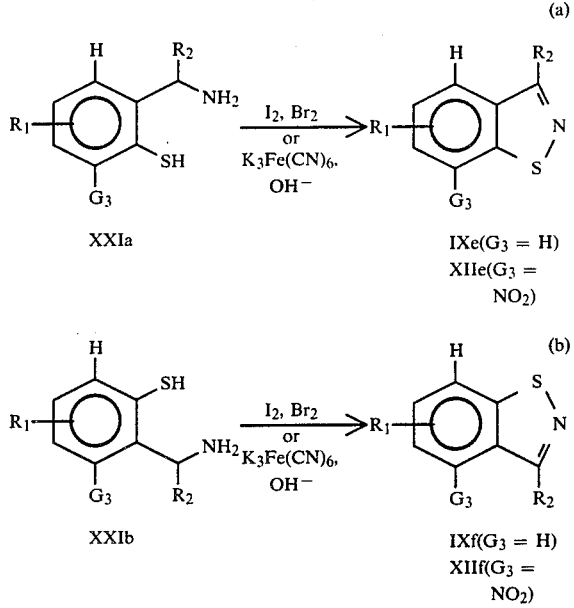

wherein
$R_1$ and $R_2$ are as previously defined.

The reaction of Equation 16 is most easily carried out according to the procedure of Goerdeler and Kandler, *Chem. Ber.*, 92, 1679 (1959). Alternate syntheses of 1,2-benzisothiazoles have been reviewed by M. Davis in *Adv. Heterocyclic Chem.*, 14, 43 (1972).

The synthesis of heterocyclic amines such as those represented by Formula III has been reviewed in "The Chemistry of Heterocyclic Compounds", a series published by Interscience Publ., New York and London. Aminopyrimidines are described by D. J. Brown in "The Pyrimidines", Vol. XVI of the series mentioned above which is herein incorporated by reference. The 2-amino-1,3,5-triazines of Formula III, where A is A-1 and Z is N, can be prepared according to methods described by E. M. Smolin and L. Rapaport in "s-Triazines and Derivatives", Vol. XIII.

Pyrimidines of Formula III, where A is A-1 and Y is an acetal or thioacetal substituent, can be prepared by methods taught in European Patent Appliction No. 84,224 (published July 27, 1983).

Pyrimidines of Formula III, where A is A-1 and Y is cyclopropyl or $OCF_2H$, can be synthesized according to the methods taught in South African Patent Application No. 837,434 and South African Publication No. 82/5045, respectively.

Compounds of Formula III, where A is A-2 or A-3, can be prepared by procedures disclosed in U.S. Pat. No. 4,339,267.

Compounds of Formula III, where A is A-4, can be prepared by methods taught in European Patent Application No. 46,677 (published Mar. 3, 1982).

Compounds of Formula III, where A is A-5, can be prepared according to the methods taught in U.S. Pat. No. 4,421,550.

Compounds of Formula III, where A is A-6 and A-7, can be synthesized by procedures taught in U.S. Pat. No. 4,496,392 and in European Publication No. 125,864 (published Nov. 21, 1984).

Additional references dealing with the synthesis of bicyclic pyrimidines of Formula III, where A is A-2, A-3, or A-4 are Braker, Sheehan, Spitzmiller and Lott, *J. Am. Chem. Soc.*, 69, 3072(1947); Mitler and Bhattacharya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem. Soc.*, 63, 2188 (1941); and Fissekis, Myles and Brown, *J. Org. Chem.*, 29, 2670 (1964). All of the above are herein incorporated by reference.

Agriculturally suitable salts of compounds of Formula I are also useful herbicides and can be prepared in a manner of ways known to the art. For example, metal salts can be made by treating compounds of Formula I with a solution of an alkali or alkaline earth metal salt having a sufficiently basic anion (e.g., hydroxide, alkoxide, carbonate or hydride). Quaternary amine salts can be made by similar techniques. Detailed examples of such techniques are given in U.S. Pat. No. 4,127,405, the disclosure of which is herein incorporated by reference.

The compounds of this invention and their preparation are further illustrated by the following examples.

EXAMPLE 1

2-Methyl-4-benzothiazolesulfonyl chloride

2-Methylbenzothiazole (50 g) was added in a slow, dropwise manner to 86 mL of chlorosulfonic acid at room temperature. When the addition was complete, the dark reaction mixture was heated at 140°–145° C. for about 3 hours. The solution was allowed to cool and was slowly added to a large excess of ice. Insoluble solids were removed by filtration and the aqueous layer was extracted with benzene. Drying and evaporation of the solvent gave an off-white solid which was shown by $^1$H NMR analysis to consist of a mixture of sulfonyl chlorides, presumably the 4-, 6-, and 7-isomers. This crude material was recrystallized three times from hexane to remove the 6-isomer as a white solid, m.p. 100°–102° C. The combined mother liquors were concentrated to give a dark yellow oil which was carried on to the next step without further purification.

EXAMPLE 2

2-Methyl-4-benzothiazolesulfonamide

A solution of 18 g of the product from Example 1 in 170 mL of tetrahydrofuran was cooled to 0° C. under an atmosphere of nitrogen and treated with 5 mL of anhydrous ammonia. The mixture was stirred at room temperature for about an hour, filtered to remove the ammonium chloride, and the filtrate concentrated in vacuo to give an off-white solid. This crude product was purified by silica gel chromatography; elution with ethyl acetate-hexanes (3:1) gave 1.9 g of 2-methyl-4-benzothiazolesulfonamide as a white powder, m.p. 236°–239°

C.; NMR (DMSO-d$_6$/CDCl$_3$): δ 2.95 (3H, s), 7.0 (2H, br s, SO$_2$NH$_2$), 7.55 (1H, t, J=8 Hz), 8.0 (1H, dd, J=2,8 Hz), 8.2 (1H, dd, J=2,8 Hz).

EXAMPLE 3

N-[(4,6-Dimethoxypyrimidin-2-yl)aminocarbonyl]-2-methyl-4-benzothiazolesulfonamide A solution of 0.23 g of the product from Example 2 and 0.28 g of 4,6-dimethoxypyrimidin-2-ylcarbamic acid, phenyl ester in 5 mL of dry acetonitrile was treated at room temperature with 0.15 mL of 1,5-diazabicyclo[5.4.0]undec-5-ene (DBU), added over a period of about one minute. The reaction solution was stirred at room temperature for 1.5 hour and was then diluted with 2 mL of water and acidified by the addition of 5% aqueous hydrochloric acid. The resulting precipitate was collected by filtration, washed well with water and ether, and dried. The yield of N-[(4,6-dimethoxypyrimidin-2-yl)aminocarbonyl]-2-methyl-4-benzothiazolesulfonamide was 0.21 g as a white powder, m.p. 187°–194° C. NMR (CDCl$_3$/DMSO-d$_6$): δ 2.7 (3H, s), 4.05 (6H, s), 5.8 (1H, s), 7.5 (1H, t, J=8 Hz), 8.15 (1H, dd, J=2,8 Hz), 8.25 (1H, dd, J=2,8 Hz), 8.7 (1H, br s), 13.3 (1H, br s); IR(KBr): 3330, 1830, 1610, 1350, 1160 cm$^{-1}$.

EXAMPLE 4

3-Nitroacetanilide

A suspension of 13.8 g of 3-nitroaniline and 20 mL of triethylamine in 200 mL methylene chloride was cooled to 0° C. under a nitrogen atmosphere and treated with 10.2 g of acetyl chloride, added in a dropwise manner. The reaction mixture was allowed to warm to room temperature overnight. Removal of the volatiles in vacuo gave a crude yellow solid which was washed with 5% aqueous hydrochloric acid, water and was then dried. The yield of 3-nitroacetanilide was 17.4 g as a light yellow solid, m.p. 147°–149° C.; NMR (CDCl$_3$/DMSO-d$_6$): δ 2.1 (3H, br s), 7.5 (1H, t, J=9 Hz), 8.0 (2H, br t), 8.6 (1H, br s) 10.1 (1H, br s); IR(KBr): 1675, 1550, 1525, 1350 cm$^{-1}$.

EXAMPLE 5

3-Nitrothioacetanilide

A mixture of 5 g of the product from Example 4 and 4.7 g of 2,4-bis(4-methoxyphenyl)-1,3-dithia-2,4-diphosphetane-2,4-disulfide ("Lawesson's Reagent") in 30 mL of dry toluene was heated at 100° C. under an atmosphere of nitrogen for a period of 4 hours. The solvent was removed in vacuo, the residue was taken up in diethyl ether, washed with several portions of water, dried and concentrated to give an orange solid. This crude material was purified by passage through a column of silica gel. Elution with ether-hexane (1:1) afforded 5.6 g of 3-nitrothioacetanilide as a yellow solid, m.p. 90°–93° C.; NMR (CDCl$_3$/DMSO-d$_6$): δ 2.7 (3H, s), 7.6 (1H, t, J=8 Hz), 8.05 (1H, dd, J=2,8 Hz), 8.3 (1H, dd, J=2,8 Hz), 9.05 (1H, br s), 11.8 (1H, br s).

EXAMPLE 6

2-Methyl-7-nitrobenzothiazole

To a stirred suspension of 28.2 g of potassium ferricyanide in 39 mL water at room temperature was added, simultaneously, 41 mL of 8% aqueous sodium hydroxide and 6 g of the product from Example 5. After completion of the addition, the reaction mixture was stirred at room temperature for 1.5 hours. The insoluble solids were separated by filtration, washed with water, and then dissolved in 40 mL of 20% aqueous hydrochloric acid. After being heated on the steam bath for 15 minutes, this aqueous solution was filtered hot. The filtrate was allowed to cool and was diluted with three times its volume of cold water. The resulting solids were filtered and recrystallized from absolute ethanol to give 2.9 g of an off-white solid, m.p. 102°–105° C. Analysis by $^1$H NMR showed this material to be a mixture of the 7- and 5-nitro isomers. A second recrystallization from ethanol gave a sample of pure 2-methyl-7-nitrobenzothiazole as a white solid, m.p. 120°–121° C.; NMR(CDCl$_3$): δ 2.9 (3H, s), 7.7 (1H, t, J=8 Hz), 8.4 (2H, br t).

EXAMPLE 7

2-Methyl-7-aminobenzothiazole

To a solution of 3.8 g of the product from Example 6 and 8.1 g of glacial acetic acid in 56 mL absolute ethanol at reflux temperature was added 3.8 g of iron powder in small portions. The reaction mixture was heated at reflux temperature for about 36 hours, and was then cooled and filtered. The filtrate was concentrated in vacuo and the residue treated with several mL cold water to give a solid. Filtration and drying gave 2.2 g of the title compound as a tan-colored solid, m.p. 100°–101° C.; NMR (CDCl$_3$): δ 2.8 (3H, s), 3.9 (2H, br s), 6.65 (1H, d, J=8 Hz), 7.2 (1H, t, J=8 Hz), 7.5 (1H, d, J=8 Hz).

EXAMPLE 8

2-Methyl-7-benzothiazolesulfonamide

A suspension of 8 g of the product from Example 7 in 20 mL of concentrated hydrochloric acid was cooled to 0° C. and treated with a solution of 3.7 g sodium nitrite in 6 mL of water. After completion of the addition, the mixture was stirred at 0°–5° C. for about 15 minutes. This diazonium salt solution was then added all at once to a mixture of liquid sulfur dioxide, 2 g of cupric chloride dihydrate, and 4 mL water in 39 mL of glacial acetic acid at about 10° C.; vigorous gas evolution ensued. This reaction mixture was stirred at room temperature for another 4 hours, and was then poured into 190 mL ice-water. The resulting precipitate was collected by filtration, washed with water, and dried to give 9.2 g of 2-methyl-7-chlorosulfonylbenzothiazole as a yellow powder, m.p. 93°–97° C., dec; IR(KBr): 1380, 1175, 800, 770, 720 cm$^{-1}$.

EXAMPLE 9

2-Methyl-7-benzothiazolesulfonamide

A solution of 9.2 g of the product from Example 8 in 74 mL of dry tetrahydrofuran was cooled to 0° C. under nitrogen and treated with 2.5 mL of anhydrous ammonia. After being stirred at room temperature for 2 hours, the mixture was filtered and the solids collected were washed well with water and methylene chloride. The yield of 2-methylbenzothiazole-7-sulfonamide was 5.1 g as a white solid, m.p. 223°–224° C. NMR (DMSO-d$_6$/CDCl$_3$): δ 2.9 (3H, s) 7.1–7.9 (2H, br s), 7.7 (1H, t, J=9 Hz), 8.1 (1H, br d), 8.2 (1H, br d); IR(KBr): 3300, 3000, 1350, 1160, 1150 cm$^{-1}$.

EXAMPLE 10

N-[(4-methoxy-6-methylpyrimidin-2-yl)aminocarbonyl]-2-methyl-7-benzothiazolesulfonamide A suspension of 1.5 g of the product from Example 9 in 33 mL of 1,2-dichloroethane was cooled to 0° C. under a nitrogen atmosphere and treated with 3.6 mL of trimethylaluminum (2M solution in toluene). The mixture was warmed briefly to 50°-60° C., recooled to room temperature, and treated with 1.4 g of 4-methoxy-6-methylpyrimidin-2-yl-carbamic acid, methyl ester. This reaction mixture was heated at reflux temperature for approximately 48 hours and was then cooled to 0° C. and acidified by the addition of 5% aqueous hydrochloric acid. The resulting precipitate was separated by filtration and washed with water and 1-chlorobutane. The filtrate was dried over magnesium sulfate, treated with carbon, and concentrated in vacuo to give a yellow gum. Crystallization from hot acetonitrile afforded 0.45 g of the title compound as an off-white solid, m.p. 178°-180° C.; NMR (CDCl$_3$): δ 2.5 (3H, s), 2.8 (3H, s), 3.9 (3H, s), 6.3 (1H, s), 7.5-7.8 (1H, br s), 7.6 (1H, t), 8.2 (2H, br d); IR(KBr): 1710 (carbonyl stretch) cm$^{-1}$.

Utilizing the procedures of Equations 1-16 and Examples 1-10, the following compounds may be prepared by one skilled in the art.

TABLE 1

| Q | W | R | R$_1$ | R$_2$ | R$_3$ | X | Y | m.p. (°C.) |
|---|---|---|---|---|---|---|---|---|
| Q-1 | S | H | H | — | — | CH$_3$ | OCH$_3$ | |
| Q-1 | S | CH$_3$ | 5-F | — | — | CH$_3$ | OCH$_3$ | |
| Q-1 | S | CH$_3$ | 6-Cl | — | — | CH$_3$ | OCH$_3$ | |
| Q-1 | S | CH$_3$ | 5-Br | — | — | CH$_3$ | OCH$_3$ | |
| Q-1 | S | CH$_3$ | 6-CH$_3$ | — | — | CH$_3$ | OCH$_3$ | |
| Q-1 | S | CH$_3$ | 5-OCH$_3$ | — | — | CH$_3$ | OCH$_3$ | |
| Q-1 | S | CH$_3$ | 6-OCF$_2$H | — | — | CH$_3$ | OCH$_3$ | |
| Q-1 | S | C$_2$H$_5$ | H | — | — | CH$_3$ | OCH$_3$ | |
| Q-1 | S | i-C$_3$H$_7$ | H | — | — | CH$_3$ | OCH$_3$ | |
| Q-1 | S | t-C$_4$H$_9$ | H | — | — | CH$_3$ | OCH$_3$ | |
| Q-1 | S | CH$_3$ | H | — | — | CH$_3$ | CH$_3$ | 190-193 (d) |
| Q-1 | S | CH$_3$ | H | — | — | CH$_3$ | OCH$_3$ | 190-191 |
| Q-1 | S | CH$_3$ | H | — | — | OCH$_3$ | OCH$_3$ | 187-194 |
| Q-1 | S | CH$_3$ | H | — | — | OCH$_2$CH$_3$ | CH$_3$ | |
| Q-1 | S | CH$_3$ | H | — | — | Cl | OCH$_3$ | |
| Q-1 | S | CH$_3$ | H | — | — | F | OCH$_3$ | |
| Q-1 | S | CH$_3$ | H | — | — | Br | OCH$_3$ | |
| Q-1 | S | CH$_3$ | H | — | — | I | OCH$_3$ | |
| Q-1 | S | CH$_3$ | H | — | — | OCF$_2$H | CH$_3$ | |
| Q-1 | S | CH$_3$ | H | — | — | CH$_2$F | CH$_3$ | |
| Q-1 | S | CH$_3$ | H | — | — | OCH$_2$CH$_2$F | CH$_3$ | |
| Q-1 | S | CH$_3$ | H | — | — | OCH$_2$CHF$_2$ | CH$_3$ | |
| Q-1 | S | CH$_3$ | H | — | — | OCH$_2$CF$_3$ | CH$_3$ | |
| Q-1 | S | CH$_3$ | H | — | — | CF$_3$ | CH$_3$ | |
| Q-1 | S | CH$_3$ | H | — | — | CH$_3$ | H | |
| Q-1 | S | CH$_3$ | H | — | — | CH$_3$ | CH$_2$OCH$_3$ | |
| Q-1 | S | CH$_3$ | H | — | — | CH$_3$ | NHCH$_3$ | |
| Q-1 | S | CH$_3$ | H | — | — | CH$_3$ | N(OCH$_3$)CH$_3$ | |
| Q-1 | S | CH$_3$ | H | — | — | CH$_3$ | N(CH$_3$)$_2$ | |
| Q-1 | S | CH$_3$ | H | — | — | CH$_3$ | CH$_2$CH$_3$ | |
| Q-1 | S | CH$_3$ | H | — | — | CH$_3$ | SCH$_3$ | |
| Q-1 | S | CH$_3$ | H | — | — | CH$_3$ | OCH$_2$CH=CH$_2$ | |
| Q-1 | S | CH$_3$ | H | — | — | CH$_3$ | OCH$_2$C≡CH | |
| Q-1 | S | CH$_3$ | H | — | — | CH$_3$ | CH$_2$OCH$_2$CH$_3$ | |
| Q-1 | S | CH$_3$ | H | — | — | CH$_3$ | OCH$_2$CH$_2$OCH$_3$ | |
| Q-1 | S | CH$_3$ | H | — | — | CH$_3$ | CH$_2$SCH$_3$ | |
| Q-1 | S | CH$_3$ | H | — | — | CH$_3$ | CHO | |
| Q-1 | S | CH$_3$ | H | — | — | CH$_3$ | COCH$_3$ | |
| Q-1 | S | CH$_3$ | H | — | — | CH$_3$ | CH(OCH$_3$)$_2$ | |
| Q-1 | S | CH$_3$ | H | — | — | CH$_3$ | CH(OCH$_3$)SCH$_3$ | |
| Q-1 | S | CH$_3$ | H | — | — | CH$_3$ | CH(OCH$_2$CH$_3$)SCH$_3$ | |
| Q-1 | S | CH$_3$ | H | — | — | CH$_3$ | CH(OCH$_2$CH$_3$)OCH$_3$ | |
| Q-1 | S | CH$_3$ | H | — | — | CH$_3$ | C(OCH$_3$)$_2$CH$_3$ | |
| Q-1 | S | CH$_3$ | H | — | — | CH$_3$ | C(OCH$_3$)(SCH$_3$)CH$_3$ | |
| Q-1 | S | CH$_3$ | H | — | — | CH$_3$ | 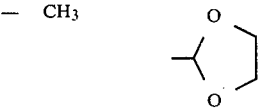 | |

TABLE 1-continued $$QSO_2NHCNH-\text{[pyrimidine with X at 4, Y at 6]}$$

| Q | W | R | $R_1$ | $R_2$ | $R_3$ | X | Y | m.p. (°C.) |
|---|---|---|---|---|---|---|---|---|
| Q-1 | S | $CH_3$ | H | — | — | $CH_3$ |  | |
| Q-1 | S | $CH_3$ | H | — | — | $CH_3$ |  | |
| Q-1 | S | $CH_3$ | H | — | — | $CH_3$ |  | |
| Q-1 | S | $CH_3$ | H | — | — | $CH_3$ |  | |
| Q-1 | S | $CH_3$ | H | — | — | $CH_3$ |  | |
| Q-1 | S | $CH_3$ | H | — | — | $CH_3$ |  | |
| Q-1 | S | $CH_3$ | H | — | — | $CH_3$ |  | |
| Q-1 | S | $CH_3$ | H | — | — | $CH_3$ | $SCF_2H$ | |
| Q-1 | S | $CH_3$ | H | — | — | $CH_3$ |  | |
| Q-1 | O | H | H | — | — | $OCH_3$ | $OCH_3$ | |
| Q-1 | O | $CH_3$ | 5-F | — | — | $OCH_3$ | $OCH_3$ | |
| Q-1 | O | $CH_3$ | 6-Cl | — | — | $OCH_3$ | $OCH_3$ | |
| Q-1 | O | $CH_3$ | 5-Br | — | — | $OCH_3$ | $OCH_3$ | |
| Q-1 | O | $CH_3$ | 6-$CH_3$ | — | — | $OCH_3$ | $OCH_3$ | |
| Q-1 | O | $CH_3$ | 5-$OCH_3$ | — | — | $OCH_3$ | $OCH_3$ | |
| Q-1 | O | $CH_3$ | 6-$OCF_2H$ | — | — | $OCH_3$ | $OCH_3$ | |
| Q-1 | O | $C_2H_5$ | H | — | — | $OCH_3$ | $OCH_3$ | |
| Q-1 | O | i-$C_3H_7$ | H | — | — | $OCH_3$ | $OCH_3$ | |
| Q-1 | O | t-$C_4H_9$ | H | — | — | $OCH_3$ | $OCH_3$ | |
| Q-1 | N | H | H | — | $CH_3$ | $OCH_3$ | $OCH_3$ | |
| Q-1 | N | $CH_3$ | 5-F | — | H | $OCH_3$ | $OCH_3$ | |
| Q-1 | N | $CH_3$ | 6-Cl | — | H | $OCH_3$ | $OCH_3$ | |
| Q-1 | N | $CH_3$ | 5-Br | — | H | $OCH_3$ | $OCH_3$ | |
| Q-1 | N | $CH_3$ | 6-$CH_3$ | — | H | $OCH_3$ | $OCH_3$ | |
| Q-1 | N | $CH_3$ | 5-$OCH_3$ | — | H | $OCH_3$ | $OCH_3$ | |
| Q-1 | N | $CH_3$ | 6-$OCF_2H$ | — | H | $OCH_3$ | $OCH_3$ | |
| Q-1 | N | $C_2H_5$ | H | — | H | $OCH_3$ | $OCH_3$ | |
| Q-1 | N | i-$C_3H_7$ | H | — | H | $OCH_3$ | $OCH_3$ | |
| Q-1 | N | t-$C_4H_9$ | H | — | H | $OCH_3$ | $OCH_3$ | |
| Q-2 | S | H | H | — | — | $CH_3$ | $OCH_3$ | |
| Q-2 | S | $CH_3$ | H | — | — | $CH_3$ | $CH_3$ | |

TABLE 1-continued $$QSO_2NHCNH-\underset{\underset{Y}{N}}{\overset{\overset{X}{N}}{\bigcirc}}$$

with C(=O) between NH groups

| Q | W | R | $R_1$ | $R_2$ | $R_3$ | X | Y | m.p. (°C.) |
|---|---|---|---|---|---|---|---|---|
| Q-2 | S | $CH_3$ | H | — | — | $CH_3$ | $OCH_3$ | 178–180 |
| Q-2 | S | $CH_3$ | H | — | — | $OCH_3$ | $OCH_3$ | 175–180 |
| Q-2 | S | $CH_3$ | 5-F | — | — | $CH_3$ | $OCH_3$ | |
| Q-2 | S | $CH_3$ | 6-Cl | — | — | $CH_3$ | $OCH_3$ | |
| Q-2 | S | $CH_3$ | 5-Br | — | — | $CH_3$ | $OCH_3$ | |
| Q-2 | S | $CH_3$ | 6-$CH_3$ | — | — | $CH_3$ | $OCH_3$ | |
| Q-2 | S | $CH_3$ | 5-$OCH_3$ | — | — | $CH_3$ | $OCH_3$ | |
| Q-2 | S | $CH_3$ | 6-$OCF_2H$ | — | — | $CH_3$ | $OCH_3$ | |
| Q-2 | S | $C_2H_5$ | H | — | — | $CH_3$ | $OCH_3$ | |
| Q-2 | S | i-$C_3H_7$ | H | — | — | $CH_3$ | $OCH_3$ | |
| Q-2 | S | t-$C_4H_9$ | H | — | — | $CH_3$ | $OCH_3$ | |
| Q-2 | O | H | H | — | — | $CH_3$ | $OCH_3$ | |
| Q-2 | O | $CH_3$ | H | — | — | $CH_3$ | $OCH_3$ | |
| Q-2 | O | $CH_3$ | 5-F | — | — | $CH_3$ | $OCH_3$ | |
| Q-2 | O | $CH_3$ | 6-Cl | — | — | $CH_3$ | $OCH_3$ | |
| Q-2 | O | $CH_3$ | 5-Br | — | — | $CH_3$ | $OCH_3$ | |
| Q-2 | O | $CH_3$ | 6-$CH_3$ | — | — | $CH_3$ | $OCH_3$ | |
| Q-2 | O | $CH_3$ | 5-$OCH_3$ | — | — | $CH_3$ | $OCH_3$ | |
| Q-2 | O | $CH_3$ | 6-$OCF_2H$ | — | — | $CH_3$ | $OCH_3$ | |
| Q-2 | O | $C_2H_5$ | H | — | — | $CH_3$ | $OCH_3$ | |
| Q-2 | O | i-$C_3H_7$ | H | — | — | $CH_3$ | $OCH_3$ | |
| Q-2 | O | t-$C_4H_9$ | H | — | — | $CH_3$ | $CH_3$ | |
| Q-2 | O | t-$C_4H_9$ | H | — | — | $CH_3$ | $OCH_3$ | 171–175 |
| Q-2 | O | t-$C_4H_9$ | H | — | — | $OCH_3$ | $OCH_3$ | 130–133 |
| Q-2 | N | H | H | — | $CH_3$ | $CH_3$ | $OCH_3$ | |
| Q-2 | N | $CH_3$ | 5-F | — | H | $CH_3$ | $OCH_3$ | |
| Q-2 | N | $CH_3$ | 6-Cl | — | H | $CH_3$ | $OCH_3$ | |
| Q-2 | N | $CH_3$ | 5-Br | — | H | $CH_3$ | $OCH_3$ | |
| Q-2 | N | $CH_3$ | 6-$CH_3$ | — | H | $CH_3$ | $OCH_3$ | |
| Q-2 | N | $CH_3$ | 5-$OCH_3$ | — | H | $CH_3$ | $OCH_3$ | |
| Q-2 | N | $CH_3$ | 6-$OCF_2H$ | — | H | $CH_3$ | $OCH_3$ | |
| Q-2 | N | $C_2H_5$ | H | — | H | $CH_3$ | $OCH_3$ | |
| Q-2 | N | i-$C_3H_7$ | H | — | H | $CH_3$ | $OCH_3$ | |
| Q-2 | N | t-$C_4H_9$ | H | — | H | $CH_3$ | $OCH_3$ | |
| Q-3 | S | — | H | H | — | $CH_3$ | $OCH_3$ | |
| Q-3 | S | — | H | $CH_3$ | — | $CH_3$ | $OCH_3$ | |
| Q-3 | S | — | 5-F | H | — | $CH_3$ | $OCH_3$ | |
| Q-3 | S | — | 6-Cl | H | — | $CH_3$ | $OCH_3$ | |
| Q-3 | S | — | 5-Br | H | — | $CH_3$ | $OCH_3$ | |
| Q-3 | S | — | 6-$CH_3$ | H | — | $CH_3$ | $OCH_3$ | |
| Q-3 | S | — | 5-$OCH_3$ | H | — | $CH_3$ | $OCH_3$ | |
| Q-3 | S | — | 6-$OCF_2H$ | H | — | $CH_3$ | $OCH_3$ | |
| Q-3 | O | — | H | H | — | $CH_3$ | $OCH_3$ | |
| Q-3 | O | — | H | $CH_3$ | — | $CH_3$ | $OCH_3$ | |
| Q-3 | O | — | 5-F | H | — | $CH_3$ | $OCH_3$ | |
| Q-3 | O | — | 6-Cl | H | — | $CH_3$ | $OCH_3$ | |
| Q-3 | O | — | 5-Br | H | — | $CH_3$ | $OCH_3$ | |
| Q-3 | O | — | 6-$CH_3$ | H | — | $CH_3$ | $OCH_3$ | |
| Q-3 | O | — | 5-$OCH_3$ | H | — | $CH_3$ | $OCH_3$ | |
| Q-3 | O | — | 6-$OCF_2H$ | H | — | $CH_3$ | $OCH_3$ | |
| Q-3 | N | — | H | H | $CH_3$ | $CH_3$ | $OCH_3$ | |
| Q-3 | N | — | H | $CH_3$ | H | $CH_3$ | $OCH_3$ | |
| Q-3 | N | — | 5-F | H | H | $CH_3$ | $OCH_3$ | |
| Q-3 | N | — | 6-Cl | H | H | $CH_3$ | $OCH_3$ | |
| Q-3 | N | — | 5-Br | H | H | $CH_3$ | $OCH_3$ | |
| Q-3 | N | — | 6-$CH_3$ | H | H | $CH_3$ | $OCH_3$ | |
| Q-3 | N | — | 5-$OCH_3$ | H | H | $CH_3$ | $OCH_3$ | |
| Q-3 | N | — | 6-$OCF_2H$ | H | H | $CH_3$ | $OCH_3$ | |
| Q-4 | S | — | H | H | — | $CH_3$ | $OCH_3$ | |
| Q-4 | S | — | H | $CH_3$ | — | $CH_3$ | $OCH_3$ | |
| Q-4 | S | — | 5-F | H | — | $CH_3$ | $OCH_3$ | |
| Q-4 | S | — | 6-Cl | H | — | $CH_3$ | $OCH_3$ | |
| Q-4 | S | — | 5-Br | H | — | $CH_3$ | $OCH_3$ | |
| Q-4 | S | — | 6-$CH_3$ | H | — | $CH_3$ | $OCH_3$ | |
| Q-4 | S | — | 5-$OCH_3$ | H | — | $CH_3$ | $OCH_3$ | |
| Q-4 | S | — | 6-$OCF_2H$ | H | — | $CH_3$ | $OCH_3$ | |
| Q-4 | O | — | H | H | — | $CH_3$ | $OCH_3$ | |
| Q-4 | O | — | H | $CH_3$ | — | $CH_3$ | $OCH_3$ | |
| Q-4 | O | — | 5-F | H | — | $CH_3$ | $OCH_3$ | |
| Q-4 | O | — | 6-Cl | H | — | $CH_3$ | $OCH_3$ | |
| Q-4 | O | — | 5-Br | H | — | $CH_3$ | $OCH_3$ | |
| Q-4 | O | — | 6-$CH_3$ | H | — | $CH_3$ | $OCH_3$ | |

TABLE 1-continued $$QSO_2NHCNH-\underset{O}{\overset{\|}{C}}-\text{pyrimidine with X, Y, R}_2, R_3$$

| Q | W | R | R$_1$ | R$_2$ | R$_3$ | X | Y | m.p. (°C.) |
|---|---|---|---|---|---|---|---|---|
| Q-4 | O | — | 5-OCH$_3$ | H | — | CH$_3$ | OCH$_3$ | |
| Q-4 | O | — | 6-OCF$_2$H | H | — | CH$_3$ | OCH$_3$ | |
| Q-4 | N | — | H | H | CH$_3$ | CH$_3$ | OCH$_3$ | |
| Q-4 | N | — | H | CH$_3$ | H | CH$_3$ | OCH$_3$ | |
| Q-4 | N | — | 5-F | H | H | CH$_3$ | OCH$_3$ | |
| Q-4 | N | — | 6-Cl | H | H | CH$_3$ | OCH$_3$ | |
| Q-4 | N | — | 5-Br | H | H | CH$_3$ | OCH$_3$ | |
| Q-4 | N | — | 6-CH$_3$ | H | H | CH$_3$ | OCH$_3$ | |
| Q-4 | N | — | 5-OCH$_3$ | H | H | CH$_3$ | OCH$_3$ | |
| Q-4 | N | — | 6-OCF$_2$H | H | H | CH$_3$ | OCH$_3$ | |
| Q-1 | S | CH$_3$ | H | — | — | CH$_3$ | CH(OCH$_2$CH$_3$)$_2$ | |
| Q-1 | S | CH$_3$ | H | — | — | CH$_3$ | CH(OCH$_3$)SCH$_2$CH$_3$ | |
| Q-1 | S | CH$_3$ | H | — | — | CH$_3$ | CH(OCH$_2$CH$_3$)SCH$_2$CH$_3$ | |
| Q-1 | S | CH$_3$ | H | — | — | CH$_3$ | CH(SCH$_3$)$_2$ | |
| Q-1 | S | CH$_3$ | H | — | — | CH$_3$ | CH(SCH$_2$CH$_3$)$_2$ | |
| Q-1 | S | CH$_3$ | H | — | — | CH$_3$ | CH(SCH$_2$CH$_3$)SCH$_3$ | |
| Q-1 | S | CH$_3$ | H | — | — | CH$_3$ | C(OCH$_2$CH$_3$)$_2$CH$_3$ | |
| Q-1 | S | CH$_3$ | H | — | — | CH$_3$ | C(OCH$_3$)(OCH$_2$CH$_3$)CH$_3$ | |
| Q-1 | S | CH$_3$ | H | — | — | CH$_3$ | C(OCH$_3$)(SCH$_2$CH$_3$)CH$_3$ | |
| Q-1 | S | CH$_3$ | H | — | — | CH$_3$ | C(OCH$_2$CH$_3$)(SCH$_3$)CH$_3$ | |
| Q-1 | S | CH$_3$ | H | — | — | CH$_3$ | C(OCH$_2$CH$_3$)(SCH$_2$CH$_3$)CH$_3$ | |
| Q-1 | S | CH$_3$ | H | — | — | CH$_3$ | C(SCH$_3$)$_2$CH$_3$ | |
| Q-1 | S | CH$_3$ | H | — | — | CH$_3$ | C(SCH$_2$CH$_3$)$_2$CH$_3$ | |
| Q-1 | S | CH$_3$ | H | — | — | CH$_3$ | C(SCH$_2$CH$_3$)(SCH$_3$)CH$_3$ | |
| Q-1 | S | CH$_3$ | H | — | — | CH$_3$ | C(CH$_3$)(O—)(O—) [1,3-dioxane, 2-CH$_3$] | |
| Q-1 | S | CH$_3$ | H | — | — | CH$_3$ | C(CH$_3$)(O—)(S—) [1,3-oxathiane, 2-CH$_3$] | |
| Q-1 | S | CH$_3$ | H | — | — | CH$_3$ | C(CH$_3$)(S—)(S—) [1,3-dithiane, 2-CH$_3$] | |
| Q-1 | S | CH$_3$ | H | — | — | CH$_3$ | CH(O—)(O—) [1,3-dioxane] | |
| Q-1 | S | CH$_3$ | H | — | — | CH$_3$ | CH(S—)(S—) [1,3-dithiane] | |
| Q-1 | S | CH$_3$ | H | — | — | CH$_3$ | CH(O—)(S—) [1,3-oxathiane] | |
| Q-1 | S | CH$_3$ | H | — | — | CH$_3$ | C(CH$_3$)(O—)(S—) [1,3-oxathiane, 2-CH$_3$] | |

TABLE 1-continued

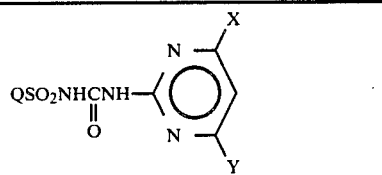

| Q | W | R | R₁ | R₂ | R₃ | X | Y | m.p. (°C.) |
|---|---|---|---|---|---|---|---|---|
| Q-1 | S | CH₃ | H | — | — | CH₃ | (isopropylidene dioxy group, CH₃/CH₃, O/O, CH₃) | |
| Q-1 | S | CH₃ | H | — | — | CH₃ | (isopropylidene O/S group with CH₃) | |
| Q-1 | S | CH₃ | H | — | — | CH₃ | (dithiolane with CH₃) | |
| Q-1 | S | CH₃ | H | — | — | CH₃ | C≡CH | |
| Q-1 | S | CH₃ | H | — | — | CH₃ | C≡CCH₃ | |
| Q-1 | S | CH₃ | H | — | — | OCH₃ | CH₂OCH₃ | |
| Q-1 | S | CH₃ | H | — | — | OCH₃ | NHCH₃ | |
| Q-1 | S | CH₃ | H | — | — | OCH₃ | CH₂CH₃ | |
| Q-1 | S | CH₃ | H | — | — | OCH₃ | CH(OCH₃)₂ | |
| Q-1 | S | CH₃ | H | — | — | OCH₃ | cyclopropyl | |
| Q-1 | S | CH₃ | H | — | — | OCH₃ | C≡CH | |
| Q-1 | S | CH₃ | H | — | — | OCH₃ | C≡CCH₃ | |
| Q-1 | S | CH₃ | H | — | — | Cl | NHCH₃ | |
| Q-1 | S | CH₃ | H | — | — | Br | NHCH₃ | |
| Q-1 | S | CH₃ | H | — | — | OCF₂H | OCH₃ | |
| Q-1 | S | CH₃ | H | — | — | OCF₂H | CH₂OCH₃ | |
| Q-1 | S | CH₃ | H | — | — | OCF₂H | NHCH₃ | |
| Q-1 | S | CH₃ | H | — | — | OCF₂H | CH₂CH₃ | |
| Q-1 | S | CH₃ | H | — | — | OCF₂H | CH(OCH₃)₂ | |
| Q-1 | S | CH₃ | H | — | — | OCF₂H | cyclopropyl | |
| Q-1 | S | CH₃ | H | — | — | OCF₂H | C≡CH | |
| Q-1 | S | CH₃ | H | — | — | OCF₂H | C≡CCH₃ | |
| Q-1 | S | CH₃ | 5-CF₃ | — | — | CH₃ | OCH₃ | |
| Q-1 | S | CH₃ | 6-CH₂OCH₃ | — | — | CH₃ | OCH₃ | |
| Q-1 | S | CH₃ | 5-CH₂SCH₃ | — | — | CH₃ | OCH₃ | |
| Q-1 | S | H | 5-F | — | — | CH₃ | OCH₃ | |
| Q-1 | S | H | 6-Cl | — | — | CH₃ | OCH₃ | |
| Q-1 | S | H | 5-Br | — | — | CH₃ | OCH₃ | |
| Q-1 | S | H | 6-CH₃ | — | — | CH₃ | OCH₃ | |
| Q-1 | S | H | 5-OCH₃ | — | — | CH₃ | OCH₃ | |
| Q-1 | S | H | 6-OCF₂H | — | — | CH₃ | OCH₃ | |
| Q-1 | S | H | 5-CF₃ | — | — | CH₃ | OCH₃ | |
| Q-1 | S | H | 6-CH₂OCH₃ | — | — | CH₃ | OCH₃ | |
| Q-1 | S | H | 5-CH₂SCH₃ | — | — | CH₃ | OCH₃ | |
| Q-1 | S | CH₂CH₃ | 5-F | — | — | CH₃ | OCH₃ | |
| Q-1 | S | CH₂CH₃ | 6-Cl | — | — | CH₃ | OCH₃ | |
| Q-1 | S | CH₂CH₃ | 5-Br | — | — | CH₃ | OCH₃ | |
| Q-1 | S | CH₂CH₃ | 6-CH₃ | — | — | CH₃ | OCH₃ | |
| Q-1 | S | CH₂CH₃ | 5-OCH₃ | — | — | CH₃ | OCH₃ | |
| Q-1 | S | CH₂CH₃ | 6-OCF₂H | — | — | CH₃ | OCH₃ | |
| Q-1 | S | CH₂CH₃ | 5-CF₃ | — | — | CH₃ | OCH₃ | |
| Q-1 | S | CH₂CH₃ | 6-CH₂OCH₃ | — | — | CH₃ | OCH₃ | |
| Q-1 | S | CH₂CH₃ | 5-CH₂SCH₃ | — | — | CH₃ | OCH₃ | |
| Q-1 | O | H | 5-F | — | — | OCH₃ | OCH₃ | |
| Q-1 | O | H | 6-Cl | — | — | OCH₃ | OCH₃ | |
| Q-1 | O | H | 5-Br | — | — | OCH₃ | OCH₃ | |
| Q-1 | O | H | 6-CH₃ | — | — | OCH₃ | OCH₃ | |
| Q-1 | O | H | 5-OCH₃ | — | — | OCH₃ | OCH₃ | |

TABLE 1-continued

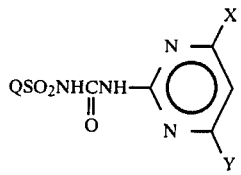

| Q | W | R | R₁ | R₂ | R₃ | X | Y | m.p. (°C.) |
|---|---|---|---|---|---|---|---|---|
| Q-1 | O | H | 6-OCF₂H | — | — | OCH₃ | OCH₃ | |
| Q-1 | O | H | 5-CF₃ | — | — | OCH₃ | OCH₃ | |
| Q-1 | O | H | 6-CH₂OCH₃ | — | — | OCH₃ | OCH₃ | |
| Q-1 | O | H | 5-CH₂SCH₃ | — | — | OCH₃ | OCH₃ | |
| Q-1 | O | CH₃ | H | — | — | OCH₃ | OCH₃ | |
| Q-1 | O | CH₃ | 5-CF₃ | — | — | OCH₃ | OCH₃ | |
| Q-1 | O | CH₃ | 6-CH₂OCH₃ | — | — | OCH₃ | OCH₃ | |
| Q-1 | O | CH₃ | 5-CH₂SCH₃ | — | — | OCH₃ | OCH₃ | |
| Q-1 | O | CH₂CH₃ | 5-F | — | — | OCH₃ | OCH₃ | |
| Q-1 | O | CH₂CH₃ | 6-Cl | — | — | OCH₃ | OCH₃ | |
| Q-1 | O | CH₂CH₃ | 5-Br | — | — | OCH₃ | OCH₃ | |
| Q-1 | O | CH₂CH₃ | 6-CH₃ | — | — | OCH₃ | OCH₃ | |
| Q-1 | O | CH₂CH₃ | 5-OCH₃ | — | — | OCH₃ | OCH₃ | |
| Q-1 | O | CH₂CH₃ | 6-OCF₂H | — | — | OCH₃ | OCH₃ | |
| Q-1 | O | CH₂CH₃ | 5-CF₃ | — | — | OCH₃ | OCH₃ | |
| Q-1 | O | CH₂CH₃ | 5-CH₂OCH₃ | — | — | OCH₃ | OCH₃ | |
| Q-1 | O | CH₂CH₃ | 6-CH₂SCH₃ | — | — | OCH₃ | OCH₃ | |
| Q-1 | N | H | H | — | H | OCH₃ | OCH₃ | |
| Q-1 | N | H | 5-F | — | H | OCH₃ | OCH₃ | |
| Q-1 | N | H | 6-Cl | — | H | OCH₃ | OCH₃ | |
| Q-1 | N | H | 5-Br | — | H | OCH₃ | OCH₃ | |
| Q-1 | N | H | 6-CH₃ | — | H | OCH₃ | OCH₃ | |
| Q-1 | N | H | 5-OCH₃ | — | H | OCH₃ | OCH₃ | |
| Q-1 | N | H | 6-OCF₂H | — | H | OCH₃ | OCH₃ | |
| Q-1 | N | H | 5-CF₃ | — | H | OCH₃ | OCH₃ | |
| Q-1 | N | H | 6-CH₂OCH₃ | — | H | OCH₃ | OCH₃ | |
| Q-1 | N | H | 5-CH₂SCH₃ | — | H | OCH₃ | OCH₃ | |
| Q-1 | N | H | 6-F | — | CH₃ | OCH₃ | OCH₃ | |
| Q-1 | N | H | 5-Cl | — | CH₃ | OCH₃ | OCH₃ | |
| Q-1 | N | H | 6-Br | — | CH₃ | OCH₃ | OCH₃ | |
| Q-1 | N | H | 5-CH₃ | — | CH₃ | OCH₃ | OCH₃ | |
| Q-1 | N | H | 6-OCH₃ | — | CH₃ | OCH₃ | OCH₃ | |
| Q-1 | N | H | 5-OCF₂H | — | CH₃ | OCH₃ | OCH₃ | |
| Q-1 | N | H | 6-CF₃ | — | CH₃ | OCH₃ | OCH₃ | |
| Q-1 | N | H | 5-CH₂OCH₃ | — | CH₃ | OCH₃ | OCH₃ | |
| Q-1 | N | H | 6-CH₂SCH₃ | — | CH₃ | OCH₃ | OCH₃ | |
| Q-1 | N | CH₃ | H | — | H | OCH₃ | OCH₃ | |
| Q-1 | N | CH₃ | 5-CF₃ | — | H | OCH₃ | OCH₃ | |
| Q-1 | N | CH₃ | 6-CH₂OCH₃ | — | H | OCH₃ | OCH₃ | |
| Q-1 | N | CH₃ | 5-CH₂SCH₃ | — | H | OCH₃ | OCH₃ | |
| Q-1 | N | CH₃ | H | — | CH₃ | OCH₃ | OCH₃ | |
| Q-1 | N | CH₃ | 5-F | — | CH₃ | OCH₃ | OCH₃ | |
| Q-1 | N | CH₃ | 6-Cl | — | CH₃ | OCH₃ | OCH₃ | |
| Q-1 | N | CH₃ | 5-Br | — | CH₃ | OCH₃ | OCH₃ | |
| Q-1 | N | CH₃ | 6-CH₃ | — | CH₃ | OCH₃ | OCH₃ | |
| Q-1 | N | CH₃ | 5-OCH₃ | — | CH₃ | OCH₃ | OCH₃ | |
| Q-1 | N | CH₃ | 6-OCF₂H | — | CH₃ | OCH₃ | OCH₃ | |
| Q-1 | N | CH₃ | 5-CF₃ | — | CH₃ | OCH₃ | OCH₃ | |
| Q-1 | N | CH₃ | 6-CH₂OCH₃ | — | CH₃ | OCH₃ | OCH₃ | |
| Q-1 | N | CH₃ | 5-CH₂SCH₃ | — | CH₃ | OCH₃ | OCH₃ | |
| Q-1 | N | CH₂CH₃ | 5-F | — | H | OCH₃ | OCH₃ | |
| Q-1 | N | CH₂CH₃ | 6-Cl | — | H | OCH₃ | OCH₃ | |
| Q-1 | N | CH₂CH₃ | 5-Br | — | H | OCH₃ | OCH₃ | |
| Q-1 | N | CH₂CH₃ | 6-CH₃ | — | H | OCH₃ | OCH₃ | |
| Q-1 | N | CH₂CH₃ | 5-OCH₃ | — | H | OCH₃ | OCH₃ | |
| Q-1 | N | CH₂CH₃ | 6-OCF₂H | — | H | OCH₃ | OCH₃ | |
| Q-1 | N | CH₂CH₃ | 5-CF₃ | — | H | OCH₃ | OCH₃ | |
| Q-1 | N | CH₂CH₃ | 6-CH₂OCH₃ | — | H | OCH₃ | OCH₃ | |
| Q-1 | N | CH₂CH₃ | 5-CH₂SCH₃ | — | H | OCH₃ | OCH₃ | |
| Q-1 | N | CH₂CH₃ | H | — | CH₃ | OCH₃ | OCH₃ | |
| Q-1 | N | CH₂CH₃ | 5-F | — | CH₃ | OCH₃ | OCH₃ | |
| Q-1 | N | CH₂CH₃ | 6-Cl | — | CH₃ | OCH₃ | OCH₃ | |
| Q-1 | N | CH₂CH₃ | 5-Br | — | CH₃ | OCH₃ | OCH₃ | |
| Q-1 | N | CH₂CH₃ | 6-CH₃ | — | CH₃ | OCH₃ | OCH₃ | |
| Q-1 | N | CH₂CH₃ | 5-OCH₃ | — | CH₃ | OCH₃ | OCH₃ | |
| Q-1 | N | CH₂CH₃ | 6-OCF₂H | — | CH₃ | OCH₃ | OCH₃ | |
| Q-1 | N | CH₂CH₃ | 5-CF₃ | — | CH₃ | OCH₃ | OCH₃ | |
| Q-1 | N | CH₂CH₃ | 6-CH₂OCH₃ | — | CH₃ | OCH₃ | OCH₃ | |
| Q-1 | N | CH₂CH₃ | 5-CH₂SCH₃ | — | CH₃ | OCH₃ | OCH₃ | |
| Q-2 | S | CH₃ | 5-CF₃ | — | — | CH₃ | OCH₃ | |
| Q-2 | S | CH₃ | 6-CH₂OCH₃ | — | — | CH₃ | OCH₃ | |
| Q-2 | S | CH₃ | 5-CH₂SCH₃ | — | — | CH₃ | OCH₃ | |

TABLE 1-continued

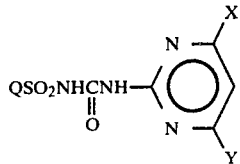

| Q | W | R | R₁ | R₂ | R₃ | X | Y | m.p. (°C.) |
|---|---|---|---|---|---|---|---|---|
| Q-2 | S | H | 5-F | — | — | $CH_3$ | $OCH_3$ | |
| Q-2 | S | H | 6-Cl | — | — | $CH_3$ | $OCH_3$ | |
| Q-2 | S | H | 5-Br | — | — | $CH_3$ | $OCH_3$ | |
| Q-2 | S | H | 6-$CH_3$ | — | — | $CH_3$ | $OCH_3$ | |
| Q-2 | S | H | 5-$OCH_3$ | — | — | $CH_3$ | $OCH_3$ | |
| Q-2 | S | H | 6-$OCF_2H$ | — | — | $CH_3$ | $OCH_3$ | |
| Q-2 | S | H | 5-$CF_3$ | — | — | $CH_3$ | $OCH_3$ | |
| Q-2 | S | H | 6-$CH_2OCH_3$ | — | — | $CH_3$ | $OCH_3$ | |
| Q-2 | S | H | 5-$CH_2SCH_3$ | — | — | $CH_3$ | $OCH_3$ | |
| Q-2 | S | $CH_2CH_3$ | 5-F | — | — | $CH_3$ | $OCH_3$ | |
| Q-2 | S | $CH_2CH_3$ | 6-Cl | — | — | $CH_3$ | $OCH_3$ | |
| Q-2 | S | $CH_2CH_3$ | 5-Br | — | — | $CH_3$ | $OCH_3$ | |
| Q-2 | S | $CH_2CH_3$ | 6-$CH_3$ | — | — | $CH_3$ | $OCH_3$ | |
| Q-2 | S | $CH_2CH_3$ | 5-$OCH_3$ | — | — | $CH_3$ | $OCH_3$ | |
| Q-2 | S | $CH_2CH_3$ | 6-$OCF_2H$ | — | — | $CH_3$ | $OCH_3$ | |
| Q-2 | S | $CH_2CH_3$ | 5-$CF_3$ | — | — | $CH_3$ | $OCH_3$ | |
| Q-2 | S | $CH_2CH_3$ | 6-$CH_2OCH_3$ | — | — | $CH_3$ | $OCH_3$ | |
| Q-2 | S | $CH_2CH_3$ | 5-$CH_2SCH_3$ | — | — | $CH_3$ | $OCH_3$ | |
| Q-2 | O | $CH_3$ | 5-$CF_3$ | — | — | $CH_3$ | $OCH_3$ | |
| Q-2 | O | $CH_3$ | 6-$CH_2OCH_3$ | — | — | $CH_3$ | $OCH_3$ | |
| Q-2 | O | $CH_3$ | 5-$CH_2SCH_3$ | — | — | $CH_3$ | $OCH_3$ | |
| Q-2 | N | H | H | — | H | $CH_3$ | $OCH_3$ | |
| Q-2 | N | $CH_3$ | H | — | H | $CH_3$ | $OCH_3$ | |
| Q-2 | N | $CH_3$ | 5-$CF_3$ | — | H | $CH_3$ | $OCH_3$ | |
| Q-2 | N | $CH_3$ | 6-$CH_2OCH_3$ | — | H | $CH_3$ | $OCH_3$ | |
| Q-2 | N | $CH_3$ | 5-$CH_2SCH_3$ | — | H | $CH_3$ | $OCH_3$ | |
| Q-2 | N | $CH_3$ | 5-F | — | $CH_3$ | $CH_3$ | $OCH_3$ | |
| Q-2 | N | $CH_3$ | 6-Cl | — | $CH_3$ | $CH_3$ | $OCH_3$ | |
| Q-2 | N | $CH_3$ | 5-Br | — | $CH_3$ | $CH_3$ | $OCH_3$ | |
| Q-2 | N | $CH_3$ | 6-$CH_3$ | — | $CH_3$ | $CH_3$ | $OCH_3$ | |
| Q-2 | N | $CH_3$ | 5-$OCH_3$ | — | $CH_3$ | $CH_3$ | $OCH_3$ | |
| Q-2 | N | $CH_3$ | 6-$OCF_2H$ | — | $CH_3$ | $CH_3$ | $OCH_3$ | |
| Q-2 | N | $CH_3$ | 5-$CF_3$ | — | $CH_3$ | $CH_3$ | $OCH_3$ | |
| Q-2 | N | $CH_3$ | 6-$CH_2OCH_3$ | — | $CH_3$ | $CH_3$ | $OCH_3$ | |
| Q-2 | N | $CH_3$ | 5-$CH_2SCH_3$ | — | $CH_3$ | $CH_3$ | $OCH_3$ | |
| Q-2 | N | $CH_2CH_3$ | H | — | $CH_3$ | $CH_3$ | $OCH_3$ | |
| Q-3 | S | — | 5-$CF_3$ | H | — | $CH_3$ | $OCH_3$ | |
| Q-3 | S | — | 6-$CH_2OCH_3$ | H | — | $CH_3$ | $OCH_3$ | |
| Q-3 | S | — | 5-$CH_2SCH_3$ | H | — | $CH_3$ | $OCH_3$ | |
| Q-3 | S | — | 5-F | $CH_3$ | — | $CH_3$ | $OCH_3$ | |
| Q-3 | S | — | 6-Cl | $CH_3$ | — | $CH_3$ | $OCH_3$ | |
| Q-3 | S | — | 5-Br | $CH_3$ | — | $CH_3$ | $OCH_3$ | |
| Q-3 | S | — | 6-$CH_3$ | $CH_3$ | — | $CH_3$ | $OCH_3$ | |
| Q-3 | S | — | 5-$OCH_3$ | $CH_3$ | — | $CH_3$ | $OCH_3$ | |
| Q-3 | S | — | 6-$OCF_2H$ | $CH_3$ | — | $CH_3$ | $OCH_3$ | |
| Q-3 | S | — | 5-$CF_3$ | $CH_3$ | — | $CH_3$ | $OCH_3$ | |
| Q-3 | S | — | 6-$CH_2OCH_3$ | $CH_3$ | — | $CH_3$ | $OCH_3$ | |
| Q-3 | S | — | 5-$CH_2SCH_3$ | $CH_3$ | — | $CH_3$ | $OCH_3$ | |
| Q-3 | O | — | 6-$CF_3$ | H | — | $CH_3$ | $OCH_3$ | |
| Q-3 | O | — | 5-$CH_2OCH_3$ | H | — | $CH_3$ | $OCH_3$ | |
| Q-3 | O | — | 6-$CH_2SCH_3$ | H | — | $CH_3$ | $OCH_3$ | |
| Q-3 | N | — | 5-$CF_3$ | H | H | $CH_3$ | $OCH_3$ | |
| Q-3 | N | — | 6-$CH_2OCH_3$ | H | H | $CH_3$ | $OCH_3$ | |
| Q-3 | N | — | 5-$CH_2SCH_3$ | H | H | $CH_3$ | $OCH_3$ | |
| Q-3 | N | — | H | H | H | $CH_3$ | $OCH_3$ | |
| Q-4 | S | — | 5-$CF_3$ | H | — | $CH_3$ | $OCH_3$ | |
| Q-4 | S | — | 6-$CH_2OCH_3$ | H | — | $CH_3$ | $OCH_3$ | |
| Q-4 | S | — | 5-$CH_2SCH_3$ | H | — | $CH_3$ | $OCH_3$ | |
| Q-4 | S | — | 5-F | $CH_3$ | — | $CH_3$ | $OCH_3$ | |
| Q-4 | S | — | 6-Cl | $CH_3$ | — | $CH_3$ | $OCH_3$ | |
| Q-4 | S | — | 5-Br | $CH_3$ | — | $CH_3$ | $OCH_3$ | |
| Q-4 | S | — | 6-$CH_3$ | $CH_3$ | — | $CH_3$ | $OCH_3$ | |
| Q-4 | S | — | 5-$OCH_3$ | $CH_3$ | — | $CH_3$ | $OCH_3$ | |
| Q-4 | S | — | 6-$OCF_2H$ | $CH_3$ | — | $CH_3$ | $OCH_3$ | |
| Q-4 | S | — | 5-$CF_3$ | $CH_3$ | — | $CH_3$ | $OCH_3$ | |
| Q-4 | S | — | 6-$CH_2OCH_3$ | $CH_3$ | — | $CH_3$ | $OCH_3$ | |
| Q-4 | S | — | 5-$CH_2SCH_3$ | $CH_3$ | — | $CH_3$ | $OCH_3$ | |
| Q-4 | O | — | 5-$CF_3$ | H | — | $CH_3$ | $OCH_3$ | |
| Q-4 | O | — | 6-$CH_2OCH_3$ | H | — | $CH_3$ | $OCH_3$ | |
| Q-4 | O | — | 5-$CH_2SCH_3$ | H | — | $CH_3$ | $OCH_3$ | |
| Q-4 | N | — | H | H | H | $CH_3$ | $OCH_3$ | |
| Q-4 | N | — | 5-$CF_3$ | H | H | $CH_3$ | $OCH_3$ | |

TABLE 1-continued

QSO₂NHCNH— [pyrimidine ring with X, Y]
        ‖
        O

| Q | W | R | R₁ | R₂ | R₃ | X | Y | m.p. (°C.) |
|---|---|---|----|----|----|---|---|------------|
| Q-4 | N | — | 6-CH₂OCH₃ | H | H | CH₃ | OCH₃ | |
| Q-4 | N | — | 5-CH₂SCH₃ | H | H | CH₃ | OCH₃ | |

TABLE 2

QSO₂NHCNH— [triazine ring with X, Y]
        ‖
        O

| Q | W | R | R₁ | R₂ | R₃ | X | Y | m.p. (°C.) |
|---|---|---|----|----|----|---|---|------------|
| Q-1 | S | H | H | — | — | CH₃ | OCH₃ | |
| Q-1 | S | CH₃ | 5-F | — | — | CH₃ | OCH₃ | |
| Q-1 | S | CH₃ | 6-Cl | — | — | CH₃ | OCH₃ | |
| Q-1 | S | CH₃ | 5-Br | — | — | CH₃ | OCH₃ | |
| Q-1 | S | CH₃ | 6-CH₃ | — | — | CH₃ | OCH₃ | |
| Q-1 | S | CH₃ | 5-OCH₃ | — | — | CH₃ | OCH₃ | |
| Q-1 | S | CH₃ | 6-OCF₂H | — | — | CH₃ | OCH₃ | |
| Q-1 | S | C₂H₅ | H | — | — | CH₃ | OCH₃ | |
| Q-1 | S | i-C₃H₇ | H | — | — | CH₃ | OCH₃ | |
| Q-1 | S | t-C₄H₉ | H | — | — | CH₃ | OCH₃ | |
| Q-1 | S | CH₃ | H | — | — | CH₃ | CH₃ | |
| Q-1 | S | CH₃ | H | — | — | CH₃ | OCH₃ | 182.5–183 |
| Q-1 | S | CH₃ | H | — | — | OCH₃ | OCH₃ | 182–185 |
| Q-1 | S | CH₃ | H | — | — | OCH₂CH₃ | CH₃ | |
| Q-1 | S | CH₃ | H | — | — | CH₂F | CH₃ | |
| Q-1 | S | CH₃ | H | — | — | OCH₂CH₂F | CH₃ | |
| Q-1 | S | CH₃ | H | — | — | OCH₂CHF₂ | CH₃ | |
| Q-1 | S | CH₃ | H | — | — | OCH₂CF₃ | CH₃ | |
| Q-1 | S | CH₃ | H | — | — | CF₃ | CH₃ | |
| Q-1 | S | CH₃ | H | — | — | CH₃ | H | |
| Q-1 | S | CH₃ | H | — | — | CH₃ | CH₂OCH₃ | |
| Q-1 | S | CH₃ | H | — | — | CH₃ | NHCH₃ | |
| Q-1 | S | CH₃ | H | — | — | CH₃ | N(OCH₃)CH₃ | |
| Q-1 | S | CH₃ | H | — | — | CH₃ | N(CH₃)₂ | |
| Q-1 | S | CH₃ | H | — | — | CH₃ | CH₂CH₃ | |
| Q-1 | S | CH₃ | H | — | — | CH₃ | SCH₃ | |
| Q-1 | S | CH₃ | H | — | — | CH₃ | OCH₂CH=CH₂ | |
| Q-1 | S | CH₃ | H | — | — | CH₃ | OCH₂C≡CH | |
| Q-1 | S | CH₃ | H | — | — | CH₃ | CH₂OCH₂CH₃ | |
| Q-1 | S | CH₃ | H | — | — | CH₃ | OCH₂CH₂OCH₃ | |
| Q-1 | S | CH₃ | H | — | — | CH₃ | CH₂SCH₃ | |
| Q-1 | S | CH₃ | H | — | — | CH₃ | CHO | |
| Q-1 | S | CH₃ | H | — | — | CH₃ | COCH₃ | |
| Q-1 | S | CH₃ | H | — | — | CH₃ | CH(OCH₃)₂ | |
| Q-1 | S | CH₃ | H | — | — | CH₃ | CH(OCH₃)SCH₃ | |
| Q-1 | S | CH₃ | H | — | — | CH₃ | CH(OCH₂CH₃)SCH₃ | |
| Q-1 | S | CH₃ | H | — | — | CH₃ | CH(OCH₂CH₃)OCH₃ | |
| Q-1 | S | CH₃ | H | — | — | CH₃ | C(OCH₃)₂CH₃ | |
| Q-1 | S | CH₃ | H | — | — | CH₃ | C(OCH₃)(SCH₃)CH₃ | |
| Q-1 | S | CH₃ | H | — | — | CH₃ | 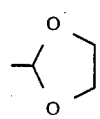 | |
| Q-1 | S | CH₃ | H | — | — | CH₃ | 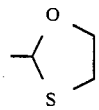 | |

TABLE 2-continued

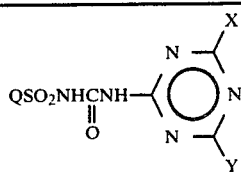

| Q | W | R | R₁ | R₂ | R₃ | X | Y | m.p. (°C.) |
|---|---|---|---|---|---|---|---|---|
| Q-1 | S | $CH_3$ | H | — | — | $CH_3$ | (S-CH-S ring, dithiane) | |
| Q-1 | S | $CH_3$ | H | — | — | $CH_3$ | (O-C(CH₃)-O dioxolane) | |
| Q-1 | S | $CH_3$ | H | — | — | $CH_3$ | (S-C(CH₃)-S dithiolane) | |
| Q-1 | S | $CH_3$ | H | — | — | $CH_3$ | (O-CH-O with CH₃) | |
| Q-1 | S | $CH_3$ | H | — | — | $CH_3$ | (O-CH-S with CH₃) | |
| Q-1 | S | $CH_3$ | H | — | — | $CH_3$ | (S-C(CH₃)-S with CH₃) | |
| Q-1 | S | $CH_3$ | H | — | — | $CH_3$ | $SCF_2H$ | |
| Q-1 | S | $CH_3$ | H | — | — | $CH_3$ | cyclopropyl | |
| Q-1 | O | H | H | — | — | $OCH_3$ | $OCH_3$ | |
| Q-1 | O | $CH_3$ | 5-F | — | — | $OCH_3$ | $OCH_3$ | |
| Q-1 | O | $CH_3$ | 6-Cl | — | — | $OCH_3$ | $OCH_3$ | |
| Q-1 | O | $CH_3$ | 5-Br | — | — | $OCH_3$ | $OCH_3$ | |
| Q-1 | O | $CH_3$ | 6-$CH_3$ | — | — | $OCH_3$ | $OCH_3$ | |
| Q-1 | O | $CH_3$ | 5-$OCH_3$ | — | — | $OCH_3$ | $OCH_3$ | |
| Q-1 | O | $CH_3$ | 6-$OCF_2H$ | — | — | $OCH_3$ | $OCH_3$ | |
| Q-1 | O | $C_2H_5$ | H | — | — | $OCH_3$ | $OCH_3$ | |
| Q-1 | O | i-$C_3H_7$ | H | — | — | $OCH_3$ | $OCH_3$ | |
| Q-1 | O | t-$C_4H_9$ | H | — | — | $OCH_3$ | $OCH_3$ | |
| Q-1 | N | H | H | — | $CH_3$ | $OCH_3$ | $OCH_3$ | |
| Q-1 | N | $CH_3$ | 5-F | — | H | $OCH_3$ | $OCH_3$ | |
| Q-1 | N | $CH_3$ | 6-Cl | — | H | $OCH_3$ | $OCH_3$ | |
| Q-1 | N | $CH_3$ | 5-Br | — | H | $OCH_3$ | $OCH_3$ | |
| Q-1 | N | $CH_3$ | 6-$CH_3$ | — | H | $OCH_3$ | $OCH_3$ | |
| Q-1 | N | $CH_3$ | 5-$OCH_3$ | — | H | $OCH_3$ | $OCH_3$ | |
| Q-1 | N | $CH_3$ | 6-$OCF_2H$ | — | H | $OCH_3$ | $OCH_3$ | |
| Q-1 | N | $C_2H_5$ | H | — | H | $OCH_3$ | $OCH_3$ | |
| Q-1 | N | i-$C_3H_7$ | H | — | H | $OCH_3$ | $OCH_3$ | |
| Q-1 | N | t-$C_4H_9$ | H | — | H | $OCH_3$ | $OCH_3$ | |
| Q-2 | S | H | H | — | — | $CH_3$ | $OCH_3$ | |
| Q-2 | S | $CH_3$ | H | — | — | $CH_3$ | $CH_3$ | |
| Q-2 | S | $CH_3$ | H | — | — | $CH_3$ | $OCH_3$ | |
| Q-2 | S | $CH_3$ | H | — | — | $OCH_3$ | $OCH_3$ | 152–156 (d) |
| Q-2 | S | $CH_3$ | 5-F | — | — | $CH_3$ | $OCH_3$ | |
| Q-2 | S | $CH_3$ | 6-Cl | — | — | $CH_3$ | $OCH_3$ | |
| Q-2 | S | $CH_3$ | 5-Br | — | — | $CH_3$ | $OCH_3$ | |
| Q-2 | S | $CH_3$ | 6-$CH_3$ | — | — | $CH_3$ | $OCH_3$ | |

TABLE 2-continued

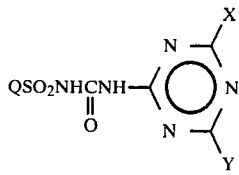

| Q | W | R | $R_1$ | $R_2$ | $R_3$ | X | Y | m.p. (°C.) |
|---|---|---|---|---|---|---|---|---|
| Q-2 | S | $CH_3$ | 5-$OCH_3$ | — | — | $CH_3$ | $OCH_3$ | |
| Q-2 | S | $CH_3$ | 6-$OCF_2H$ | — | — | $CH_3$ | $OCH_3$ | |
| Q-2 | S | $C_2H_5$ | H | — | — | $CH_3$ | $OCH_3$ | |
| Q-2 | S | i-$C_3H_7$ | H | — | — | $CH_3$ | $OCH_3$ | |
| Q-2 | S | t-$C_4H_9$ | H | — | — | $CH_3$ | $OCH_3$ | |
| Q-2 | O | H | H | — | — | $CH_3$ | $OCH_3$ | |
| Q-2 | O | $CH_3$ | H | — | — | $CH_3$ | $OCH_3$ | |
| Q-2 | O | $CH_3$ | 5-F | — | — | $CH_3$ | $OCH_3$ | |
| Q-2 | O | $CH_3$ | 6-Cl | — | — | $CH_3$ | $OCH_3$ | |
| Q-2 | O | $CH_3$ | 5-Br | — | — | $CH_3$ | $OCH_3$ | |
| Q-2 | O | $CH_3$ | 6-$CH_3$ | — | — | $CH_3$ | $OCH_3$ | |
| Q-2 | O | $CH_3$ | 5-$OCH_3$ | — | — | $CH_3$ | $OCH_3$ | |
| Q-2 | O | $CH_3$ | 6-$OCF_2H$ | — | — | $CH_3$ | $OCH_3$ | |
| Q-2 | O | $C_2H_5$ | H | — | — | $CH_3$ | $OCH_3$ | |
| Q-2 | O | i-$C_3H_7$ | H | — | — | $CH_3$ | $OCH_3$ | |
| Q-2 | O | t-$C_4H_9$ | H | — | — | $CH_3$ | $CH_3$ | |
| Q-2 | O | t-$C_4H_9$ | H | — | — | $CH_3$ | $OCH_3$ | 149–153 |
| Q-2 | O | t-$C_4H_9$ | H | — | — | $OCH_3$ | $OCH_3$ | |
| Q-2 | N | H | H | — | $CH_3$ | $CH_3$ | $OCH_3$ | |
| Q-2 | N | $CH_3$ | 5-F | — | H | $CH_3$ | $OCH_3$ | |
| Q-2 | N | $CH_3$ | 6-Cl | — | H | $CH_3$ | $OCH_3$ | |
| Q-2 | N | $CH_3$ | 5-Br | — | H | $CH_3$ | $OCH_3$ | |
| Q-2 | N | $CH_3$ | 6-$CH_3$ | — | H | $CH_3$ | $OCH_3$ | |
| Q-2 | N | $CH_3$ | 5-$OCH_3$ | — | H | $CH_3$ | $OCH_3$ | |
| Q-2 | N | $CH_3$ | 6-$OCF_2H$ | — | H | $CH_3$ | $OCH_3$ | |
| Q-2 | N | $C_2H_5$ | H | — | H | $CH_3$ | $OCH_3$ | |
| Q-2 | N | i-$C_3H_7$ | H | — | H | $CH_3$ | $OCH_3$ | |
| Q-2 | N | t-$C_4H_9$ | H | — | H | $CH_3$ | $OCH_3$ | |
| Q-3 | S | — | H | H | — | $CH_3$ | $OCH_3$ | |
| Q-3 | S | — | H | $CH_3$ | — | $CH_3$ | $OCH_3$ | |
| Q-3 | S | — | 5-F | H | — | $CH_3$ | $OCH_3$ | |
| Q-3 | S | — | 6-Cl | H | — | $CH_3$ | $OCH_3$ | |
| Q-3 | S | — | 5-Br | H | — | $CH_3$ | $OCH_3$ | |
| Q-3 | S | — | 6-$CH_3$ | H | — | $CH_3$ | $OCH_3$ | |
| Q-3 | S | — | 5-$OCH_3$ | H | — | $CH_3$ | $OCH_3$ | |
| Q-3 | S | — | 6-$OCF_2H$ | H | — | $CH_3$ | $OCH_3$ | |
| Q-3 | O | — | H | H | — | $CH_3$ | $OCH_3$ | |
| Q-3 | O | — | H | $CH_3$ | — | $CH_3$ | $OCH_3$ | |
| Q-3 | O | — | 5-F | H | — | $CH_3$ | $OCH_3$ | |
| Q-3 | O | — | 6-Cl | H | — | $CH_3$ | $OCH_3$ | |
| Q-3 | O | — | 5-Br | H | — | $CH_3$ | $OCH_3$ | |
| Q-3 | O | — | 6-$CH_3$ | H | — | $CH_3$ | $OCH_3$ | |
| Q-3 | O | — | 5-$OCH_3$ | H | — | $CH_3$ | $OCH_3$ | |
| Q-3 | O | — | 6-$OCF_2H$ | H | — | $CH_3$ | $OCH_3$ | |
| Q-3 | N | — | H | H | $CH_3$ | $CH_3$ | $OCH_3$ | |
| Q-3 | N | — | H | $CH_3$ | H | $CH_3$ | $OCH_3$ | |
| Q-3 | N | — | 5-F | H | H | $CH_3$ | $OCH_3$ | |
| Q-3 | N | — | 6-Cl | H | H | $CH_3$ | $OCH_3$ | |
| Q-3 | N | — | 5-Br | H | H | $CH_3$ | $OCH_3$ | |
| Q-3 | N | — | 6-$CH_3$ | H | H | $CH_3$ | $OCH_3$ | |
| Q-3 | N | — | 5-$OCH_3$ | H | H | $CH_3$ | $OCH_3$ | |
| Q-3 | N | — | 6-$OCF_2H$ | H | H | $CH_3$ | $OCH_3$ | |
| Q-4 | S | — | H | H | — | $CH_3$ | $OCH_3$ | |
| Q-4 | S | — | H | $CH_3$ | — | $CH_3$ | $OCH_3$ | |
| Q-4 | S | — | 5-F | H | — | $CH_3$ | $OCH_3$ | |
| Q-4 | S | — | 6-Cl | H | — | $CH_3$ | $OCH_3$ | |
| Q-4 | S | — | 5-Br | H | — | $CH_3$ | $OCH_3$ | |
| Q-4 | S | — | 6-$CH_3$ | H | — | $CH_3$ | $OCH_3$ | |
| Q-4 | S | — | 5-$OCH_3$ | H | — | $CH_3$ | $OCH_3$ | |
| Q-4 | S | — | 6-$OCF_2H$ | H | — | $CH_3$ | $OCH_3$ | |
| Q-4 | O | — | H | H | — | $CH_3$ | $OCH_3$ | |
| Q-4 | O | — | H | $CH_3$ | — | $CH_3$ | $OCH_3$ | |
| Q-4 | O | — | 5-F | H | — | $CH_3$ | $OCH_3$ | |
| Q-4 | O | — | 6-Cl | H | — | $CH_3$ | $OCH_3$ | |
| Q-4 | O | — | 5-Br | H | — | $CH_3$ | $OCH_3$ | |
| Q-4 | O | — | 6-$CH_3$ | H | — | $CH_3$ | $OCH_3$ | |
| Q-4 | O | — | 5-$OCH_3$ | H | — | $CH_3$ | $OCH_3$ | |
| Q-4 | O | — | 6-$OCF_2H$ | H | — | $CH_3$ | $OCH_3$ | |
| Q-4 | N | — | H | H | $CH_3$ | $CH_3$ | $OCH_3$ | |
| Q-4 | N | — | H | $CH_3$ | H | $CH_3$ | $OCH_3$ | |
| Q-4 | N | — | 5-F | H | H | $CH_3$ | $OCH_3$ | |
| Q-4 | N | — | 6-Cl | H | H | $CH_3$ | $OCH_3$ | |

TABLE 2-continued $$QSO_2NHCNH-\underset{\underset{Y}{\underset{\|}{N}}}{\overset{\overset{X}{\underset{\|}{N}}}{\bigcirc}}$$

| Q | W | R | $R_1$ | $R_2$ | $R_3$ | X | Y | m.p. (°C.) |
|---|---|---|---|---|---|---|---|---|
| Q-4 | N | — | 5-Br | H | H | $CH_3$ | $OCH_3$ | |
| Q-4 | N | — | 6-$CH_3$ | H | H | $CH_3$ | $OCH_3$ | |
| Q-4 | N | — | 5-$OCH_3$ | H | H | $CH_3$ | $OCH_3$ | |
| Q-4 | N | — | 6-$OCF_2H$ | H | H | $CH_3$ | $OCH_3$ | |
| Q-1 | S | $CH_3$ | H | — | — | $CH_3$ | $CH(OCH_2CH_3)_2$ | |
| Q-1 | S | $CH_3$ | H | — | — | $CH_3$ | $CH(OCH_3)SCH_2CH_3$ | |
| Q-1 | S | $CH_3$ | H | — | — | $CH_3$ | $CH(OCH_2CH_3)SCH_2CH_3$ | |
| Q-1 | S | $CH_3$ | H | — | — | $CH_3$ | $CH(SCH_3)_2$ | |
| Q-1 | S | $CH_3$ | H | — | — | $CH_3$ | $CH(SCH_2CH_3)_2$ | |
| Q-1 | S | $CH_3$ | H | — | — | $CH_3$ | $CH(SCH_2CH_3)SCH_3$ | |
| Q-1 | S | $CH_3$ | H | — | — | $CH_3$ | $C(OCH_2CH_3)_2CH_3$ | |
| Q-1 | S | $CH_3$ | H | — | — | $CH_3$ | $C(OCH_3)(OCH_2CH_3)CH_3$ | |
| Q-1 | S | $CH_3$ | H | — | — | $CH_3$ | $C(OCH_3)(SCH_2CH_3)CH_3$ | |
| Q-1 | S | $CH_3$ | H | — | — | $CH_3$ | $C(OCH_2CH_3)(SCH_3)CH_3$ | |
| Q-1 | S | $CH_3$ | H | — | — | $CH_3$ | $C(OCH_2CH_3)(SCH_2CH_3)CH_3$ | |
| Q-1 | S | $CH_3$ | H | — | — | $CH_3$ | $C(SCH_3)_2CH_3$ | |
| Q-1 | S | $CH_3$ | H | — | — | $CH_3$ | $C(SCH_2CH_3)_2CH_3$ | |
| Q-1 | S | $CH_3$ | H | — | — | $CH_3$ | $C(SCH_2CH_3)(SCH_3)CH_3$ | |
| Q-1 | S | $CH_3$ | H | — | — | $CH_3$ | 2-methyl-1,3-dioxolane (C(CH_3)(O-CH_2-CH_2-O)) | |
| Q-1 | S | $CH_3$ | H | — | — | $CH_3$ | 2-methyl-1,3-oxathiolane (C(CH_3)(O-CH_2-CH_2-S)) | |
| Q-1 | S | $CH_3$ | H | — | — | $CH_3$ | 1,3-dithiolan-2-yl (CH(S-CH_2-CH_2-S)) | |
| Q-1 | S | $CH_3$ | H | — | — | $CH_3$ | 2-methyl-1,3-dithiolane (C(CH_3)(S-CH_2-CH_2-S)) | |
| Q-1 | S | $CH_3$ | H | — | — | $CH_3$ | 1,3-dioxan-2-yl (CH(O-CH_2-CH_2-CH_2-O)) | |
| Q-1 | S | $CH_3$ | H | — | — | $CH_3$ | 1,3-oxathian-2-yl (CH(O-CH_2-CH_2-CH_2-S)) | |
| Q-1 | S | $CH_3$ | H | — | — | $CH_3$ | 2-methyl-1,3-oxathiolane variant (C(CH_3)(O-CH_2-CH_2-S)) | |
| Q-1 | S | $CH_3$ | H | — | — | $CH_3$ | 2,4-dimethyl-1,3-dioxolane (C(CH_3)(O-CH(CH_3)-CH_2-O)) | |

TABLE 2-continued

QSO₂NHCNH— [pyrimidine/triazine ring with X and Y substituents]

| Q | W | R | R₁ | R₂ | R₃ | X | Y | m.p. (°C.) |
|---|---|---|---|---|---|---|---|---|
| Q-1 | S | CH₃ | H | — | — | CH₃ | 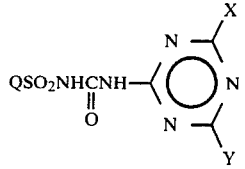 | |
| Q-1 | S | CH₃ | H | — | — | CH₃ | 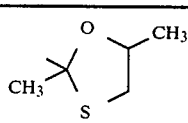 | |
| Q-1 | S | CH₃ | H | — | — | CH₃ | C≡CH | |
| Q-1 | S | CH₃ | H | — | — | CH₃ | C≡CCH₃ | |
| Q-1 | S | CH₃ | H | — | — | OCH₃ | CH₂OCH₃ | |
| Q-1 | S | CH₃ | H | — | — | OCH₃ | NHCH₃ | |
| Q-1 | S | CH₃ | H | — | — | OCH₃ | CH₂CH₃ | |
| Q-1 | S | CH₃ | H | — | — | OCH₃ | CH(OCH₃)₂ | |
| Q-1 | S | CH₃ | H | — | — | OCH₃ | 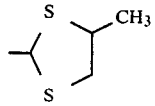 | |
| Q-1 | S | CH₃ | H | — | — | OCH₃ | C≡CH | |
| Q-1 | S | CH₃ | H | — | — | OCH₃ | C≡CCH₃ | |
| Q-1 | S | CH₃ | 5-CF₃ | — | — | CH₃ | OCH₃ | |
| Q-1 | S | CH₃ | 6-CH₂OCH₃ | — | — | CH₃ | OCH₃ | |
| Q-1 | S | CH₃ | 5-CH₂SCH₃ | — | — | CH₃ | OCH₃ | |
| Q-1 | S | H | 5-F | — | — | CH₃ | OCH₃ | |
| Q-1 | S | H | 6-Cl | — | — | CH₃ | OCH₃ | |
| Q-1 | S | H | 5-Br | — | — | CH₃ | OCH₃ | |
| Q-1 | S | H | 6-CH₃ | — | — | CH₃ | OCH₃ | |
| Q-1 | S | H | 5-OCH₃ | — | — | CH₃ | OCH₃ | |
| Q-1 | S | H | 6-OCF₂H | — | — | CH₃ | OCH₃ | |
| Q-1 | S | H | 5-CF₃ | — | — | CH₃ | OCH₃ | |
| Q-1 | S | H | 6-CH₂OCH₃ | — | — | CH₃ | OCH₃ | |
| Q-1 | S | H | 5-CH₂SCH₃ | — | — | CH₃ | OCH₃ | |
| Q-1 | S | CH₂CH₃ | 5-F | — | — | CH₃ | OCH₃ | |
| Q-1 | S | CH₂CH₃ | 6-Cl | — | — | CH₃ | OCH₃ | |
| Q-1 | S | CH₂CH₃ | 5-Br | — | — | CH₃ | OCH₃ | |
| Q-1 | S | CH₂CH₃ | 6-CH₃ | — | — | CH₃ | OCH₃ | |
| Q-1 | S | CH₂CH₃ | 5-OCH₃ | — | — | CH₃ | OCH₃ | |
| Q-1 | S | CH₂CH₃ | 6-OCF₂H | — | — | CH₃ | OCH₃ | |
| Q-1 | S | CH₂CH₃ | 5-CF₃ | — | — | CH₃ | OCH₃ | |
| Q-1 | S | CH₂CH₃ | 6-CH₂OCH₃ | — | — | CH₃ | OCH₃ | |
| Q-1 | S | CH₂CH₃ | 5-CH₂SCH₃ | — | — | CH₃ | OCH₃ | |
| Q-1 | O | H | 5-F | — | — | OCH₃ | OCH₃ | |
| Q-1 | O | H | 6-Cl | — | — | OCH₃ | OCH₃ | |
| Q-1 | O | H | 5-Br | — | — | OCH₃ | OCH₃ | |
| Q-1 | O | H | 6-CH₃ | — | — | OCH₃ | OCH₃ | |
| Q-1 | O | H | 5-OCH₃ | — | — | OCH₃ | OCH₃ | |
| Q-1 | O | H | 6-OCF₂H | — | — | OCH₃ | OCH₃ | |
| Q-1 | O | H | 5-CF₃ | — | — | OCH₃ | OCH₃ | |
| Q-1 | O | H | 6-CH₂OCH₃ | — | — | OCH₃ | OCH₃ | |
| Q-1 | O | H | 5-CH₂SCH₃ | — | — | OCH₃ | OCH₃ | |
| Q-1 | O | CH₃ | H | — | — | OCH₃ | OCH₃ | |
| Q-1 | O | CH₃ | 5-CF₃ | — | — | OCH₃ | OCH₃ | |
| Q-1 | O | CH₃ | 6-CH₂OCH₃ | — | — | OCH₃ | OCH₃ | |
| Q-1 | O | CH₃ | 5-CH₂SCH₃ | — | — | OCH₃ | OCH₃ | |
| Q-1 | O | CH₂CH₃ | 5-F | — | — | OCH₃ | OCH₃ | |
| Q-1 | O | CH₂CH₃ | 6-Cl | — | — | OCH₃ | OCH₃ | |
| Q-1 | O | CH₂CH₃ | 5-Br | — | — | OCH₃ | OCH₃ | |
| Q-1 | O | CH₂CH₃ | 6-CH₃ | — | — | OCH₃ | OCH₃ | |
| Q-1 | O | CH₂CH₃ | 5-OCH₃ | — | — | OCH₃ | OCH₃ | |
| Q-1 | O | CH₂CH₃ | 6-OCF₂H | — | — | OCH₃ | OCH₃ | |
| Q-1 | O | CH₂CH₃ | 5-CF₃ | — | — | OCH₃ | OCH₃ | |
| Q-1 | O | CH₂CH₃ | 5-CH₂OCH₃ | — | — | OCH₃ | OCH₃ | |
| Q-1 | O | CH₂CH₃ | 6-CH₂SCH₃ | — | — | OCH₃ | OCH₃ | |
| Q-1 | N | H | H | — | H | OCH₃ | OCH₃ | |
| Q-1 | N | H | 5-F | — | H | OCH₃ | OCH₃ | |
| Q-1 | N | H | 6-Cl | — | H | OCH₃ | OCH₃ | |

TABLE 2-continued

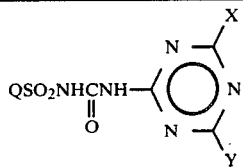

| Q | W | R | R₁ | R₂ | R₃ | X | Y | m.p. (°C.) |
|---|---|---|---|---|---|---|---|---|
| Q-1 | N | H | 5-Br | — | H | OCH₃ | OCH₃ | |
| Q-1 | N | H | 6-CH₃ | — | H | OCH₃ | OCH₃ | |
| Q-1 | N | H | 5-OCH₃ | — | H | OCH₃ | OCH₃ | |
| Q-1 | N | H | 6-OCF₂H | — | H | OCH₃ | OCH₃ | |
| Q-1 | N | H | 5-CF₃ | — | H | OCH₃ | OCH₃ | |
| Q-1 | N | H | 6-CH₂OCH₃ | — | H | OCH₃ | OCH₃ | |
| Q-1 | N | H | 5-CH₂SCH₃ | — | H | OCH₃ | OCH₃ | |
| Q-1 | N | H | 5-F | — | CH₃ | OCH₃ | OCH₃ | |
| Q-1 | N | H | 6-Cl | — | CH₃ | OCH₃ | OCH₃ | |
| Q-1 | N | H | 5-Br | — | CH₃ | OCH₃ | OCH₃ | |
| Q-1 | N | H | 6-CH₃ | — | CH₃ | OCH₃ | OCH₃ | |
| Q-1 | N | H | 5-OCH₃ | — | CH₃ | OCH₃ | OCH₃ | |
| Q-1 | N | H | 6-OCF₂H | — | CH₃ | OCH₃ | OCH₃ | |
| Q-1 | N | H | 5-CF₃ | — | CH₃ | OCH₃ | OCH₃ | |
| Q-1 | N | H | 6-CH₂OCH₃ | — | CH₃ | OCH₃ | OCH₃ | |
| Q-1 | N | H | 5-CH₂SCH₃ | — | CH₃ | OCH₃ | OCH₃ | |
| Q-1 | N | CH₃ | H | — | H | OCH₃ | OCH₃ | |
| Q-1 | N | CH₃ | 5-CF₃ | — | H | OCH₃ | OCH₃ | |
| Q-1 | N | CH₃ | 6-CH₂OCH₃ | — | H | OCH₃ | OCH₃ | |
| Q-1 | N | CH₃ | 5-CH₂SCH₃ | — | H | OCH₃ | OCH₃ | |
| Q-1 | N | CH₃ | H | — | CH₃ | OCH₃ | OCH₃ | |
| Q-1 | N | CH₃ | 5-F | — | CH₃ | OCH₃ | OCH₃ | |
| Q-1 | N | CH₃ | 6-Cl | — | CH₃ | OCH₃ | OCH₃ | |
| Q-1 | N | CH₃ | 5-Br | — | CH₃ | OCH₃ | OCH₃ | |
| Q-1 | N | CH₃ | 6-CH₃ | — | CH₃ | OCH₃ | OCH₃ | |
| Q-1 | N | CH₃ | 5-OCH₃ | — | CH₃ | OCH₃ | OCH₃ | |
| Q-1 | N | CH₃ | 6-OCF₂H | — | CH₃ | OCH₃ | OCH₃ | |
| Q-1 | N | CH₃ | 5-CF₃ | — | CH₃ | OCH₃ | OCH₃ | |
| Q-1 | N | CH₃ | 6-CH₂OCH₃ | — | CH₃ | OCH₃ | OCH₃ | |
| Q-1 | N | CH₃ | 5-CH₂SCH₃ | — | CH₃ | OCH₃ | OCH₃ | |
| Q-1 | N | CH₂CH₃ | 5-F | — | H | OCH₃ | OCH₃ | |
| Q-1 | N | CH₂CH₃ | 6-Cl | — | H | OCH₃ | OCH₃ | |
| Q-1 | N | CH₂CH₃ | 5-Br | — | H | OCH₃ | OCH₃ | |
| Q-1 | N | CH₂CH₃ | 6-CH₃ | — | H | OCH₃ | OCH₃ | |
| Q-1 | N | CH₂CH₃ | 5-OCH₃ | — | H | OCH₃ | OCH₃ | |
| Q-1 | N | CH₂CH₃ | 6-OCF₂H | — | H | OCH₃ | OCH₃ | |
| Q-1 | N | CH₂CH₃ | 5-CF₃ | — | H | OCH₃ | OCH₃ | |
| Q-1 | N | CH₂CH₃ | 6-CH₂OCH₃ | — | H | OCH₃ | OCH₃ | |
| Q-1 | N | CH₂CH₃ | 5-CH₂SCH₃ | — | H | OCH₃ | OCH₃ | |
| Q-1 | N | CH₂CH₃ | H | — | CH₃ | OCH₃ | OCH₃ | |
| Q-1 | N | CH₂CH₃ | 5-F | — | CH₃ | OCH₃ | OCH₃ | |
| Q-1 | N | CH₂CH₃ | 6-Cl | — | CH₃ | OCH₃ | OCH₃ | |
| Q-1 | N | CH₂CH₃ | 5-Br | — | CH₃ | OCH₃ | OCH₃ | |
| Q-1 | N | CH₂CH₃ | 6-CH₃ | — | CH₃ | OCH₃ | OCH₃ | |
| Q-1 | N | CH₂CH₃ | 5-OCH₃ | — | CH₃ | OCH₃ | OCH₃ | |
| Q-1 | N | CH₂CH₃ | 6-OCF₂H | — | CH₃ | OCH₃ | OCH₃ | |
| Q-1 | N | CH₂CH₃ | 5-CF₃ | — | CH₃ | OCH₃ | OCH₃ | |
| Q-1 | N | CH₂CH₃ | 6-CH₂OCH₃ | — | CH₃ | OCH₃ | OCH₃ | |
| Q-1 | N | CH₂CH₃ | 5-CH₂SCH₃ | — | CH₃ | OCH₃ | OCH₃ | |
| Q-2 | S | CH₃ | 5-CF₃ | — | — | CH₃ | OCH₃ | |
| Q-2 | S | CH₃ | 6-CH₂OCH₃ | — | — | CH₃ | OCH₃ | |
| Q-2 | S | CH₃ | 5-CH₂SCH₃ | — | — | CH₃ | OCH₃ | |
| Q-2 | S | H | 5-F | — | — | CH₃ | OCH₃ | |
| Q-2 | S | H | 6-Cl | — | — | CH₃ | OCH₃ | |
| Q-2 | S | H | 5-Br | — | — | CH₃ | OCH₃ | |
| Q-2 | S | H | 6-CH₃ | — | — | CH₃ | OCH₃ | |
| Q-2 | S | H | 5-OCH₃ | — | — | CH₃ | OCH₃ | |
| Q-2 | S | H | 6-OCF₂H | — | — | CH₃ | OCH₃ | |
| Q-2 | S | H | 5-CF₃ | — | — | CH₃ | OCH₃ | |
| Q-2 | S | H | 6-CH₂OCH₃ | — | — | CH₃ | OCH₃ | |
| Q-2 | S | H | 5-CH₂SCH₃ | — | — | CH₃ | OCH₃ | |
| Q-2 | S | CH₂CH₃ | 5-F | — | — | CH₃ | OCH₃ | |
| Q-2 | S | CH₂CH₃ | 6-Cl | — | — | CH₃ | OCH₃ | |
| Q-2 | S | CH₂CH₃ | 5-Br | — | — | CH₃ | OCH₃ | |
| Q-2 | S | CH₂CH₃ | 6-CH₃ | — | — | CH₃ | OCH₃ | |
| Q-2 | S | CH₂CH₃ | 5-OCH₃ | — | — | CH₃ | OCH₃ | |
| Q-2 | S | CH₂CH₃ | 6-OCF₂H | — | — | CH₃ | OCH₃ | |
| Q-2 | S | CH₂CH₃ | 5-CF₃ | — | — | CH₃ | OCH₃ | |
| Q-2 | S | CH₂CH₃ | 6-CH₂OCH₃ | — | — | CH₃ | OCH₃ | |
| Q-2 | S | CH₂CH₃ | 5-CH₂SCH₃ | — | — | CH₃ | OCH₃ | |
| Q-2 | O | CH₃ | 5-CF₃ | — | — | CH₃ | OCH₃ | |
| Q-2 | O | CH₃ | 6-CH₂OCH₃ | — | — | CH₃ | OCH₃ | |

TABLE 2-continued

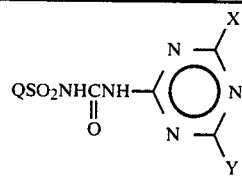

| Q | W | R | R₁ | R₂ | R₃ | X | Y | m.p. (°C.) |
|---|---|---|---|---|---|---|---|---|
| Q-2 | O | CH₃ | 5-CH₂SCH₃ | — | — | CH₃ | OCH₃ | |
| Q-2 | N | H | H | — | H | CH₃ | OCH₃ | |
| Q-2 | N | CH₃ | H | — | H | CH₃ | OCH₃ | |
| Q-2 | N | CH₃ | 5-CF₃ | — | H | CH₃ | OCH₃ | |
| Q-2 | N | CH₃ | 6-CH₂OCH₃ | — | H | CH₃ | OCH₃ | |
| Q-2 | N | CH₃ | 5-CH₂SCH₃ | — | H | CH₃ | OCH₃ | |
| Q-2 | N | CH₃ | 6-F | — | CH₃ | CH₃ | OCH₃ | |
| Q-2 | N | CH₃ | 5-Cl | — | CH₃ | CH₃ | OCH₃ | |
| Q-2 | N | CH₃ | 6-Br | — | CH₃ | CH₃ | OCH₃ | |
| Q-2 | N | CH₃ | 5-CH₃ | — | CH₃ | CH₃ | OCH₃ | |
| Q-2 | N | CH₃ | 6-OCH₃ | — | CH₃ | CH₃ | OCH₃ | |
| Q-2 | N | CH₃ | 5-OCF₂H | — | CH₃ | CH₃ | OCH₃ | |
| Q-2 | N | CH₃ | 6-CF₃ | — | CH₃ | CH₃ | OCH₃ | |
| Q-2 | N | CH₃ | 5-CH₂OCH₃ | — | CH₃ | CH₃ | OCH₃ | |
| Q-2 | N | CH₃ | 6-CH₂SCH₃ | — | CH₃ | CH₃ | OCH₃ | |
| Q-2 | N | CH₂CH₃ | H | — | CH₃ | CH₃ | OCH₃ | |
| Q-3 | S | — | 5-CF₃ | H | — | CH₃ | OCH₃ | |
| Q-3 | S | — | 6-CH₂OCH₃ | H | — | CH₃ | OCH₃ | |
| Q-3 | S | — | 5-CH₂SCH₃ | H | — | CH₃ | OCH₃ | |
| Q-3 | S | — | 5-F | CH₃ | — | CH₃ | OCH₃ | |
| Q-3 | S | — | 6-Cl | CH₃ | — | CH₃ | OCH₃ | |
| Q-3 | S | — | 5-Br | CH₃ | — | CH₃ | OCH₃ | |
| Q-3 | S | — | 6-CH₃ | CH₃ | — | CH₃ | OCH₃ | |
| Q-3 | S | — | 5-OCH₃ | CH₃ | — | CH₃ | OCH₃ | |
| Q-3 | S | — | 6-OCF₂H | CH₃ | — | CH₃ | OCH₃ | |
| Q-3 | S | — | 5-CF₃ | CH₃ | — | CH₃ | OCH₃ | |
| Q-3 | S | — | 6-CH₂OCH₃ | CH₃ | — | CH₃ | OCH₃ | |
| Q-3 | S | — | 5-CH₂SCH₃ | CH₃ | — | CH₃ | OCH₃ | |
| Q-3 | O | — | 6-CF₃ | H | — | CH₃ | OCH₃ | |
| Q-3 | O | — | 5-CH₂OCH₃ | H | — | CH₃ | OCH₃ | |
| Q-3 | O | — | 6-CH₂SCH₃ | H | — | CH₃ | OCH₃ | |
| Q-3 | N | — | 5-CF₃ | H | H | CH₃ | OCH₃ | |
| Q-3 | N | — | 6-CH₂OCH₃ | H | H | CH₃ | OCH₃ | |
| Q-3 | N | — | 5-CH₂SCH₃ | H | H | CH₃ | OCH₃ | |
| Q-3 | N | — | H | H | H | CH₃ | OCH₃ | |
| Q-4 | S | — | 5-CF₃ | H | — | CH₃ | OCH₃ | |
| Q-4 | S | — | 6-CH₂OCH₃ | H | — | CH₃ | OCH₃ | |
| Q-4 | S | — | 5-CH₂SCH₃ | H | — | CH₃ | OCH₃ | |
| Q-4 | S | — | 5-F | CH₃ | — | CH₃ | OCH₃ | |
| Q-4 | S | — | 6-Cl | CH₃ | — | CH₃ | OCH₃ | |
| Q-4 | S | — | 5-Br | CH₃ | — | CH₃ | OCH₃ | |
| Q-4 | S | — | 6-CH₃ | CH₃ | — | CH₃ | OCH₃ | |
| Q-4 | S | — | 5-OCH₃ | CH₃ | — | CH₃ | OCH₃ | |
| Q-4 | S | — | 6-OCF₂H | CH₃ | — | CH₃ | OCH₃ | |
| Q-4 | S | — | 5-CF₃ | CH₃ | — | CH₃ | OCH₃ | |
| Q-4 | S | — | 6-CH₂OCH₃ | CH₃ | — | CH₃ | OCH₃ | |
| Q-4 | S | — | 5-CH₂SCH₃ | CH₃ | — | CH₃ | OCH₃ | |
| Q-4 | O | — | 6-CF₃ | H | — | CH₃ | OCH₃ | |
| Q-4 | O | — | 5-CH₂OCH₃ | H | — | CH₃ | OCH₃ | |
| Q-4 | O | — | 6-CH₂SCH₃ | H | — | CH₃ | OCH₃ | |
| Q-4 | N | — | H | H | H | CH₃ | OCH₃ | |
| Q-4 | N | — | 5-CF₃ | H | H | CH₃ | OCH₃ | |
| Q-4 | N | — | 6-CH₂OCH₃ | H | H | CH₃ | OCH₃ | |
| Q-4 | N | — | 5-CH₂SCH₃ | H | H | CH₃ | OCH₃ | |

TABLE 3

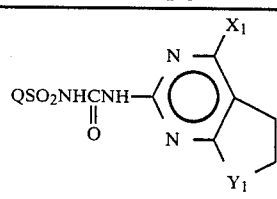

| Q | W | R | R₁ | R₂ | R₃ | X₁ | Y₁ | m.p. (°C.) |
|---|---|---|---|---|---|---|---|---|
| Q-1 | S | H | H | — | — | CH₃ | O | |
| Q-1 | S | CH₃ | 5-F | — | — | CH₃ | O | |

TABLE 3-continued

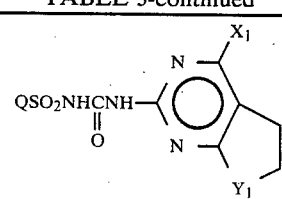

| Q | W | R | R₁ | R₂ | R₃ | X₁ | Y₁ | m.p. (°C.) |
|---|---|---|---|---|---|---|---|---|
| Q-1 | S | CH₃ | 6-Cl | — | — | CH₃ | O | |
| Q-1 | S | CH₃ | 5-Br | — | — | CH₃ | O | |

TABLE 3-continued

QSO₂NHCNH— [pyrimidine ring with $X_1$, $Y_1$, and fused ring]
        ‖
        O

| Q | W | R | R₁ | R₂ | R₃ | X₁ | Y₁ | m.p. (°C.) |
|---|---|---|----|----|----|----|----|----|
| Q-1 | S | CH₃ | 6-CH₃ | — | — | CH₃ | CH₂ | |
| Q-1 | S | CH₃ | 5-OCH₃ | — | — | CH₃ | CH₂ | |
| Q-1 | S | CH₃ | 6-OCF₂H | — | — | CH₃ | CH₂ | |
| Q-1 | S | C₂H₅ | H | — | — | CH₃ | O | |
| Q-1 | S | i-C₃H₇ | H | — | — | CH₃ | O | |
| Q-1 | S | t-C₄H₉ | H | — | — | CH₃ | CH₂ | |
| Q-1 | S | CH₃ | H | — | — | OCH₃ | O | |
| Q-1 | S | CH₃ | H | — | — | OCH₂CH₃ | O | |
| Q-1 | S | CH₃ | H | — | — | OCF₂H | O | |
| Q-1 | O | H | H | — | — | OCH₃ | O | |
| Q-1 | O | CH₃ | 5-F | — | — | OCH₃ | O | |
| Q-1 | O | CH₃ | 6-Cl | — | — | OCH₃ | O | |
| Q-1 | O | CH₃ | 5-Br | — | — | OCH₃ | O | |
| Q-1 | O | CH₃ | 6-CH₃ | — | — | OCH₃ | CH₂ | |
| Q-1 | O | CH₃ | 5-OCH₃ | — | — | OCH₃ | CH₂ | |
| Q-1 | O | CH₃ | 6-OCF₂H | — | — | OCH₃ | CH₂ | |
| Q-1 | O | C₂H₅ | H | — | — | OCH₃ | CH₂ | |
| Q-1 | O | i-C₃H₇ | H | — | — | OCH₃ | O | |
| Q-1 | O | t-C₄H₉ | H | — | — | OCH₃ | O | |
| Q-1 | N | H | H | — | CH₃ | CH₃ | O | |
| Q-1 | N | CH₃ | 5-F | — | H | CH₃ | O | |
| Q-1 | N | CH₃ | 6-Cl | — | H | CH₃ | O | |
| Q-1 | N | CH₃ | 5-Br | — | H | CH₃ | O | |
| Q-1 | N | CH₃ | 6-CH₃ | — | H | CH₃ | O | |
| Q-1 | N | CH₃ | 5-OCH₃ | — | H | CH₃ | O | |
| Q-1 | N | CH₃ | 6-OCF₂H | — | H | CH₃ | O | |
| Q-1 | N | C₂H₅ | H | — | H | CH₃ | CH₂ | |
| Q-1 | N | i-C₃H₇ | H | — | H | CH₃ | CH₂ | |
| Q-1 | N | t-C₄H₉ | H | — | H | CH₃ | CH₂ | |
| Q-2 | S | H | H | — | — | CH₃ | CH₂ | |
| Q-2 | S | CH₃ | 5-F | — | — | CH₃ | CH₂ | |
| Q-2 | S | CH₃ | 6-Cl | — | — | CH₃ | CH₂ | |
| Q-2 | S | CH₃ | 5-Br | — | — | CH₃ | CH₂ | |
| Q-2 | S | CH₃ | 6-CH₃ | — | — | CH₃ | CH₂ | |
| Q-2 | S | CH₃ | 5-OCH₃ | — | — | CH₃ | CH₂ | |
| Q-2 | S | CH₃ | 6-OCF₂H | — | — | CH₃ | O | |
| Q-2 | S | C₂H₅ | H | — | — | CH₃ | O | |
| Q-2 | S | i-C₃H₇ | H | — | — | CH₃ | O | |
| Q-2 | S | t-C₄H₉ | H | — | — | CH₃ | O | |
| Q-2 | O | H | H | — | — | CH₃ | O | |
| Q-2 | O | CH₃ | 5-F | — | — | CH₃ | O | |
| Q-2 | O | CH₃ | 6-Cl | — | — | CH₃ | O | |
| Q-2 | O | CH₃ | 5-Br | — | — | CH₃ | O | |
| Q-2 | O | CH₃ | 6-CH₃ | — | — | CH₃ | O | |
| Q-2 | O | CH₃ | 5-OCH₃ | — | — | CH₃ | O | |
| Q-2 | O | CH₃ | 6-OCF₂H | — | — | CH₃ | O | |
| Q-2 | O | C₂H₅ | H | — | — | CH₃ | CH₂ | |
| Q-2 | O | i-C₃H₇ | H | — | — | CH₃ | CH₂ | |
| Q-2 | O | t-C₄H₉ | H | — | — | CH₃ | CH₂ | |
| Q-2 | N | H | H | — | CH₃ | CH₃ | CH₂ | |
| Q-2 | N | CH₃ | 5-F | — | H | CH₃ | CH₂ | |
| Q-2 | N | CH₃ | 6-Cl | — | H | CH₃ | CH₂ | |
| Q-2 | N | CH₃ | 5-Br | — | H | CH₃ | CH₂ | |
| Q-2 | N | CH₃ | 6-CH₃ | — | H | CH₃ | CH₂ | |
| Q-2 | N | CH₃ | 5-OCH₃ | — | H | CH₃ | CH₂ | |
| Q-2 | N | CH₃ | 6-OCF₂H | — | H | CH₃ | CH₂ | |
| Q-2 | N | C₂H₅ | H | — | H | CH₃ | O | |
| Q-2 | N | i-C₃H₇ | H | — | H | CH₃ | O | |
| Q-2 | N | t-C₄H₉ | H | — | H | CH₃ | O | |
| Q-3 | S | — | H | H | — | CH₃ | O | |
| Q-3 | S | — | H | CH₃ | — | CH₃ | O | |
| Q-3 | S | — | 5-F | H | — | CH₃ | O | |
| Q-3 | S | — | 6-Cl | H | — | CH₃ | O | |
| Q-3 | S | — | 5-Br | H | — | CH₃ | O | |
| Q-3 | S | — | 6-CH₃ | H | — | CH₃ | CH₂ | |
| Q-3 | S | — | 5-OCH₃ | H | — | CH₃ | CH₂ | |
| Q-3 | S | — | 6-OCF₂H | H | — | CH₃ | CH₂ | |
| Q-3 | O | — | H | H | — | CH₃ | CH₂ | |
| Q-3 | O | — | H | CH₃ | — | CH₃ | CH₂ | |
| Q-3 | O | — | 5-F | H | — | CH₃ | CH₂ | |
| Q-3 | O | — | 6-Cl | H | — | CH₃ | CH₂ | |
| Q-3 | O | — | 5-Br | H | — | CH₃ | O | |
| Q-3 | O | — | 6-CH₃ | H | — | CH₃ | O | |
| Q-3 | O | — | 5-OCH₃ | H | — | CH₃ | O | |
| Q-3 | O | — | 6-OCF₂H | H | — | CH₃ | O | |
| Q-3 | N | — | H | H | CH₃ | CH₃ | O | |
| Q-3 | N | — | H | CH₃ | H | CH₃ | O | |
| Q-3 | N | — | 5-F | H | H | CH₃ | O | |
| Q-3 | N | — | 6-Cl | H | H | CH₃ | O | |
| Q-3 | N | — | 5-Br | H | H | CH₃ | O | |
| Q-3 | N | — | 6-CH₃ | H | H | CH₃ | CH₂ | |
| Q-3 | N | — | 5-OCH₃ | H | H | CH₃ | CH₂ | |
| Q-3 | N | — | 6-OCF₂H | H | H | CH₃ | CH₂ | |
| Q-4 | S | — | H | H | — | CH₃ | CH₂ | |
| Q-4 | S | — | H | CH₃ | — | CH₃ | CH₂ | |
| Q-4 | S | — | 5-F | H | — | CH₃ | CH₂ | |
| Q-4 | S | — | 6-Cl | H | — | CH₃ | CH₂ | |
| Q-4 | S | — | 5-Br | H | — | CH₃ | CH₂ | |
| Q-4 | S | — | 6-CH₃ | H | — | CH₃ | O | |
| Q-4 | S | — | 5-OCH₃ | H | — | CH₃ | O | |
| Q-4 | S | — | 6-OCF₂H | H | — | CH₃ | O | |
| Q-4 | O | — | H | H | — | CH₃ | O | |
| Q-4 | O | — | H | CH₃ | — | CH₃ | O | |
| Q-4 | O | — | 5-F | H | — | CH₃ | O | |
| Q-4 | O | — | 6-Cl | H | — | CH₃ | O | |
| Q-4 | O | — | 5-Br | H | — | CH₃ | CH₂ | |
| Q-4 | O | — | 6-CH₃ | H | — | CH₃ | CH₂ | |
| Q-4 | O | — | 5-OCH₃ | H | — | CH₃ | CH₂ | |
| Q-4 | O | — | 6-OCF₂H | H | — | CH₃ | CH₂ | |
| Q-4 | N | — | H | H | CH₃ | CH₃ | CH₂ | |
| Q-4 | N | — | H | CH₃ | H | CH₃ | CH₂ | |
| Q-4 | N | — | 5-F | H | H | CH₃ | CH₂ | |
| Q-4 | N | — | 6-Cl | H | H | CH₃ | O | |
| Q-4 | N | — | 5-Br | H | H | CH₃ | O | |
| Q-4 | N | — | 6-CH₃ | H | H | CH₃ | O | |
| Q-4 | N | — | 5-OCH₃ | H | H | CH₃ | O | |
| Q-4 | N | — | 6-OCF₂H | H | H | CH₃ | O | |
| Q-1 | S | CH₃ | 5-CF₃ | — | — | CH₃ | CH₂ | |
| Q-1 | S | CH₃ | 6-CH₂OCH₃ | — | — | CH₃ | CH₂ | |
| Q-1 | S | CH₃ | 5-CH₂SCH₃ | — | — | CH₃ | CH₂ | |
| Q-1 | O | CH₃ | 5-CF₃ | — | — | OCH₃ | CH₂ | |
| Q-1 | O | CH₃ | 6-CH₂OCH₃ | — | — | OCH₃ | CH₂ | |
| Q-1 | O | CH₃ | 5-CH₂SCH₃ | — | — | OCH₃ | CH₂ | |
| Q-1 | N | CH₃ | 5-CF₃ | — | H | CH₃ | O | |
| Q-1 | N | CH₃ | 6-CH₂OCH₃ | — | H | CH₃ | O | |
| Q-1 | N | CH₃ | 5-CH₂SCH₃ | — | H | CH₃ | O | |
| Q-1 | S | H | 5-F | — | — | CH₃ | O | |
| Q-1 | S | H | 6-Cl | — | — | CH₃ | O | |
| Q-1 | S | H | 5-Br | — | — | CH₃ | O | |
| Q-1 | S | H | 6-CH₃ | — | — | CH₃ | O | |
| Q-1 | S | H | 5-OCH₃ | — | — | CH₃ | O | |
| Q-1 | S | H | 6-OCF₂H | — | — | CH₃ | O | |
| Q-1 | S | H | 5-CF₃ | — | — | CH₃ | O | |
| Q-1 | S | H | 6-CH₂OCH₃ | — | — | CH₃ | O | |
| Q-1 | S | H | 5-CH₂SCH₃ | — | — | CH₃ | O | |
| Q-2 | S | CH₃ | H | — | — | CH₃ | CH₂ | |
| Q-2 | S | CH₃ | 5-CF₃ | — | — | CH₃ | CH₂ | |
| Q-2 | S | CH₃ | 6-CH₂OCH₃ | — | — | CH₃ | CH₂ | |
| Q-2 | S | CH₃ | 5-CH₂SCH₃ | — | — | CH₃ | CH₂ | |
| Q-2 | O | CH₃ | H | — | — | CH₃ | O | |
| Q-2 | O | CH₃ | 5-CF₃ | — | — | CH₃ | O | |
| Q-2 | O | CH₃ | 6-CH₂OCH₃ | — | — | CH₃ | O | |
| Q-2 | O | CH₃ | 5-CH₂SCH₃ | — | — | CH₃ | O | |
| Q-2 | N | CH₃ | H | — | H | CH₃ | CH₂ | |
| Q-2 | N | CH₃ | 5-CF₃ | — | H | CH₃ | CH₂ | |
| Q-2 | N | CH₃ | 6-CH₂OCH₃ | — | H | CH₃ | CH₂ | |
| Q-2 | N | CH₃ | 5-CH₂SCH₃ | — | H | CH₃ | CH₂ | |
| Q-3 | S | — | 5-CF₃ | H | — | CH₃ | CH₂ | |
| Q-3 | S | — | 6-CH₂OCH₃ | H | — | CH₃ | CH₂ | |
| Q-3 | S | — | 5-CH₂SCH₃ | H | — | CH₃ | CH₂ | |

TABLE 3-continued

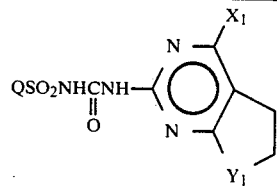

| Q | W | R | R1 | R2 | R3 | X1 | m.p. (°C.) Y1 |
|---|---|---|---|---|---|---|---|
| Q-3 | S | — | 5-CF3 | H | — | CH3 | O |
| Q-3 | S | — | 6-CH2OCH3 | H | — | CH3 | O |
| Q-3 | S | — | 5-CH2SCH3 | H | — | CH3 | O |
| Q-3 | N | — | H | H | H | CH3 | CH2 |
| Q-3 | N | — | 5-CF3 | H | H | CH3 | CH2 |
| Q-3 | N | — | 6-CH2OCH3 | H | H | CH3 | CH2 |
| Q-3 | N | — | 5-CH2SCH3 | H | H | CH3 | CH2 |
| Q-4 | S | — | 5-CF3 | H | — | CH3 | O |
| Q-4 | S | — | 6-CH2OCH3 | H | — | CH3 | O |
| Q-4 | S | — | 5-CH2SCH3 | H | — | CH3 | O |
| Q-4 | O | — | 5-CF3 | H | — | CH3 | CH2 |
| Q-4 | O | — | 6-CH2OCH3 | H | — | CH3 | CH2 |
| Q-4 | O | — | 5-CH2SCH3 | H | — | CH3 | CH2 |
| Q-4 | N | — | 5-CF3 | H | H | CH3 | O |
| Q-4 | N | — | 6-CH2OCH3 | H | H | CH3 | O |
| Q-4 | N | — | 5-CH2SCH3 | H | H | CH3 | O |

TABLE 4

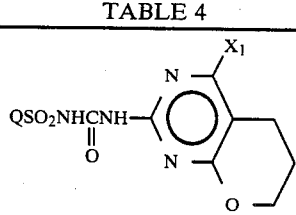

| Q | W | R | R1 | R2 | R3 | X1 | m.p. (°C.) |
|---|---|---|---|---|---|---|---|
| Q-1 | S | H | H | — | — | CH3 | |
| Q-1 | S | CH3 | 5-F | — | — | CH3 | |
| Q-1 | S | CH3 | 6-Cl | — | — | CH3 | |
| Q-1 | S | CH3 | 5-Br | — | — | CH3 | |
| Q-1 | S | CH3 | 6-CH3 | — | — | CH3 | |
| Q-1 | S | CH3 | 5-OCH3 | — | — | CH3 | |
| Q-1 | S | CH3 | 6-OCF2H | — | — | CH3 | |
| Q-1 | S | C2H5 | H | — | — | CH3 | |
| Q-1 | S | i-C3H7 | H | — | — | CH3 | |
| Q-1 | S | t-C4H9 | H | — | — | CH3 | |
| Q-1 | S | CH3 | H | — | — | OCH3 | |
| Q-1 | S | CH3 | H | — | — | OCH2CH3 | |
| Q-1 | S | CH3 | H | — | — | OCF2H | |
| Q-1 | O | H | H | — | — | OCH3 | |
| Q-1 | O | CH3 | 5-F | — | — | OCH3 | |
| Q-1 | O | CH3 | 6-Cl | — | — | OCH3 | |
| Q-1 | O | CH3 | 5-Br | — | — | OCH3 | |
| Q-1 | O | CH3 | 6-CH3 | — | — | OCH3 | |
| Q-1 | O | CH3 | 5-OCH3 | — | — | OCH3 | |
| Q-1 | O | CH3 | 6-OCF2H | — | — | OCH3 | |
| Q-1 | O | C2H5 | H | — | — | OCH3 | |
| Q-1 | O | i-C3H7 | H | — | — | OCH3 | |
| Q-1 | O | t-C4H9 | H | — | — | OCH3 | |
| Q-1 | N | H | H | — | CH3 | CH3 | |
| Q-1 | N | CH3 | 5-F | — | H | CH3 | |
| Q-1 | N | CH3 | 6-Cl | — | H | CH3 | |
| Q-1 | N | CH3 | 5-Br | — | H | CH3 | |
| Q-1 | N | CH3 | 6-CH3 | — | H | CH3 | |
| Q-1 | N | CH3 | 5-OCH3 | — | H | CH3 | |
| Q-1 | N | CH3 | 6-OCF2H | — | H | CH3 | |
| Q-1 | N | C2H5 | H | — | H | CH3 | |
| Q-1 | N | i-C3H7 | H | — | H | CH3 | |
| Q-1 | N | t-C4H9 | H | — | H | CH3 | |
| Q-2 | S | H | H | — | — | CH3 | |
| Q-2 | S | CH3 | 5-F | — | — | CH3 | |
| Q-2 | S | CH3 | 6-Cl | — | — | CH3 | |
| Q-2 | S | CH3 | 5-Br | — | — | CH3 | |
| Q-2 | S | CH3 | 6-CH3 | — | — | CH3 | |

TABLE 4-continued

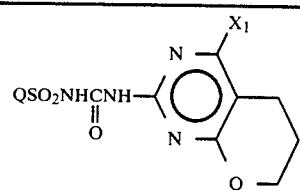

| Q | W | R | R1 | R2 | R3 | X1 | m.p. (°C.) |
|---|---|---|---|---|---|---|---|
| Q-2 | S | CH3 | 5-OCH3 | — | — | CH3 | |
| Q-2 | S | CH3 | 6-OCF2H | — | — | CH3 | |
| Q-2 | S | C2H5 | H | — | — | CH3 | |
| Q-2 | S | i-C3H7 | H | — | — | CH3 | |
| Q-2 | S | t-C4H9 | H | — | — | CH3 | |
| Q-2 | O | H | H | — | — | CH3 | |
| Q-2 | O | CH3 | 5-F | — | — | CH3 | |
| Q-2 | O | CH3 | 6-Cl | — | — | CH3 | |
| Q-2 | O | CH3 | 5-Br | — | — | CH3 | |
| Q-2 | O | CH3 | 6-CH3 | — | — | CH3 | |
| Q-2 | O | CH3 | 5-OCH3 | — | — | CH3 | |
| Q-2 | O | CH3 | 6-OCF2H | — | — | CH3 | |
| Q-2 | O | C2H5 | H | — | — | CH3 | |
| Q-2 | O | i-C3H7 | H | — | — | CH3 | |
| Q-2 | O | t-C4H9 | H | — | — | CH3 | |
| Q-2 | N | H | H | — | CH3 | CH3 | |
| Q-2 | N | CH3 | 5-F | — | H | CH3 | |
| Q-2 | N | CH3 | 6-Cl | — | H | CH3 | |
| Q-2 | N | CH3 | 5-Br | — | H | CH3 | |
| Q-2 | N | CH3 | 6-CH3 | — | H | CH3 | |
| Q-2 | N | CH3 | 5-OCH3 | — | H | CH3 | |
| Q-2 | N | CH3 | 6-OCF2H | — | H | CH3 | |
| Q-2 | N | C2H5 | H | — | H | CH3 | |
| Q-2 | N | i-C3H7 | H | — | H | CH3 | |
| Q-2 | N | t-C4H9 | H | — | H | CH3 | |
| Q-3 | S | — | H | H | — | CH3 | |
| Q-3 | S | — | H | CH3 | — | CH3 | |
| Q-3 | S | — | 5-F | H | — | CH3 | |
| Q-3 | S | — | 6-Cl | H | — | CH3 | |
| Q-3 | S | — | 5-Br | H | — | CH3 | |
| Q-3 | S | — | 6-CH3 | H | — | CH3 | |
| Q-3 | S | — | 5-OCH3 | H | — | CH3 | |
| Q-3 | S | — | 6-OCF2H | H | — | CH3 | |
| Q-3 | O | — | H | H | — | CH3 | |
| Q-3 | O | — | H | CH3 | — | CH3 | |
| Q-3 | O | — | 5-F | H | — | CH3 | |
| Q-3 | O | — | 6-Cl | H | — | CH3 | |
| Q-3 | O | — | 5-Br | H | — | CH3 | |
| Q-3 | O | — | 6-CH3 | H | — | CH3 | |
| Q-3 | O | — | 5-OCH3 | H | — | CH3 | |
| Q-3 | O | — | 6-OCF2H | H | — | CH3 | |
| Q-3 | N | — | H | H | CH3 | CH3 | |
| Q-3 | N | — | H | CH3 | H | CH3 | |
| Q-3 | N | — | 5-F | H | H | CH3 | |
| Q-3 | N | — | 6-Cl | H | H | CH3 | |
| Q-3 | N | — | 5-Br | H | H | CH3 | |
| Q-3 | N | — | 6-CH3 | H | H | CH3 | |
| Q-3 | N | — | 5-OCH3 | H | H | CH3 | |
| Q-3 | N | — | 6-OCF2H | H | H | CH3 | |
| Q-4 | S | — | H | H | — | CH3 | |
| Q-4 | S | — | H | CH3 | — | CH3 | |
| Q-4 | S | — | 5-F | H | — | CH3 | |
| Q-4 | S | — | 6-Cl | H | — | CH3 | |
| Q-4 | S | — | 5-Br | H | — | CH3 | |
| Q-4 | S | — | 6-CH3 | H | — | CH3 | |
| Q-4 | S | — | 5-OCH3 | H | — | CH3 | |
| Q-4 | S | — | 6-OCF2H | H | — | CH3 | |
| Q-4 | O | — | H | H | — | CH3 | |
| Q-4 | O | — | H | CH3 | — | CH3 | |
| Q-4 | O | — | 5-F | H | — | CH3 | |
| Q-4 | O | — | 6-Cl | H | — | CH3 | |
| Q-4 | O | — | 5-Br | H | — | CH3 | |
| Q-4 | O | — | 6-CH3 | H | — | CH3 | |
| Q-4 | O | — | 5-OCH3 | H | — | CH3 | |
| Q-4 | O | — | 6-OCF2H | H | — | CH3 | |
| Q-4 | N | — | H | H | CH3 | CH3 | |
| Q-4 | N | — | H | CH3 | H | CH3 | |
| Q-4 | N | — | 5-F | H | H | CH3 | |
| Q-4 | N | — | 6-Cl | H | H | CH3 | |
| Q-4 | N | — | 5-Br | H | H | CH3 | |

TABLE 4-continued

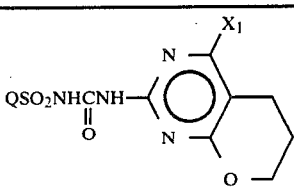

| Q | W | R | R₁ | R₂ | R₃ | X₁ | m.p. (°C.) |
|---|---|---|----|----|----|----|------|
| Q-4 | N | — | 6-CH₃ | H | H | CH₃ | |
| Q-4 | N | — | 5-OCH₃ | H | H | CH₃ | |
| Q-4 | N | — | 6-OCF₂H | H | H | CH₃ | |
| Q-1 | S | CH₃ | H | — | — | CH₃ | |
| Q-1 | S | CH₃ | 5-CF₃ | — | — | CH₃ | |
| Q-1 | S | CH₃ | 6-CH₂OCH₃ | — | — | CH₃ | |
| Q-1 | S | CH₃ | 5-CH₂SCH₃ | — | — | CH₃ | |
| Q-1 | O | CH₃ | H | — | — | OCH₃ | |
| Q-1 | O | CH₃ | 5-CF₃ | — | — | OCH₃ | |
| Q-1 | O | CH₃ | 6-CH₂OCH₃ | — | — | OCH₃ | |
| Q-1 | O | CH₃ | 5-CH₂SCH₃ | — | — | OCH₃ | |
| Q-1 | N | CH₃ | 5-CF₃ | — | H | CH₃ | |
| Q-1 | N | CH₃ | 6-CH₂OCH₃ | — | H | CH₃ | |
| Q-1 | N | CH₃ | 5-CH₂SCH₃ | — | H | CH₃ | |
| Q-2 | S | CH₃ | H | — | — | CH₃ | |
| Q-2 | S | CH₃ | 5-CF₃ | — | — | CH₃ | |
| Q-2 | S | CH₃ | 6-CH₂OCH₃ | — | — | CH₃ | |
| Q-2 | S | CH₃ | 5-CH₂SCH₃ | — | — | CH₃ | |
| Q-2 | O | CH₃ | H | — | — | CH₃ | |
| Q-2 | O | CH₃ | 5-CF₃ | — | — | CH₃ | |
| Q-2 | O | CH₃ | 6-CH₂OCH₃ | — | — | CH₃ | |
| Q-2 | O | CH₃ | 5-CH₂SCH₃ | — | — | CH₃ | |
| Q-2 | N | CH₃ | H | — | H | CH₃ | |
| Q-2 | N | CH₃ | 5-CF₃ | — | H | CH₃ | |
| Q-2 | N | CH₃ | 6-CH₂OCH₃ | — | H | CH₃ | |
| Q-2 | N | CH₃ | 5-CH₂SCH₃ | — | H | CH₃ | |
| Q-3 | S | — | 5-CF₃ | H | — | CH₃ | |
| Q-3 | S | — | 6-CH₂OCH₃ | H | — | CH₃ | |
| Q-3 | S | — | 5-CH₂SCH₃ | H | — | CH₃ | |
| Q-3 | O | — | 5-CF₃ | H | — | CH₃ | |
| Q-3 | O | — | 6-CH₂OCH₃ | H | — | CH₃ | |
| Q-3 | O | — | 5-CH₂SCH₃ | H | — | CH₃ | |
| Q-3 | N | — | H | H | H | CH₃ | |
| Q-3 | N | — | 5-CF₃ | H | H | CH₃ | |
| Q-3 | N | — | 6-CH₂OCH₃ | H | H | CH₃ | |
| Q-3 | N | — | 5-CH₂SCH₃ | H | H | CH₃ | |
| Q-4 | S | — | 5-CF₃ | H | — | CH₃ | |
| Q-4 | S | — | 6-CH₂OCH₃ | H | — | CH₃ | |
| Q-4 | S | — | 5-CH₂SCH₃ | H | — | CH₃ | |
| Q-4 | O | — | 5-CF₃ | H | — | CH₃ | |
| Q-4 | O | — | 6-CH₂OCH₃ | H | — | CH₃ | |
| Q-4 | O | — | 5-CH₂SCH₃ | H | — | CH₃ | |
| Q-4 | N | — | H | H | H | CH₃ | |
| Q-4 | N | — | 5-CF₃ | H | H | CH₃ | |
| Q-4 | N | — | 6-CH₂OCH₃ | H | H | CH₃ | |
| Q-4 | N | — | 5-CH₂SCH₃ | H | H | CH₃ | |

TABLE 5

| Q | W | R | R₁ | R₂ | R₃ | X₁ | Y₂ | m.p. (°C.) |
|---|---|---|----|----|----|----|----|------|
| Q-1 | S | H | H | — | — | CH₃ | H | |
| Q-1 | S | CH₃ | 5-F | — | — | CH₃ | H | |
| Q-1 | S | CH₃ | 6-Cl | — | — | CH₃ | H | |
| Q-1 | S | CH₃ | 5-Br | — | — | CH₃ | H | |
| Q-1 | S | CH₃ | 6-CH₃ | — | — | CH₃ | CH₃ | |
| Q-1 | S | CH₃ | 5-OCH₃ | — | — | CH₃ | CH₃ | |
| Q-1 | S | CH₃ | 6-OCF₂H | — | — | CH₃ | CH₃ | |
| Q-1 | S | C₂H₅ | H | — | — | CH₃ | H | |

TABLE 5-continued

| Q | W | R | R₁ | R₂ | R₃ | X₁ | Y₂ | m.p. (°C.) |
|---|---|---|----|----|----|----|----|------|
| Q-1 | S | i-C₃H₇ | H | — | — | CH₃ | H | |
| Q-1 | S | t-C₄H₉ | H | — | — | CH₃ | CH₃ | |
| Q-1 | S | CH₃ | H | — | — | OCH₃ | H | |
| Q-1 | S | CH₃ | H | — | — | OCH₂CH₃ | H | |
| Q-1 | S | CH₃ | H | — | — | OCF₂H | H | |
| Q-1 | O | H | H | — | — | OCH₃ | H | |
| Q-1 | O | CH₃ | 5-F | — | — | OCH₃ | H | |
| Q-1 | O | CH₃ | 6-Cl | — | — | OCH₃ | H | |
| Q-1 | O | CH₃ | 5-Br | — | — | OCH₃ | H | |
| Q-1 | O | CH₃ | 6-CH₃ | — | — | OCH₃ | CH₃ | |
| Q-1 | O | CH₃ | 5-OCH₃ | — | — | OCH₃ | CH₃ | |
| Q-1 | O | CH₃ | 6-OCF₂H | — | — | OCH₃ | CH₃ | |
| Q-1 | O | C₂H₅ | H | — | — | OCH₃ | CH₃ | |
| Q-1 | O | i-C₃H₇ | H | — | — | OCH₃ | CH₃ | |
| Q-1 | O | t-C₄H₉ | H | — | — | OCH₃ | CH₃ | |
| Q-1 | N | H | H | — | CH₃ | OCH₃ | H | |
| Q-1 | N | CH₃ | 5-F | — | H | OCH₃ | H | |
| Q-1 | N | CH₃ | 6-Cl | — | H | OCH₃ | H | |
| Q-1 | N | CH₃ | 5-Br | — | H | OCH₃ | H | |
| Q-1 | N | CH₃ | 6-CH₃ | — | H | OCH₃ | H | |
| Q-1 | N | CH₃ | 5-OCH₃ | — | H | OCH₃ | H | |
| Q-1 | N | CH₃ | 6-OCF₂H | — | H | OCH₃ | CH₃ | |
| Q-1 | N | C₂H₅ | H | — | H | OCH₃ | CH₃ | |
| Q-1 | N | i-C₃H₇ | H | — | H | OCH₃ | CH₃ | |
| Q-1 | N | t-C₄H₉ | H | — | H | OCH₃ | CH₃ | |
| Q-2 | S | H | H | — | — | CH₃ | H | |
| Q-2 | S | CH₃ | 5-F | — | — | CH₃ | H | |
| Q-2 | S | CH₃ | 6-Cl | — | — | CH₃ | H | |
| Q-2 | S | CH₃ | 5-Br | — | — | CH₃ | H | |
| Q-2 | S | CH₃ | 6-CH₃ | — | — | CH₃ | H | |
| Q-2 | S | CH₃ | 5-OCH₃ | — | — | CH₃ | H | |
| Q-2 | S | CH₃ | 6-OCF₂H | — | — | CH₃ | CH₃ | |
| Q-2 | S | C₂H₅ | H | — | — | CH₃ | CH₃ | |
| Q-2 | S | i-C₃H₇ | H | — | — | CH₃ | CH₃ | |
| Q-2 | S | t-C₄H₉ | H | — | — | CH₃ | CH₃ | |
| Q-2 | O | H | H | — | — | CH₃ | CH₃ | |
| Q-2 | O | CH₃ | 5-F | — | — | CH₃ | CH₃ | |
| Q-2 | O | CH₃ | 6-Cl | — | — | CH₃ | CH₃ | |
| Q-2 | O | CH₃ | 5-Br | — | — | CH₃ | CH₃ | |
| Q-2 | O | CH₃ | 6-CH₃ | — | — | CH₃ | CH₃ | |
| Q-2 | O | CH₃ | 5-OCH₃ | — | — | CH₃ | H | |
| Q-2 | O | CH₃ | 6-OCF₂H | — | — | CH₃ | H | |
| Q-2 | O | C₂H₅ | H | — | — | CH₃ | H | |
| Q-2 | O | i-C₃H₇ | H | — | — | CH₃ | H | |
| Q-2 | O | t-C₄H₉ | H | — | — | CH₃ | H | |
| Q-2 | N | H | H | — | CH₃ | CH₃ | H | |
| Q-2 | N | CH₃ | 5-F | — | H | CH₃ | H | |
| Q-2 | N | CH₃ | 6-Cl | — | H | CH₃ | H | |
| Q-2 | N | CH₃ | 5-Br | — | H | CH₃ | H | |
| Q-2 | N | CH₃ | 6-CH₃ | — | H | CH₃ | H | |
| Q-2 | N | CH₃ | 5-OCH₃ | — | H | CH₃ | H | |
| Q-2 | N | CH₃ | 6-OCF₂H | — | H | CH₃ | CH₃ | |
| Q-2 | N | C₂H₅ | H | — | H | CH₃ | CH₃ | |
| Q-2 | N | i-C₃H₇ | H | — | H | CH₃ | CH₃ | |
| Q-2 | N | t-C₄H₉ | H | — | H | CH₃ | CH₃ | |
| Q-3 | S | — | H | H | — | CH₃ | CH₃ | |
| Q-3 | S | — | H | CH₃ | — | CH₃ | CH₃ | |
| Q-3 | S | — | 5-F | H | — | CH₃ | CH₃ | |
| Q-3 | S | — | 6-Cl | H | — | CH₃ | CH₃ | |
| Q-3 | S | — | 5-Br | H | — | CH₃ | CH₃ | |
| Q-3 | S | — | 6-CH₃ | H | — | CH₃ | H | |
| Q-3 | S | — | 5-OCH₃ | H | — | CH₃ | H | |
| Q-3 | S | — | 6-OCF₂H | H | — | CH₃ | H | |
| Q-3 | O | — | H | H | — | CH₃ | H | |
| Q-3 | O | — | 5-F | H | — | CH₃ | H | |
| Q-3 | O | — | 6-Cl | H | — | CH₃ | H | |
| Q-3 | O | — | 5-Br | H | — | CH₃ | CH₃ | |
| Q-3 | O | — | 6-CH₃ | H | — | CH₃ | CH₃ | |
| Q-3 | O | — | 5-OCH₃ | H | — | CH₃ | CH₃ | |

TABLE 5-continued

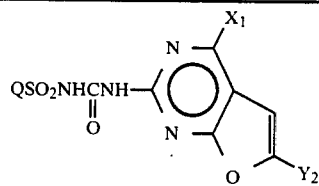

| Q | W | R | R₁ | R₂ | R₃ | X₁ | Y₂ | m.p. (°C.) |
|---|---|---|---|---|---|---|---|---|
| Q-3 | O | — | 6-OCF₂H | H | — | CH₃ | CH₃ | |
| Q-3 | N | — | H | H | CH₃ | CH₃ | CH₃ | |
| Q-3 | N | — | H | CH₃ | H | CH₃ | CH₃ | |
| Q-3 | N | — | 5-F | H | H | CH₃ | CH₃ | |
| Q-3 | N | — | 6-Cl | H | H | CH₃ | CH₃ | |
| Q-3 | N | — | 5-Br | H | H | CH₃ | H | |
| Q-3 | N | — | 6-CH₃ | H | H | CH₃ | H | |
| Q-3 | N | — | 5-OCH₃ | H | H | CH₃ | H | |
| Q-3 | N | — | 6-OCF₂H | H | H | CH₃ | H | |
| Q-4 | S | — | H | H | — | CH₃ | H | |
| Q-4 | S | — | H | CH₃ | — | CH₃ | H | |
| Q-4 | S | — | 5-F | H | — | CH₃ | H | |
| Q-4 | S | — | 6-Cl | H | — | CH₃ | H | |
| Q-4 | S | — | 5-Br | H | — | CH₃ | CH₃ | |
| Q-4 | S | — | 6-CH₃ | H | — | CH₃ | CH₃ | |
| Q-4 | S | — | 5-OCH₃ | H | — | CH₃ | CH₃ | |
| Q-4 | S | — | 6-OCF₂H | H | — | CH₃ | CH₃ | |
| Q-4 | O | — | H | H | — | CH₃ | CH₃ | |
| Q-4 | O | — | H | CH₃ | — | CH₃ | CH₃ | |
| Q-4 | O | — | 5-F | H | — | CH₃ | CH₃ | |
| Q-4 | O | — | 6-Cl | H | — | CH₃ | CH₃ | |
| Q-4 | O | — | 5-Br | H | — | CH₃ | H | |
| Q-4 | O | — | 6-CH₃ | H | — | CH₃ | H | |
| Q-4 | O | — | 5-OCH₃ | H | — | CH₃ | H | |
| Q-4 | O | — | 6-OCF₂H | H | — | CH₃ | H | |
| Q-4 | N | — | H | H | CH₃ | CH₃ | H | |
| Q-4 | N | — | H | CH₃ | H | CH₃ | H | |
| Q-4 | N | — | 5-F | H | H | CH₃ | H | |
| Q-4 | N | — | 6-Cl | H | H | CH₃ | H | |
| Q-4 | N | — | 5-Br | H | H | CH₃ | CH₃ | |
| Q-4 | N | — | 6-CH₃ | H | H | CH₃ | CH₃ | |
| Q-4 | N | — | 5-OCH₃ | H | H | CH₃ | CH₃ | |
| Q-4 | N | — | 6-OCF₂H | H | H | CH₃ | CH₃ | |
| Q-1 | S | CH₃ | H | — | — | CH₃ | H | |
| Q-1 | S | CH₃ | 5-CF₃ | — | — | CH₃ | CH₃ | |
| Q-1 | S | CH₃ | 6-CH₂OCH₃ | — | — | CH₃ | CH₃ | |
| Q-1 | S | CH₃ | 5-CH₂SCH₃ | — | — | CH₃ | CH₃ | |
| Q-1 | O | CH₃ | 5-CF₃ | — | — | OCH₃ | CH₃ | |
| Q-1 | O | CH₃ | 6-CH₂OCH₃ | — | — | OCH₃ | CH₃ | |
| Q-1 | O | CH₃ | 5-CH₂SCH₃ | — | — | OCH₃ | CH₃ | |
| Q-1 | N | CH₃ | 5-CF₃ | — | H | OCH₃ | CH₃ | |
| Q-1 | N | CH₃ | 6-CH₂OCH₃ | — | H | OCH₃ | CH₃ | |
| Q-1 | N | CH₃ | 5-CH₂SCH₃ | — | H | OCH₃ | CH₃ | |
| Q-2 | S | CH₃ | H | — | — | CH₃ | CH₃ | |
| Q-2 | S | CH₃ | 5-CF₃ | — | — | CH₃ | CH₃ | |
| Q-2 | S | CH₃ | 6-CH₂OCH₃ | — | — | CH₃ | CH₃ | |
| Q-2 | S | CH₃ | 5-CH₂SCH₃ | — | — | CH₃ | CH₃ | |
| Q-2 | O | CH₃ | H | — | — | CH₃ | H | |
| Q-2 | O | CH₃ | 5-CF₃ | — | — | CH₃ | H | |
| Q-2 | O | CH₃ | 6-CH₂OCH₃ | — | — | CH₃ | H | |
| Q-2 | O | CH₃ | 5-CH₂SCH₃ | — | — | CH₃ | H | |
| Q-2 | N | CH₃ | H | — | H | CH₃ | H | |
| Q-2 | N | CH₃ | 5-CF₃ | — | H | CH₃ | H | |
| Q-2 | N | CH₃ | 6-CH₂OCH₃ | — | H | CH₃ | H | |
| Q-2 | N | CH₃ | 5-CH₂SCH₃ | — | H | CH₃ | H | |
| Q-3 | S | — | 5-CF₃ | H | — | CH₃ | H | |
| Q-3 | S | — | 6-CH₂OCH₃ | H | — | CH₃ | H | |
| Q-3 | S | — | 5-CH₂SCH₃ | H | — | CH₃ | H | |
| Q-3 | O | — | 5-CF₃ | H | — | CH₃ | CH₃ | |
| Q-3 | O | — | 6-CH₂OCH₃ | H | — | CH₃ | CH₃ | |
| Q-3 | O | — | 5-CH₂SCH₃ | H | — | CH₃ | CH₃ | |
| Q-3 | N | — | H | H | H | CH₃ | H | |
| Q-3 | N | — | 5-CF₃ | H | H | CH₃ | H | |
| Q-3 | N | — | 6-CH₂OCH₃ | H | H | CH₃ | H | |
| Q-3 | N | — | 5-CH₂SCH₃ | H | H | CH₃ | H | |
| Q-4 | S | — | 5-CF₃ | H | — | CH₃ | CH₃ | |
| Q-4 | S | — | 6-CH₂OCH₃ | H | — | CH₃ | CH₃ | |
| Q-4 | S | — | 5-CH₂SCH₃ | H | — | CH₃ | CH₃ | |
| Q-4 | O | — | 5-CF₃ | H | — | CH₃ | H | |
| Q-4 | O | — | 6-CH₂OCH₃ | H | — | CH₃ | H | |

TABLE 5-continued

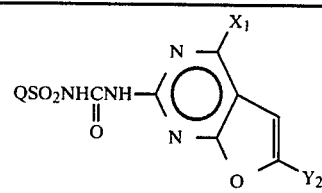

| Q | W | R | R₁ | R₂ | R₃ | X₁ | Y₂ | m.p. (°C.) |
|---|---|---|---|---|---|---|---|---|
| Q-4 | O | — | 5-CH₂SCH₃ | H | — | CH₃ | H | |
| Q-4 | N | — | H | H | H | CH₃ | CH₃ | |
| Q-4 | N | — | 5-CF₃ | H | H | CH₃ | CH₃ | |
| Q-4 | N | — | 6-CH₂OCH₃ | H | H | CH₃ | CH₃ | |
| Q-4 | N | — | 5-CH₂SCH₃ | H | H | CH₃ | CH₃ | |

TABLE 6

$$QSO_2NHCNH-\underset{N}{\overset{N-N}{\underset{\|}{\bigvee}}}\overset{Y_3}{\underset{X_2}{\bigvee}}$$

| Q | W | R | R₁ | R₂ | R₃ | X₂ | Y₃ | m.p. (°C.) |
|---|---|---|---|---|---|---|---|---|
| Q-1 | S | H | H | — | — | CH₃ | CH₃ | |
| Q-1 | S | CH₃ | H | — | — | CH₃ | CH₃ | |
| Q-1 | S | CH₃ | H | — | — | OCH₃ | CH₃ | |
| Q-1 | S | CH₃ | H | — | — | SCH₃ | CH₃ | |
| Q-1 | S | CH₃ | 5-F | — | — | CH₃ | CH₃ | |
| Q-1 | S | CH₃ | 6-Cl | — | — | CH₃ | CH₃ | |
| Q-1 | S | CH₃ | 5-Br | — | — | CH₃ | CH₃ | |
| Q-1 | S | CH₃ | 6-CH₃ | — | — | CH₃ | CH₃ | |
| Q-1 | S | CH₃ | 5-OCH₃ | — | — | CH₃ | CH₃ | |
| Q-1 | S | CH₃ | 6-OCF₂H | — | — | CH₃ | CH₃ | |
| Q-1 | S | CH₃ | 5-CF₃ | — | — | CH₃ | CH₃ | |
| Q-1 | S | CH₃ | 6-CH₂OCH₃ | — | — | CH₃ | CH₃ | |
| Q-1 | S | CH₃ | 5-CH₂SCH₃ | — | — | CH₃ | CH₃ | |
| Q-1 | S | C₂H₅ | H | — | — | CH₃ | CH₃ | |
| Q-1 | S | i-C₃H₇ | H | — | — | CH₃ | CH₃ | |
| Q-1 | S | t-C₄H₉ | H | — | — | CH₃ | CH₃ | |
| Q-1 | O | H | H | — | — | CH₃ | CH₃ | |
| Q-1 | O | CH₃ | H | — | — | CH₃ | CH₃ | |
| Q-1 | O | CH₃ | 5-F | — | — | CH₃ | CH₃ | |
| Q-1 | O | CH₃ | 6-Cl | — | — | CH₃ | CH₃ | |
| Q-1 | O | CH₃ | 5-Br | — | — | CH₃ | CH₃ | |
| Q-1 | O | CH₃ | 6-CH₃ | — | — | CH₃ | CH₃ | |
| Q-1 | O | CH₃ | 5-OCH₃ | — | — | CH₃ | CH₃ | |
| Q-1 | O | CH₃ | 6-OCF₂H | — | — | CH₃ | CH₃ | |
| Q-1 | O | CH₃ | 5-CF₃ | — | — | CH₃ | CH₃ | |
| Q-1 | O | CH₃ | 6-CH₂OCH₃ | — | — | CH₃ | CH₃ | |
| Q-1 | O | CH₃ | 5-CH₂SCH₃ | — | — | CH₃ | CH₃ | |
| Q-1 | O | C₂H₅ | H | — | — | CH₃ | CH₃ | |
| Q-1 | O | i-C₃H₇ | H | — | — | CH₃ | CH₃ | |
| Q-1 | O | t-C₄H₉ | H | — | — | CH₃ | CH₃ | |
| Q-1 | N | H | H | — | CH₃ | CH₃ | CH₃ | |
| Q-1 | N | H | CH₃ | — | H | CH₃ | CH₃ | |
| Q-1 | N | CH₃ | H | — | H | CH₃ | CH₃ | |
| Q-1 | N | CH₃ | 5-F | — | H | CH₃ | CH₃ | |
| Q-1 | N | CH₃ | 6-Cl | — | H | CH₃ | CH₃ | |
| Q-1 | N | CH₃ | 5-Br | — | H | CH₃ | CH₃ | |
| Q-1 | N | CH₃ | 6-CH₃ | — | H | CH₃ | CH₃ | |
| Q-1 | N | CH₃ | 5-OCH₃ | — | H | CH₃ | CH₃ | |
| Q-1 | N | CH₃ | 6-OCF₂H | — | H | CH₃ | CH₃ | |
| Q-1 | N | CH₃ | 5-CF₃ | — | H | CH₃ | CH₃ | |
| Q-1 | N | CH₃ | 6-CH₂OCH₃ | — | H | CH₃ | CH₃ | |
| Q-1 | N | CH₃ | 5-CH₂SCH₃ | — | H | CH₃ | CH₃ | |
| Q-1 | N | C₂H₅ | H | — | H | CH₃ | CH₃ | |
| Q-1 | N | i-C₃H₇ | H | — | H | CH₃ | CH₃ | |
| Q-1 | N | t-C₄H₉ | H | — | H | CH₃ | CH₃ | |
| Q-2 | S | H | H | — | — | CH₃ | CH₃ | |
| Q-2 | S | CH₃ | H | — | — | CH₃ | CH₃ | |
| Q-2 | S | CH₃ | 5-F | — | — | CH₃ | CH₃ | |
| Q-2 | S | CH₃ | 6-Cl | — | — | CH₃ | CH₃ | |
| Q-2 | S | CH₃ | 5-Br | — | — | CH₃ | CH₃ | |
| Q-2 | S | CH₃ | 6-CH₃ | — | — | CH₃ | CH₃ | |
| Q-2 | S | CH₃ | 5-OCH₃ | — | — | CH₃ | CH₃ | |

TABLE 6-continued

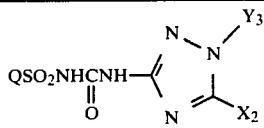

| Q | W | R | R₁ | R₂ | R₃ | X₂ | Y₃ | m.p. (°C.) |
|---|---|---|---|---|---|---|---|---|
| Q-2 | S | CH₃ | 6-OCF₂H | — | — | CH₃ | CH₃ | |
| Q-2 | S | CH₃ | 5-CF₃ | — | — | CH₃ | CH₃ | |
| Q-2 | S | CH₃ | 6-CH₂OCH₃ | — | — | CH₃ | CH₃ | |
| Q-2 | S | CH₃ | 5-CH₂SCH₃ | — | — | CH₃ | CH₃ | |
| Q-2 | S | C₂H₅ | H | — | — | CH₃ | CH₃ | |
| Q-2 | S | i-C₃H₇ | H | — | — | CH₃ | CH₃ | |
| Q-2 | S | t-C₄H₉ | H | — | — | CH₃ | CH₃ | |
| Q-2 | O | H | H | — | — | CH₃ | CH₃ | |
| Q-2 | O | CH₃ | H | — | — | CH₃ | CH₃ | |
| Q-2 | O | CH₃ | 5-F | — | — | CH₃ | CH₃ | |
| Q-2 | O | CH₃ | 6-Cl | — | — | CH₃ | CH₃ | |
| Q-2 | O | CH₃ | 5-Br | — | — | CH₃ | CH₃ | |
| Q-2 | O | CH₃ | 6-CH₃ | — | — | CH₃ | CH₃ | |
| Q-2 | O | CH₃ | 5-OCH₃ | — | — | CH₃ | CH₃ | |
| Q-2 | O | CH₃ | 6-OCF₂H | — | — | CH₃ | CH₃ | |
| Q-2 | O | CH₃ | 5-CF₃ | — | — | CH₃ | CH₃ | |
| Q-2 | O | CH₃ | 6-CH₂OCH₃ | — | — | CH₃ | CH₃ | |
| Q-2 | O | CH₃ | 5-CH₂SCH₃ | — | — | CH₃ | CH₃ | |
| Q-2 | O | C₂H₅ | H | — | — | CH₃ | CH₃ | |
| Q-2 | O | i-C₃H₇ | H | — | — | CH₃ | CH₃ | |
| Q-2 | O | t-C₄H₉ | H | — | — | CH₃ | CH₃ | |
| Q-2 | N | H | H | — | CH₃ | CH₃ | CH₃ | |
| Q-2 | N | H | CH₃ | — | H | CH₃ | CH₃ | |
| Q-2 | N | CH₃ | H | — | H | CH₃ | CH₃ | |
| Q-2 | N | CH₃ | 5-F | — | H | CH₃ | CH₃ | |
| Q-2 | N | CH₃ | 6-Cl | — | H | CH₃ | CH₃ | |
| Q-2 | N | CH₃ | 5-Br | — | H | CH₃ | CH₃ | |
| Q-2 | N | CH₃ | 6-CH₃ | — | H | CH₃ | CH₃ | |
| Q-2 | N | CH₃ | 5-OCH₃ | — | H | CH₃ | CH₃ | |
| Q-2 | N | CH₃ | 6-OCF₂H | — | H | CH₃ | CH₃ | |
| Q-2 | N | CH₃ | 5-CF₃ | — | H | CH₃ | CH₃ | |
| Q-2 | N | CH₃ | 6-CH₂OCH₃ | — | H | CH₃ | CH₃ | |
| Q-2 | N | CH₃ | 5-CH₂SCH₃ | — | H | CH₃ | CH₃ | |
| Q-2 | N | C₂H₅ | H | — | H | CH₃ | CH₃ | |
| Q-2 | N | i-C₃H₇ | H | — | H | CH₃ | CH₃ | |
| Q-2 | N | t-C₄H₉ | H | — | H | CH₃ | CH₃ | |
| Q-3 | S | — | H | H | — | CH₃ | CH₃ | |
| Q-3 | S | — | H | CH₃ | — | CH₃ | CH₃ | |
| Q-3 | S | — | 5-F | H | — | CH₃ | CH₃ | |
| Q-3 | S | — | 6-Cl | H | — | CH₃ | CH₃ | |
| Q-3 | S | — | 5-Br | H | — | CH₃ | CH₃ | |
| Q-3 | S | — | 6-CH₃ | H | — | CH₃ | CH₃ | |
| Q-3 | S | — | 5-OCH₃ | H | — | CH₃ | CH₃ | |
| Q-3 | S | — | 6-OCF₂H | H | — | CH₃ | CH₃ | |
| Q-3 | S | — | 5-CF₃ | H | — | CH₃ | CH₃ | |
| Q-3 | S | — | 6-CH₂OCH₃ | H | — | CH₃ | CH₃ | |
| Q-3 | S | — | 5-CH₂SCH₃ | H | — | CH₃ | CH₃ | |
| Q-3 | O | — | H | H | — | CH₃ | CH₃ | |
| Q-3 | O | — | H | CH₃ | — | CH₃ | CH₃ | |
| Q-3 | O | — | 5-F | H | — | CH₃ | CH₃ | |
| Q-3 | O | — | 6-Cl | H | — | CH₃ | CH₃ | |
| Q-3 | O | — | 5-Br | H | — | CH₃ | CH₃ | |
| Q-3 | O | — | 6-CH₃ | H | — | CH₃ | CH₃ | |
| Q-3 | O | — | 5-OCH₃ | H | — | CH₃ | CH₃ | |
| Q-3 | O | — | 6-OCF₂H | H | — | CH₃ | CH₃ | |
| Q-3 | O | — | 5-CF₃ | H | — | CH₃ | CH₃ | |
| Q-3 | O | — | 6-CH₂OCH₃ | H | — | CH₃ | CH₃ | |
| Q-3 | O | — | 5-CH₂SCH₃ | H | — | CH₃ | CH₃ | |
| Q-3 | N | — | H | H | CH₃ | CH₃ | CH₃ | |
| Q-3 | N | — | H | CH₃ | H | CH₃ | CH₃ | |
| Q-3 | N | — | H | H | H | CH₃ | CH₃ | |
| Q-3 | N | — | 5-F | H | H | CH₃ | CH₃ | |
| Q-3 | N | — | 6-Cl | H | H | CH₃ | CH₃ | |
| Q-3 | N | — | 5-Br | H | H | CH₃ | CH₃ | |
| Q-3 | N | — | 6-CH₃ | H | H | CH₃ | CH₃ | |
| Q-3 | N | — | 5-OCH₃ | H | H | CH₃ | CH₃ | |
| Q-3 | N | — | 6-OCF₂H | H | H | CH₃ | CH₃ | |
| Q-3 | N | — | 5-CF₃ | H | H | CH₃ | CH₃ | |
| Q-3 | N | — | 6-CH₂OCH₃ | H | H | CH₃ | CH₃ | |
| Q-3 | N | — | 5-CH₂SCH₃ | H | H | CH₃ | CH₃ | |
| Q-4 | S | — | H | H | — | CH₃ | C₂H₅ | |
| Q-4 | S | — | H | CH₃ | — | CH₃ | C₂H₅ | |
| Q-4 | S | — | 5-F | H | — | CH₃ | C₂H₅ | |

TABLE 6-continued

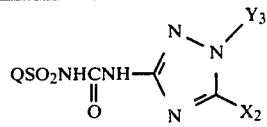

| Q | W | R | R₁ | R₂ | R₃ | X₂ | Y₃ | m.p. (°C.) |
|---|---|---|---|---|---|---|---|---|
| Q-4 | S | — | 6-Cl | H | — | CH₃ | C₂H₅ | |
| Q-4 | S | — | 5-Br | H | — | CH₃ | C₂H₅ | |
| Q-4 | S | — | 6-CH₃ | H | — | CH₃ | C₂H₅ | |
| Q-4 | S | — | 5-OCH₃ | H | — | CH₃ | C₂H₅ | |
| Q-4 | S | — | 6-OCF₂H | H | — | CH₃ | C₂H₅ | |
| Q-4 | S | — | 5-CF₃ | H | — | CH₃ | C₂H₅ | |
| Q-4 | S | — | 6-CH₂OCH₃ | H | — | CH₃ | C₂H₅ | |
| Q-4 | S | — | 5-CH₂SCH₃ | H | — | CH₃ | C₂H₅ | |
| Q-4 | O | — | H | H | — | CH₃ | C₂H₅ | |
| Q-4 | O | — | H | CH₃ | — | CH₃ | C₂H₅ | |
| Q-4 | O | — | 5-F | H | — | CH₃ | C₂H₅ | |
| Q-4 | O | — | 6-Cl | H | — | CH₃ | C₂H₅ | |
| Q-4 | O | — | 5-Br | H | — | CH₃ | C₂H₅ | |
| Q-4 | O | — | 6-CH₃ | H | — | CH₃ | C₂H₅ | |
| Q-4 | O | — | 5-OCH₃ | H | — | CH₃ | C₂H₅ | |
| Q-4 | O | — | 6-OCF₂H | H | — | CH₃ | C₂H₅ | |
| Q-4 | O | — | 5-CF₃ | H | — | CH₃ | C₂H₅ | |
| Q-4 | O | — | 6-CH₂OCH₃ | H | — | CH₃ | C₂H₅ | |
| Q-4 | O | — | 5-CH₂SCH₃ | H | — | CH₃ | C₂H₅ | |
| Q-4 | N | — | H | H | CH₃ | CH₃ | CH₂CF₃ | |
| Q-4 | N | — | H | CH₃ | H | CH₃ | CH₂CF₃ | |
| Q-4 | N | — | H | H | H | CH₃ | CH₂CF₃ | |
| Q-4 | N | — | 5-F | H | H | CH₃ | CH₂CF₃ | |
| Q-4 | N | — | 6-Cl | H | H | CH₃ | CH₂CF₃ | |
| Q-4 | N | — | 5-Br | H | H | CH₃ | CH₂CF₃ | |
| Q-4 | N | — | 6-CH₃ | H | H | CH₃ | CH₂CF₃ | |
| Q-4 | N | — | 5-OCH₃ | H | H | CH₃ | CH₂CF₃ | |
| Q-4 | N | — | 6-OCF₂H | H | H | CH₃ | CH₂CF₃ | |
| Q-4 | N | — | 5-CF₃ | H | H | CH₃ | CH₂CF₃ | |
| Q-4 | N | — | 6-CH₂OCH₃ | H | H | CH₃ | CH₂CF₃ | |
| Q-4 | N | — | 5-CH₂SCH₃ | H | H | CH₃ | CH₂CF₃ | |

TABLE 7

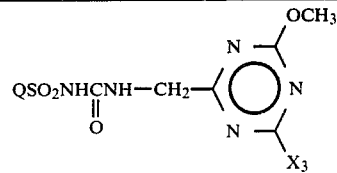

| Q | W | R | R₁ | R₂ | R₃ | X₃ | m.p.(°C.) |
|---|---|---|---|---|---|---|---|
| Q-1 | S | H | H | — | — | CH₃ | |
| Q-1 | S | CH₃ | H | — | — | CH₃ | |
| Q-1 | S | CH₃ | 5-F | — | — | CH₃ | |
| Q-1 | S | CH₃ | 6-Cl | — | — | CH₃ | |
| Q-1 | S | CH₃ | 5-Br | — | — | CH₃ | |
| Q-1 | S | CH₃ | 6-CH₃ | — | — | CH₃ | |
| Q-1 | S | CH₃ | 5-OCH₃ | — | — | CH₃ | |
| Q-1 | S | CH₃ | 6-OCF₂H | — | — | CH₃ | |
| Q-1 | S | CH₃ | 5-CF₃ | — | — | CH₃ | |
| Q-1 | S | CH₃ | 6-CH₂OCH₃ | — | — | CH₃ | |
| Q-1 | S | CH₃ | 5-CH₂SCH₃ | — | — | CH₃ | |
| Q-1 | S | C₂H₅ | H | — | — | CH₃ | |
| Q-1 | S | i-C₃H₇ | H | — | — | CH₃ | |
| Q-1 | S | t-C₄H₉ | H | — | — | CH₃ | |
| Q-1 | S | CH₃ | H | — | — | OCH₃ | |
| Q-1 | O | H | H | — | — | CH₃ | |
| Q-1 | O | CH₃ | H | — | — | CH₃ | |
| Q-1 | O | CH₃ | 5-F | — | — | CH₃ | |
| Q-1 | O | CH₃ | 6-Cl | — | — | CH₃ | |
| Q-1 | O | CH₃ | 5-Br | — | — | CH₃ | |
| Q-1 | O | CH₃ | 6-CH₃ | — | — | CH₃ | |
| Q-1 | O | CH₃ | 5-OCH₃ | — | — | CH₃ | |
| Q-1 | O | CH₃ | 6-OCF₂H | — | — | CH₃ | |
| Q-1 | O | CH₃ | 5-CF₃ | — | — | CH₃ | |
| Q-1 | O | CH₃ | 6-CH₂OCH₃ | — | — | CH₃ | |
| Q-1 | O | CH₃ | 5-CH₂SCH₃ | — | — | CH₃ | |
| Q-1 | O | C₂H₅ | H | — | — | CH₃ | |

TABLE 7-continued $$\text{QSO}_2\text{NHCNH}-\text{CH}_2-\underset{\substack{\|\\O}}{}\begin{array}{c}\text{pyrimidine with OCH}_3, X_3\end{array}$$

| Q | W | R | R₁ | R₂ | R₃ | X₃ | m.p.(°C.) |
|---|---|---|---|---|---|---|---|
| Q-1 | O | i-C₃H₇ | H | — | — | CH₃ | |
| Q-1 | O | t-C₄H₉ | H | — | — | CH₃ | |
| Q-1 | O | CH₃ | H | — | — | OCH₃ | |
| Q-1 | N | H | H | — | CH₃ | CH₃ | |
| Q-1 | N | H | H | — | H | CH₃ | |
| Q-1 | N | CH₃ | H | — | H | CH₃ | |
| Q-1 | N | CH₃ | 5-F | — | H | CH₃ | |
| Q-1 | N | CH₃ | 5-Cl | — | H | CH₃ | |
| Q-1 | N | CH₃ | 5-Br | — | H | CH₃ | |
| Q-1 | N | CH₃ | 6-CH₃ | — | H | CH₃ | |
| Q-1 | N | CH₃ | 5-OCH₃ | — | H | CH₃ | |
| Q-1 | N | CH₃ | 6-OCF₂H | — | H | CH₃ | |
| Q-1 | N | CH₃ | 5-CF₃ | — | H | CH₃ | |
| Q-1 | N | CH₃ | 6-CH₂OCH₃ | — | H | CH₃ | |
| Q-1 | N | CH₃ | 5-CH₂SCH₃ | — | H | CH₃ | |
| Q-1 | N | C₂H₅ | H | — | H | CH₃ | |
| Q-1 | N | i-C₃H₇ | H | — | H | CH₃ | |
| Q-1 | N | t-C₄H₉ | H | — | H | CH₃ | |
| Q-1 | N | CH₃ | H | — | H | OCH₃ | |
| Q-2 | S | H | H | — | — | CH₃ | |
| Q-2 | S | CH₃ | H | — | — | CH₃ | |
| Q-2 | S | CH₃ | 5-F | — | — | CH₃ | |
| Q-2 | S | CH₃ | 6-Cl | — | — | CH₃ | |
| Q-2 | S | CH₃ | 5-Br | — | — | CH₃ | |
| Q-2 | S | CH₃ | 6-CH₃ | — | — | CH₃ | |
| Q-2 | S | CH₃ | 5-OCH₃ | — | — | CH₃ | |
| Q-2 | S | CH₃ | 6-OCF₂H | — | — | CH₃ | |
| Q-2 | S | CH₃ | 5-CF₃ | — | — | CH₃ | |
| Q-2 | S | CH₃ | 6-CH₂OCH₃ | — | — | CH₃ | |
| Q-2 | S | CH₃ | 5-CH₂SCH₃ | — | — | CH₃ | |
| Q-2 | S | C₂H₅ | H | — | — | CH₃ | |
| Q-2 | S | i-C₃H₇ | H | — | — | CH₃ | |
| Q-2 | S | t-C₄H₉ | H | — | — | CH₃ | |
| Q-2 | S | CH₃ | H | — | — | OCH₃ | |
| Q-2 | O | H | H | — | — | CH₃ | |
| Q-2 | O | CH₃ | H | — | — | CH₃ | |
| Q-2 | O | CH₃ | 5-F | — | — | CH₃ | |
| Q-2 | O | CH₃ | 6-Cl | — | — | CH₃ | |
| Q-2 | O | CH₃ | 5-Br | — | — | CH₃ | |
| Q-2 | O | CH₃ | 6-CH₃ | — | — | CH₃ | |
| Q-2 | O | CH₃ | 5-OCH₃ | — | — | CH₃ | |
| Q-2 | O | CH₃ | 6-OCF₂H | — | — | CH₃ | |
| Q-2 | O | CH₃ | 5-CF₃ | — | — | CH₃ | |
| Q-2 | O | CH₃ | 6-CH₂OCH₃ | — | — | CH₃ | |
| Q-2 | O | CH₃ | 5-CH₂SCH₃ | — | — | CH₃ | |
| Q-2 | O | C₂H₅ | H | — | — | CH₃ | |
| Q-2 | O | i-C₃H₇ | H | — | — | CH₃ | |
| Q-2 | O | t-C₄H₉ | H | — | — | CH₃ | |
| Q-2 | O | CH₃ | H | — | — | OCH₃ | |
| Q-2 | N | H | H | — | CH₃ | CH₃ | |
| Q-2 | N | H | H | — | H | CH₃ | |
| Q-2 | N | CH₃ | H | — | H | CH₃ | |
| Q-2 | N | CH₃ | 5-F | — | H | CH₃ | |
| Q-2 | N | CH₃ | 6-Cl | — | H | CH₃ | |
| Q-2 | N | CH₃ | 5-Br | — | H | CH₃ | |
| Q-2 | N | CH₃ | 6-CH₃ | — | H | CH₃ | |
| Q-2 | N | CH₃ | 5-OCH₃ | — | H | CH₃ | |
| Q-2 | N | CH₃ | 6-OCF₂H | — | H | CH₃ | |
| Q-2 | N | CH₃ | 5-CF₃ | — | H | CH₃ | |
| Q-2 | N | CH₃ | 6-CH₂OCH₃ | — | H | CH₃ | |
| Q-2 | N | CH₃ | 5-CH₂SCH₃ | — | H | CH₃ | |
| Q-2 | N | C₂H₅ | H | — | H | CH₃ | |
| Q-2 | N | i-C₃H₇ | H | — | H | CH₃ | |
| Q-2 | N | t-C₄H₉ | H | — | H | CH₃ | |
| Q-2 | N | CH₃ | H | — | H | OCH₃ | |
| Q-3 | S | — | H | H | — | CH₃ | |
| Q-3 | S | — | H | CH₃ | — | CH₃ | |
| Q-3 | S | — | 5-F | H | — | CH₃ | |
| Q-3 | S | — | 6-Cl | H | — | CH₃ | |
| Q-3 | S | — | 5-Br | H | — | CH₃ | |
| Q-3 | S | — | 6-CH₃ | H | — | CH₃ | |
| Q-3 | S | — | 5-OCH₃ | H | — | CH₃ | |
| Q-3 | S | — | 6-OCF₂H | H | — | CH₃ | |
| Q-3 | S | — | 5-CF₃ | H | — | CH₃ | |
| Q-3 | S | — | 6-CH₂OCH₃ | H | — | CH₃ | |
| Q-3 | S | — | 5-CH₂SCH₃ | H | — | CH₃ | |
| Q-3 | S | — | H | H | — | OCH₃ | |
| Q-3 | O | — | H | H | — | CH₃ | |
| Q-3 | O | — | H | CH₃ | — | CH₃ | |
| Q-3 | O | — | 5-F | H | — | CH₃ | |
| Q-3 | O | — | 6-Cl | H | — | CH₃ | |
| Q-3 | O | — | 5-Br | H | — | CH₃ | |
| Q-3 | O | — | 6-CH₃ | H | — | CH₃ | |
| Q-3 | O | — | 5-OCH₃ | H | — | CH₃ | |
| Q-3 | O | — | 6-OCF₂H | H | — | CH₃ | |
| Q-3 | O | — | 5-CF₃ | H | — | CH₃ | |
| Q-3 | O | — | 6-CH₂OCH₃ | H | — | CH₃ | |
| Q-3 | O | — | 5-CH₂SCH₃ | H | — | CH₃ | |
| Q-3 | O | — | H | H | — | OCH₃ | |
| Q-3 | N | — | H | H | CH₃ | CH₃ | |
| Q-3 | N | — | H | CH₃ | H | CH₃ | |
| Q-3 | N | — | H | H | H | CH₃ | |
| Q-3 | N | — | 5-F | H | H | CH₃ | |
| Q-3 | N | — | 6-Cl | H | H | CH₃ | |
| Q-3 | N | — | 5-Br | H | H | CH₃ | |
| Q-3 | N | — | 6-CH₃ | H | H | CH₃ | |
| Q-3 | N | — | 5-OCH₃ | H | H | CH₃ | |
| Q-3 | N | — | 6-OCF₂H | H | H | CH₃ | |
| Q-3 | N | — | 5-CF₃ | H | H | CH₃ | |
| Q-3 | N | — | 6-CH₂OCH₃ | H | H | CH₃ | |
| Q-3 | N | — | 5-CH₂SCH₃ | H | H | CH₃ | |
| Q-3 | N | — | H | H | H | OCH₃ | |
| Q-4 | S | — | H | H | — | CH₃ | |
| Q-4 | S | — | H | CH₃ | — | CH₃ | |
| Q-4 | S | — | 5-F | H | — | CH₃ | |
| Q-4 | S | — | 6-Cl | H | — | CH₃ | |
| Q-4 | S | — | 5-Br | H | — | CH₃ | |
| Q-4 | S | — | 6-CH₃ | H | — | CH₃ | |
| Q-4 | S | — | 5-OCH₃ | H | — | CH₃ | |
| Q-4 | S | — | 6-OCF₂H | H | — | CH₃ | |
| Q-4 | S | — | 5-CF₃ | H | — | CH₃ | |
| Q-4 | S | — | 6-CH₂OCH₃ | H | — | CH₃ | |
| Q-4 | S | — | 5-CH₂SCH₃ | H | — | CH₃ | |
| Q-4 | S | — | H | H | — | OCH₃ | |
| Q-4 | O | — | H | H | — | CH₃ | |
| Q-4 | O | — | H | CH₃ | — | CH₃ | |
| Q-4 | O | — | 5-F | H | — | CH₃ | |
| Q-4 | O | — | 6-Cl | H | — | CH₃ | |
| Q-4 | O | — | 5-Br | H | — | CH₃ | |
| Q-4 | O | — | 6-CH₃ | H | — | CH₃ | |
| Q-4 | O | — | 5-OCH₃ | H | — | CH₃ | |
| Q-4 | O | — | 6-OCF₂H | H | — | CH₃ | |
| Q-4 | O | — | 5-CF₃ | H | — | CH₃ | |
| Q-4 | O | — | 6-CH₂OCH₃ | H | — | CH₃ | |
| Q-4 | O | — | 5-CH₂SCH₃ | H | — | CH₃ | |
| Q-4 | O | — | H | H | — | OCH₃ | |
| Q-4 | N | — | H | H | CH₃ | CH₃ | |
| Q-4 | N | — | H | CH₃ | H | CH₃ | |
| Q-4 | N | — | H | H | H | CH₃ | |
| Q-4 | N | — | 5-F | H | H | CH₃ | |
| Q-4 | N | — | 6-Cl | H | H | CH₃ | |
| Q-4 | N | — | 5-Br | H | H | CH₃ | |
| Q-4 | N | — | 6-CH₃ | H | H | CH₃ | |
| Q-4 | N | — | 5-OCH₃ | H | H | CH₃ | |
| Q-4 | N | — | 6-OCF₂H | H | H | CH₃ | |
| Q-4 | N | — | 5-CF₃ | H | H | CH₃ | |
| Q-4 | N | — | 6-CH₂OCH₃ | H | H | CH₃ | |
| Q-4 | N | — | 5-CH₂SCH₃ | H | H | CH₃ | |
| Q-4 | N | — | H | H | H | OCH₃ | |

TABLE 8

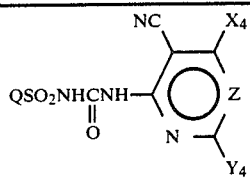

| Q | W | R | R₁ | R₂ | R₃ | X₄ | Y₄ | Z | m.p. (°C.) |
|---|---|---|---|---|---|---|---|---|---|
| Q-1 | S | H | H | — | — | CH₃ | CH₃ | CH | |
| Q-1 | S | CH₃ | H | — | — | CH₃ | CH₃ | N | |
| Q-1 | S | CH₃ | H | — | — | CH₃ | CH₃ | CH | |
| Q-1 | S | CH₃ | H | — | — | OCH₃ | CH₃ | CH | |
| Q-1 | S | CH₃ | H | — | — | OCH₂CH₃ | CH₃ | CH | |
| Q-1 | S | CH₃ | H | — | — | CH₂OCH₃ | CH₃ | CH | |
| Q-1 | S | CH₃ | H | — | — | Cl | CH₃ | CH | |
| Q-1 | S | CH₃ | H | — | — | CH₃ | OCH₂CH₃ | CH | |
| Q-1 | S | CH₃ | H | — | — | CH₃ | OCH₃ | CH | |
| Q-1 | S | CH₃ | H | — | — | CH₃ | Cl | CH | |
| Q-1 | S | CH₃ | 5-F | — | — | CH₃ | CH₃ | CH | |
| Q-1 | S | CH₃ | 6-Cl | — | — | CH₃ | CH₃ | CH | |
| Q-1 | S | CH₃ | 5-Br | — | — | CH₃ | CH₃ | CH | |
| Q-1 | S | CH₃ | 6-CH₃ | — | — | CH₃ | CH₃ | CH | |
| Q-1 | S | CH₃ | 5-OCH₃ | — | — | CH₃ | CH₃ | CH | |
| Q-1 | S | CH₃ | 6-OCF₂H | — | — | CH₃ | CH₃ | CH | |
| Q-1 | S | CH₃ | 5-CF₃ | — | — | CH₃ | CH₃ | CH | |
| Q-1 | S | CH₃ | 6-CH₂OCH₃ | — | — | CH₃ | CH₃ | CH | |
| Q-1 | S | CH₃ | 5-CH₂SCH₃ | — | — | CH₃ | CH₃ | CH | |
| Q-1 | S | C₂H₅ | H | — | — | CH₃ | CH₃ | CH | |
| Q-1 | S | i-C₃H₇ | H | — | — | CH₃ | CH₃ | CH | |
| Q-1 | S | t-C₄H₉ | H | — | — | CH₃ | CH₃ | CH | |
| Q-1 | O | CH₃ | H | — | — | CH₃ | CH₃ | CH | |
| Q-1 | O | CH₃ | 5-F | — | — | CH₃ | CH₃ | CH | |
| Q-1 | O | CH₃ | 6-Cl | — | — | CH₃ | CH₃ | CH | |
| Q-1 | O | CH₃ | 5-Br | — | — | CH₃ | CH₃ | CH | |
| Q-1 | O | CH₃ | 6-CH₃ | — | — | CH₃ | CH₃ | CH | |
| Q-1 | O | CH₃ | 5-OCH₃ | — | — | CH₃ | CH₃ | CH | |
| Q-1 | O | CH₃ | 6-OCF₂H | — | — | CH₃ | CH₃ | CH | |
| Q-1 | O | CH₃ | 5-CF₃ | — | — | CH₃ | CH₃ | CH | |
| Q-1 | O | CH₃ | 6-CH₂OCH₃ | — | — | CH₃ | CH₃ | CH | |
| Q-1 | O | CH₃ | 5-CH₂SCH₃ | — | — | CH₃ | CH₃ | CH | |
| Q-1 | N | H | H | — | CH₃ | CH₃ | CH₃ | CH | |
| Q-1 | N | H | H | — | H | CH₃ | CH₃ | CH | |
| Q-1 | N | CH₃ | H | — | H | CH₃ | CH₃ | CH | |
| Q-1 | N | CH₃ | 5-F | — | H | CH₃ | CH₃ | CH | |
| Q-1 | N | CH₃ | 6-Cl | — | H | CH₃ | CH₃ | CH | |
| Q-1 | N | CH₃ | 5-Br | — | H | CH₃ | CH₃ | CH | |
| Q-1 | N | CH₃ | 6-CH₃ | — | H | CH₃ | CH₃ | CH | |
| Q-1 | N | CH₃ | 5-OCH₃ | — | H | CH₃ | CH₃ | CH | |
| Q-1 | N | CH₃ | 6-OCF₂H | — | H | CH₃ | CH₃ | CH | |
| Q-1 | N | CH₃ | 5-CF₃ | — | H | CH₃ | CH₃ | CH | |
| Q-1 | N | CH₃ | 6-CH₂OCH₃ | — | H | CH₃ | CH₃ | CH | |
| Q-1 | N | CH₃ | 5-CH₂SCH₃ | — | H | CH₃ | CH₃ | CH | |
| Q-2 | S | CH₃ | H | — | — | CH₃ | CH₃ | CH | |
| Q-2 | S | CH₃ | 5-F | — | — | CH₃ | CH₃ | CH | |
| Q-2 | S | CH₃ | 6-Cl | — | — | CH₃ | CH₃ | CH | |
| Q-2 | S | CH₃ | 5-Br | — | — | CH₃ | CH₃ | CH | |
| Q-2 | S | CH₃ | 6-CH₃ | — | — | CH₃ | CH₃ | CH | |
| Q-2 | S | CH₃ | 5-OCH₃ | — | — | CH₃ | CH₃ | CH | |
| Q-2 | S | CH₃ | 6-OCF₂H | — | — | CH₃ | CH₃ | CH | |
| Q-2 | S | CH₃ | 5-CF₃ | — | — | CH₃ | CH₃ | CH | |
| Q-2 | S | CH₃ | 6-CH₂OCH₃ | — | — | CH₃ | CH₃ | CH | |
| Q-2 | S | CH₃ | 5-CH₂SCH₃ | — | — | CH₃ | CH₃ | CH | |
| Q-2 | O | CH₃ | H | — | — | CH₃ | CH₃ | CH | |
| Q-2 | O | CH₃ | 5-F | — | — | CH₃ | CH₃ | CH | |
| Q-2 | O | CH₃ | 6-Cl | — | — | CH₃ | CH₃ | CH | |
| Q-2 | O | CH₃ | 5-Br | — | — | CH₃ | CH₃ | CH | |
| Q-2 | O | CH₃ | 6-CH₃ | — | — | CH₃ | CH₃ | CH | |
| Q-2 | O | CH₃ | 5-OCH₃ | — | — | CH₃ | CH₃ | CH | |
| Q-2 | O | CH₃ | 6-OCF₂H | — | — | CH₃ | CH₃ | CH | |
| Q-2 | O | CH₃ | 5-CF₃ | — | — | CH₃ | CH₃ | CH | |
| Q-2 | O | CH₃ | 6-CH₂OCH₃ | — | — | CH₃ | CH₃ | CH | |
| Q-2 | O | CH₃ | 5-CH₂SCH₃ | — | — | CH₃ | CH₃ | CH | |
| Q-2 | N | H | H | — | CH₃ | CH₃ | CH₃ | CH | |
| Q-2 | N | H | H | — | H | CH₃ | CH₃ | CH | |
| Q-2 | N | CH₃ | 5-F | — | H | CH₃ | CH₃ | CH | |
| Q-2 | N | CH₃ | 6-Cl | — | H | CH₃ | CH₃ | CH | |
| Q-2 | N | CH₃ | 5-Br | — | H | CH₃ | CH₃ | CH | |
| Q-2 | N | CH₃ | 6-CH₃ | — | H | CH₃ | CH₃ | CH | |
| Q-2 | N | CH₃ | 5-OCH₃ | — | H | CH₃ | CH₃ | CH | |

TABLE 8-continued

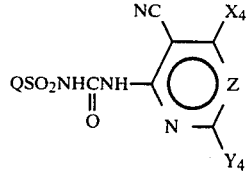

| Q | W | R | R₁ | R₂ | R₃ | X₄ | Y₄ | Z | m.p. (°C.) |
|---|---|---|---|---|---|---|---|---|---|
| Q-2 | N | CH₃ | 6-OCF₂H | — | H | CH₃ | CH₃ | CH | |
| Q-2 | N | CH₃ | 5-CF₃ | — | H | CH₃ | CH₃ | CH | |
| Q-2 | N | CH₃ | 6-CH₂OCH₃ | — | H | CH₃ | CH₃ | CH | |
| Q-2 | N | CH₃ | 5-CH₂SCH₃ | — | H | CH₃ | CH₃ | CH | |
| Q-3 | S | — | H | CH₃ | — | CH₃ | CH₃ | CH | |
| Q-3 | S | — | H | H | — | CH₃ | CH₃ | CH | |
| Q-3 | S | — | 5-F | H | — | CH₃ | CH₃ | CH | |
| Q-3 | S | — | 6-Cl | H | — | CH₃ | CH₃ | CH | |
| Q-3 | S | — | 5-Br | H | — | CH₃ | CH₃ | CH | |
| Q-3 | S | — | 6-CH₃ | H | — | CH₃ | CH₃ | CH | |
| Q-3 | S | — | 5-OCH₃ | H | — | CH₃ | CH₃ | CH | |
| Q-3 | S | — | 6-OCF₂H | H | — | CH₃ | CH₃ | CH | |
| Q-3 | S | — | 5-CF₃ | H | — | CH₃ | CH₃ | CH | |
| Q-3 | S | — | 6-CH₂OCH₃ | H | — | CH₃ | CH₃ | CH | |
| Q-3 | S | — | 5-CH₂SCH₃ | H | — | CH₃ | CH₃ | CH | |
| Q-3 | O | — | H | H | — | CH₃ | CH₃ | CH | |
| Q-3 | O | — | H | CH₃ | — | CH₃ | CH₃ | CH | |
| Q-3 | O | — | 5-F | H | — | CH₃ | CH₃ | CH | |
| Q-3 | O | — | 6-Cl | H | — | CH₃ | CH₃ | CH | |
| Q-3 | O | — | 5-Br | H | — | CH₃ | CH₃ | CH | |
| Q-3 | O | — | 6-CH₃ | H | — | CH₃ | CH₃ | CH | |
| Q-3 | O | — | 5-OCH₃ | H | — | CH₃ | CH₃ | CH | |
| Q-3 | O | — | 6-OCF₂H | H | — | CH₃ | CH₃ | CH | |
| Q-3 | O | — | 5-CF₃ | H | — | CH₃ | CH₃ | CH | |
| Q-3 | O | — | 6-CH₂OCH₃ | H | — | CH₃ | CH₃ | CH | |
| Q-3 | O | — | 5-CH₂SCH₃ | H | — | CH₃ | CH₃ | CH | |
| Q-3 | N | — | H | H | CH₃ | CH₃ | CH₃ | CH | |
| Q-3 | N | — | H | CH₃ | H | CH₃ | CH₃ | CH | |
| Q-3 | N | — | H | H | H | CH₃ | CH₃ | CH | |
| Q-3 | N | — | 5-F | H | H | CH₃ | CH₃ | CH | |
| Q-3 | N | — | 6-Cl | H | H | CH₃ | CH₃ | CH | |
| Q-3 | N | — | 5-Br | H | H | CH₃ | CH₃ | CH | |
| Q-3 | N | — | 6-CH₃ | H | H | CH₃ | CH₃ | CH | |
| Q-3 | N | — | 5-OCH₃ | H | H | CH₃ | CH₃ | CH | |
| Q-3 | N | — | 6-OCF₂H | H | H | CH₃ | CH₃ | CH | |
| Q-3 | N | — | 5-CF₃ | H | H | CH₃ | CH₃ | CH | |
| Q-3 | N | — | 6-CH₂OCH₃ | H | H | CH₃ | CH₃ | CH | |
| Q-3 | N | — | 5-CH₂SCH₃ | H | H | CH₃ | CH₃ | CH | |
| Q-4 | S | — | H | CH₃ | — | CH₃ | CH₃ | CH | |
| Q-4 | S | — | H | H | — | CH₃ | CH₃ | CH | |
| Q-4 | S | — | 5-F | H | — | CH₃ | CH₃ | CH | |
| Q-4 | S | — | 6-Cl | H | — | CH₃ | CH₃ | CH | |
| Q-4 | S | — | 5-Br | H | — | CH₃ | CH₃ | CH | |
| Q-4 | S | — | 6-CH₃ | H | — | CH₃ | CH₃ | CH | |
| Q-4 | S | — | 5-OCH₃ | H | — | CH₃ | CH₃ | CH | |
| Q-4 | S | — | 6-OCF₂H | H | — | CH₃ | CH₃ | CH | |
| Q-4 | S | — | 5-CF₃ | H | — | CH₃ | CH₃ | CH | |
| Q-4 | S | — | 6-CH₂OCH₃ | H | — | CH₃ | CH₃ | CH | |
| Q-4 | S | — | 5-CH₂SCH₃ | H | — | CH₃ | CH₃ | CH | |
| Q-4 | O | — | H | CH₃ | — | CH₃ | CH₃ | CH | |
| Q-4 | O | — | H | H | — | CH₃ | CH₃ | CH | |
| Q-4 | O | — | 5-F | H | — | CH₃ | CH₃ | CH | |
| Q-4 | O | — | 6-Cl | H | — | CH₃ | CH₃ | CH | |
| Q-4 | O | — | 5-Br | H | — | CH₃ | CH₃ | CH | |
| Q-4 | O | — | 6-CH₃ | H | — | CH₃ | CH₃ | CH | |
| Q-4 | O | — | 5-OCH₃ | H | — | CH₃ | CH₃ | CH | |
| Q-4 | O | — | 6-OCF₂H | H | — | CH₃ | CH₃ | CH | |
| Q-4 | O | — | 5-CF₃ | H | — | CH₃ | CH₃ | CH | |
| Q-4 | O | — | 6-CH₂OCH₃ | H | — | CH₃ | CH₃ | CH | |
| Q-4 | O | — | 5-CH₂SCH₃ | H | — | CH₃ | CH₃ | CH | |
| Q-4 | N | — | H | H | CH₃ | CH₃ | CH₃ | CH | |
| Q-4 | N | — | H | CH₃ | H | CH₃ | CH₃ | CH | |
| Q-4 | N | — | H | H | H | CH₃ | CH₃ | CH | |
| Q-4 | N | — | 5-F | H | H | CH₃ | CH₃ | CH | |
| Q-4 | N | — | 6-Cl | H | H | CH₃ | CH₃ | CH | |
| Q-4 | N | — | 5-Br | H | H | CH₃ | CH₃ | CH | |
| Q-4 | N | — | 6-CH₃ | H | H | CH₃ | CH₃ | CH | |
| Q-4 | N | — | 5-OCH₃ | H | H | CH₃ | CH₃ | CH | |
| Q-4 | N | — | 6-OCF₂H | H | H | CH₃ | CH₃ | CH | |
| Q-4 | N | — | 5-CF₃ | H | H | CH₃ | CH₃ | CH | |
| Q-4 | N | — | 6-CH₂OCH₃ | H | H | CH₃ | CH₃ | CH | |

TABLE 8-continued

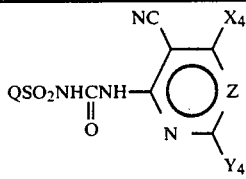

| Q | W | R | $R_1$ | $R_2$ | $R_3$ | $X_4$ | $Y_4$ | Z | m.p. (°C.) |
|---|---|---|---|---|---|---|---|---|---|
| Q-4 | N | — | 5-$CH_2SCH_3$ | H | H | $CH_3$ | $CH_3$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Active Ingredient | Percent by Weight | |
|---|---|---|---|
| | | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspension | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc., Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96;

J. D. Fryer and S. A. Evans, "Weed Control Handbook", 5th Ed., Blackwell Scientific Publications, Oxford, 1968, pp. 101–103;

J. B. Buchanan, U.S. Pat. No. 3,576,834, Apr. 27, 1971, Col. 5, line 36 through Col. 7, line 70 and Examples 1–4, 17, 106, and 123–140;

R. R. Shaffer, U.S. Pat. No. 3,560,616, Feb. 2, 1971, Col. 3, line 48 through Col. 7, line 26 and Examples 3–9 and 11–18; and E. Somers, "Formulation", Chapter 6 in Torgeson, "Fungicides", Vol. I, Academic Press, New York, 1967.

In the following examples, all parts are by weight unless otherwise indicated.

EXAMPLE 11

Wettable Powder

| | |
|---|---|
| N—[(4-methoxy-6-methylpyrimidin-2-yl)aminocarbonyl]-2-methyl-4-benzothiazolesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended and hammermilled.

EXAMPLE 12

High Strength Concentrate

| | |
|---|---|
| N—[(4-methoxy-6-methylpyrimidin-2-yl)aminocarbonyl]-2-methyl-4-benzothiazolesulfonamide | 95.% |
| silica aerogel | 0.5% |
| synthetic amorphous fine silica | 4.5% |

The ingredients are blended and ground in a hammer mill to produce a high strength concentrate essentially all passing a U.S.S. No. 50 screen (0.3 mm openings). This material may then be formulated in a variety of ways.

EXAMPLE 13

Dust

| | |
|---|---|
| wettable powder of Example 11 | 10% |
| pyrophyllite (powder) | 90% |

The wettable powder and the pyrophyllite diluent are thoroughly blended and then packaged. The product is suitable for use as a dust.

EXAMPLE 14

Granule

| | |
|---|---|
| Wettable Powder of Example 11 | 80% |
| sugar | 20% |

The ingredients are blended in a rotating or fluid bed mixer and water sprayed on to accomplish granulation. When most of the material has reached the desired range of 1.0 to 0.42 mm (U.S.S. #18 to 40 sieves), the granules are removed, dried, and screened. Oversize material is crushed to produce additional material in the desired range. These granules contain 64% active ingredient.

EXAMPLE 15

Solution

| | |
|---|---|
| N—[(4-methoxy-6-methylpyrimidin-2-yl)aminocarbonyl]-2-methyl-4-benzothiazolesulfonamide | 30% |
| dimethylformamide | 70% |

The ingredients are combined and stirred to produce a solution, which can be used for low volume applications.

EXAMPLE 16

Emulsifiable Concentrate

| | |
|---|---|
| N—[(4-methoxy-6-methylpyrimidin-2-yl)aminocarbonyl]-2-methyl-4-benzothiazolesulfonamide, | 10% |
| blend of oil soluble sulfonates and polyoxyethylene ethers | 4% |
| xylene | 86% |

The ingredients are combined and stirred until the active is dissolved. A fine screen filter is included in packaging operation to insure the absence of any extraneous undissolved material in the product.

EXAMPLE 17

Aqueous Suspension

| | |
|---|---|
| N—[(4-methoxy-6-methylpyrimidin-2-yl)aminocarbonyl]-2-methyl-4-benzothiazolesulfonamide | 50.1% |
| dodecylphenol polyethylene glycol ether | 0.5% |
| crude calcium ligninsulfonate | 5.0% |
| xanthan gum thickener | 0.2% |
| paraformaldehyde | 0.2% |
| water | 44% |

The ingredients are ground together in a sand, ball or colloid mill to produce particles essentially all under 5 microns in size.

Utility

Test results indicate that the compounds of the present invention are highly active preemergent or postemergent herbicides or plant growth regulants. Many of them have utility for broad-spectrum pre- and/or postemergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice, wheat, and barley. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhose tests. The test procedures and results follow.

| Compounds | |
|---|---|
| Compound 1 | 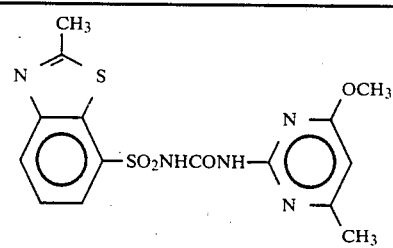 |

-continued

| Compounds | |
|---|---|
| Compound 2 | 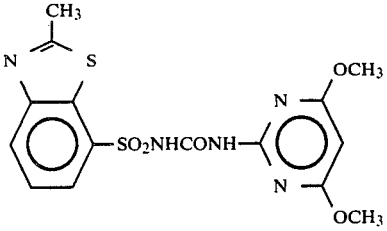 |
| Compound 3 | 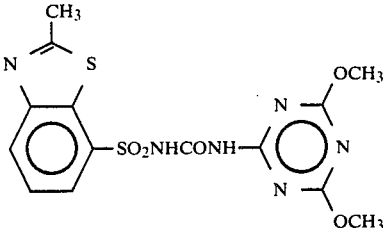 |
| Compound 4 | 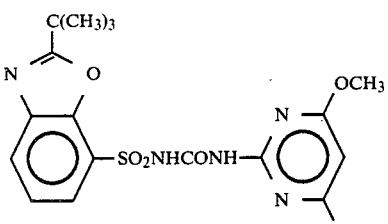 |
| Compound 5 | 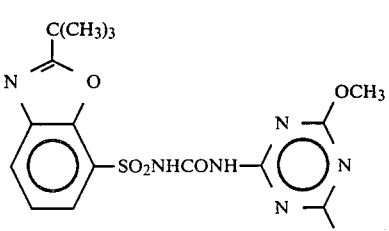 |
| Compound 6 | 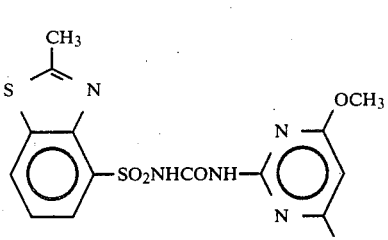 |
| Compound 7 | 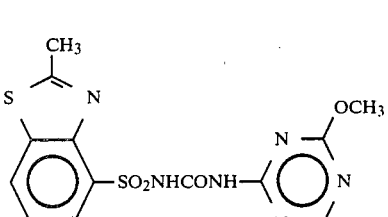 |

-continued

| Compounds | |
|---|---|
| Compound 8 | 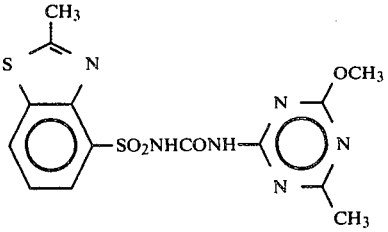 |
| Compound 9 | 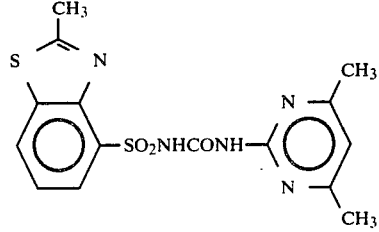 |
| Compound 10 | 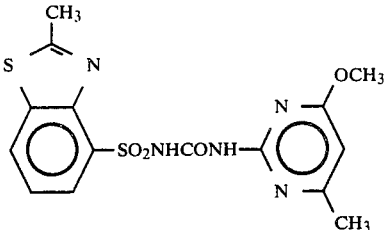 |

Test A

Seeds of crabgrass (Digitaria sp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugarbeet, cotton, rice, wheat and purple nutsedge (Cyperus rotundus) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

TABLE A

| | Compound 1 | | Compound 2 | |
|---|---|---|---|---|
| Rate kg/ha | .4 | .05 | .4 | .05 |
| POSTEMERGENCE | | | | |

TABLE A-continued

| | | | | |
|---|---|---|---|---|
| Morningglory | 3C,9G | 1C,3G | 1C | 2C |
| Cocklebur | 5C,9G | 5C,9G | 6C,9G | 4C,9G |
| Sicklepod | 4C,9G | 3C,3H | 3C,9H | 3C,7H |
| Nutsedge | 10C | 3C,6G | 2C,9G | 5G |
| Crabgrass | 1C,5G | 0 | 2C,3G | 0 |
| Barnyardgrass | 2C,6G | 0 | 0 | 0 |
| Wild Oats | 2G | 0 | 0 | 0 |
| Wheat | 2G | 0 | 0 | 0 |
| Corn | 1C,3G | 0 | 2G | 0 |
| Soybean | 4C,9G | 3C,8G | 3C,9G | 3C,8G |
| Rice | 2C,8G | 0 | 3C,5G | 0 |
| Sorghum | 3C,9H | 1C | 3C,6G | 0 |
| Sugar beet | 9C | 9C | 10C | 9C |
| Cotton | 4C,9G | 3C,7G | 3C,4H,8G | 3C,3H,8G |
| Bush bean | 1C,1H | 0 | 1C | 0 |
| PREEMERGENCE | | | | |
| Morningglory | 9G | 0 | 9G | 2H,2C |
| Cocklebur | — | 9G | 9H | 9H |
| Sicklepod | 5C,9G | 3C,5G | 2C | 0 |
| Nutsedge | 2C,9G | 0 | 2C,9G | 2G |
| Crabgrass | 2C | 1C | 3G | 1C |
| Barnyardgrass | 4C,8H | 3C | 3C,6G | 2C |
| Wild Oats | 2C,8G | 0 | 8G | 2C |
| Wheat | 5G | 0 | 3G | 0 |
| Corn | 2C,8H | 1C | 1C,7G | 2G |
| Soybean | 2C,8H | 3C,3G | 2C,2H | 1C |
| Rice | 3C,7G | 3C,3G | 2C,8H | 2G |
| Sorghum | 2C,8H | 3G | 3C,7G | 1C |
| Sugar beet | 5C,9G | 2C,8G | 9C | 8G |
| Cotton | — | — | — | — |

| | Compound 3 | Cmpd. 4 | Cmpd. 5 |
|---|---|---|---|
| Rate kg/ha | .4 | .05 | .4 | .4 |
| POSTEMERGENCE | | | | |
| Morningglory | 2C,3H | 0 | 2C,7G | 2C,9H |
| Cocklebur | 2C,9G | 1H | 5C,9G | 3C,5G |
| Sicklepod | 2C | 0 | 2C,2H | 2C |
| Nutsedge | 0 | 0 | 2C,4G | 0 |
| Crabgrass | 0 | 0 | 2G | 2G |
| Barnyardgrass | 0 | 0 | 1H | 0 |
| Wild Oats | 0 | 0 | 0 | 0 |
| Wheat | 0 | 0 | 0 | 0 |
| Corn | 1C | 0 | 1C,2H | 0 |
| Soybean | 3C,8G,5X | 2C,3H | 2C,7H | 1C,2H |
| Rice | 9G | 1C,8G | 3C,5G | 2G |
| Sorghum | 2C,5H | 2C,3G | 4G | 0 |
| Sugar beet | 9C | 4C,8G | 3C,7G | 4C,8H |
| Cotton | 3C,3H,7G | 2C,2H | 2C,3H | 0 |
| Bush bean | 3C,3H,6Y | 1C | 1C | — |
| PREEMERGENCE | | | | |
| Morningglory | 3C,6H | 0 | 2C | 2C,5H |
| Cocklebur | 1C,3H | 0 | — | 1C |
| Sicklepod | 3C | 0 | 0 | — |
| Nutsedge | 0 | 0 | 0 | 0 |
| Crabgrass | 2G | 0 | 1C | 5G |
| Barnyardgrass | 2C | 1C | 3C | 1C |
| Wild Oats | 2C | 0 | 1C | 2C |
| Wheat | 3G | 0 | 0 | 0 |
| Corn | 2C,7G | 1C | 2C,5G | 2C |
| Soybean | 3C,4H | 1C | 1H | 2C |
| Rice | 3C,8H | 3C | 4G | 2C |
| Sorghum | 3C,9H | 2C,5G | 2C,6G | 4G |
| Sugar beet | 6C,9G | 1C,5H | 8G | 2C,5G |
| Cotton | — | — | — | 1C |

| | Cmpd. 6 | Cmpd. 7 | Cmpd. 8 | Cmpd. 9 | Cmpd. 10 |
|---|---|---|---|---|---|
| Rate kg/ha | .05 | .05 | .05 | .05 | .05 |
| POSTEMERGENCE | | | | | |
| Morningglory | 2C,7G | 2C,8G | 8H | 1C | 5C,9G |
| Cocklebur | 10C | 10C | 4C,9G | 2G | 9C |
| Sicklepod | 5C,9G | 9C | 5C,9G | 1C | 4C,8G |
| Nutsedge | 9C | 2C,3G | 0 | 0 | 2C,9G |
| Crabgrass | 5G | 0 | 0 | 0 | 2C,3G |
| Barnyardgrass | 3C,9H | 3H | 2H | 0 | 4C,8H |
| Wild Oats | 2C,5G | 0 | 0 | 0 | 0 |
| Wheat | 6G | 0 | 0 | 0 | 0 |
| Corn | 9G | 9H | 4C,8H | 0 | 2C,9G |
| Soybean | 5C,9G | 5C,9G | 5C,9G | 0 | 4C,8G |
| Rice | 4C,9G | 9C | 9C | 0 | 5C,9G |
| Sorghum | 4C,9H | 5C,9H | 5C,9H | 0 | 4C,9H |

TABLE A-continued

| | | | | |
|---|---|---|---|---|
| Sugar beet | 10C | 9C | 9C | 3G | 5C,9G |
| Cotton | 9C | 5C,9G | 4C,8G | 0 | 3C,9G |
| Bush bean | — | — | — | — | — |
| PREEMERGENCE | | | | | |
| Morningglory | 8G | 6G | 5G | 2C | 9G |
| Cocklebur | 8H | 6H | 7G | 0 | 8H |
| Sicklepod | 2C,9G | 6G | 7G | 0 | 2C,8G |
| Nutsedge | 8G | 0 | 0 | 0 | 8G |
| Crabgrass | 2C,4G | 0 | 2C | 0 | 2C,6G |
| Barnyardgrass | 3C,9H | 3C,4G | 1C | 0 | 5C,9H |
| Wild Oats | 2C,7G | 2C | 2G | 0 | 5C,9G |
| Wheat | 7G | 2C | 4G | 0 | 2C,8G |
| Corn | 2C,9G | 2C,8G | 2C,8H | 0 | 4C,9G |
| Soybean | 2C,7H | 3C,5H | 3C,6H | 1C | 3C,7G |
| Rice | 10E | 4C,8H | 9H | 0 | 10E |
| Sorghum | 5C,9H | 4C,8H | 3C,8H | 0 | 5C,9H |
| Sugar beet | 8G | 5C,9G | 9C | 3H | 9C |
| Cotton | 9G | 8G | 7G | 1C | 9G |

Test B

Two 25 cm diameter plastic containers were lined with plastic bags and filled with limed Woodstown sandy loam. A 25 cm diameter Lucite ® planting template was used to slightly compress the soil within each container and to provide indentations for the planting of nine test species. Seeds of the following species were placed in one container: cocklebur (*Xanthium pensylvanicum*), velvetleaf (*Abutilon theophrasti*), sugar beets (*Beta vulgaris*), sicklepod (*Cassia obtusifolia*), morningglory (*Ipomoea* spp.), teaweed (*Sida spinosa*), cotton (*Gossypium hirsutum*), jimsonweed (*Datura stramonium*) and soybean (*Glycine max.*). The second pot was planted with seeds or tubers of the following species: purple nutsedge (*Cyperus rotundus*), rice (*Oryza sativa*), giant foxtail (*Setaria faberii*), crabgrass (*Digitaria sanguinalis*), johnsongrass (*Sorghum halepense*), wild oats (*Avena fatua*), wheat (*Triticum aestivum*), barnyardgrass (*Echinochloa crusgalli*), and corn (*Zea mays*). Both containers were then topped with an approximately 1 cm layer of soil to cover the seeds. These two containers were then sprayed preemergence with several test compounds from within the scope of the invention. Following treatment, the plantings received approximately 1 cm of simulated rainfall in a period of 150 minutes.

Approximately twenty-eight days after treatment, the plants were visually rated for response to the chemical treatments utilizing the rating system previously described for Test A. Results are presented in Table B.

TABLE B

| | Compound 2 | | | | |
|---|---|---|---|---|---|
| Rate kg/ha | 1/16 | 1/1024 | 1/256 | 1/4 | 1/64 |
| Rice | 10C | 7G | 9G | 10C | 10C |
| Barnyardgrass | 9G | 2G | 5G | 9G | 8G |
| Wheat | 3G | 0 | 0 | 8G | 0 |
| Wild Oats | 9G | 3G | 6G | 9G | 8G |
| Crabgrass | 7G | 0 | 3G | 9G | 4G |
| Johnsongrass | 9G | 2G | 2G | 9G | 8G |
| Giant Foxtail | 8G | 2G | 2G | 9G | 7G |
| Corn | 10C | 0 | 6G | 10C | 9G |
| Cocklebur | 9G | 2G | 4G | 9G | 7G |
| Nutsedge | 9G | 0 | 4G | 10C | 9G |
| Cotton | 9G | 0 | 4G | 9G | 8G |
| Morningglory | 9G | 0 | 5G | 9G | 8G |
| Sicklepod | 9G | 0 | 3G | 9G | 8G |
| Teaweed | 9G | 0 | 3G | 9G | 7G |
| Velvetleaf | 9G | 4G | 4G | 9G | 7G |
| Jimsonweed | 9G | 0 | 2G | 9G | 8G |
| Soybean | 9G | 0 | 2G | 9G | 7G |
| Sugar beet | 10C | 7G | 9G | 10C | 10C |

Test C

In Test C, plastic pots filled with Fallsington sandy loam were planted to soybeans, cotton, corn, rice, wheat, sorghum, velvetleaf (*Abutilon theophrasti*), sesbania (*Sesbania exaltata*), cassia (*Cassia tora*), morningglory (*Ipomoea* spp.), jimsonweed (*Datura stramonium*), cocklebur (*Xanthium pensylvanicum*), crabgrass (*Digitaria* spp.), nutsedge (*Cyperus rotundus*), johnsongrass (*Sorghum halepense*), barnyardgrass (*Echinochloa crusgalli*), giant foxtail (*Setaria faberii*) and wild oats (*Avena fatua*). Eighteen days after planting, the young plants and the soil around them were sprayed overall with the test chemical dissolved in a non-phytotoxic solvent. Fourteen days after treatment, all species were compared to untreated controls and visually rated for response to treatment utilizing the rating system previously described for Test A. The ratings for the compound tested by this procedure are presented in the Table C.

TABLE C

| | Compound 1 | | | |
|---|---|---|---|---|
| Rate kg/ha | 1/64 | 1/4 | 1/256 | 1/16 |
| Soybean | 4C | 9C | 0 | 9C |
| Corn | 1C | 1C | 0 | 1C |
| Cotton | 0 | 3C | 0 | 2C |
| Rice | 0 | 4G | 0 | 0 |
| Wheat | 0 | 0 | 0 | 0 |
| Velvetleaf | 0 | 10C | 0 | 7G |
| Sesbania | 5C | 9G | 0 | 9G |
| Sicklepod | 1C | 7G | 0 | 3C |
| Morningglory | 0 | 3G | 0 | 0 |
| Jimsonweed | 2G | 4G | 2G | 0 |
| Cocklebur | 7G | 10C | — | 10C |
| Sugar beet | 9G | 8G | 5G | 8G |
| Crabgrass | 0 | 0 | 0 | 0 |
| Barnyardgrass | 0 | 0 | 0 | 0 |
| Giant Foxtail | 0 | 0 | 0 | 0 |
| Wild Oats | 0 | 0 | 0 | 0 |
| Sorghum | 0 | 5G | 0 | 2C |
| Nutsedge | 0 | 1C | 0 | 0 |
| Johnsongrass | 0 | 0 | 0 | 0 |

| | Compound 2 | |
|---|---|---|
| Rate kg/ha | 1/64 | 1/4 |
| Soybean | 9G | 9G |
| Corn | 1C | 2C |
| Cotton | 8G | 7G |
| Rice | 0 | 0 |
| Wheat | 0 | 0 |
| Velvetleaf | 8G | 8G |
| Sesbania | 9G | 8G |
| Sicklepod | 3C | 4G |
| Morningglory | 6G | 3G |
| Jimsonweed | — | 3G |
| Cocklebur | 10G | 10G |
| Sugar beet | 10C | 10C |
| Crabgrass | 0 | 3G |
| Barnyardgrass | 0 | 0 |
| Giant Foxtail | 0 | 2G |
| Wild Oats | 0 | 1G |
| Sorghum | — | — |
| Nutsedge | 6G | 5G |
| Johnsongrass | 0 | 0 |

Test D

Sixteen-cm diameter glazed clay Wagner pots, equipped with a stoppered drain opening near the bottom of the side wall, were partially filled with Woodstown sandy loam. About 1500 ml of water were added to each pot to bring the water level to a point 3 cm above the soil surface. Also, a number of barnyardgrass (*Echinochloa crusgalli*) seeds were added to each pot. At the same time, seedlings or tubers of the following species were transplanted into the muddy soil: water plantain (*Alisma trivale*). Scirpus (*Scirpus mucranatus*), and Cyperus (*Cyperus difformis*). The weed species selected for this test are of economic importance in major rice-growing areas. The chemial treatments were applied as described below in the crop response portion of the test within hours after transplanting of two additional species: water chestnut (*Eleocharis* spp.) and arrowhead (*Sagittaria latifolia*). Shortly after treatment, the drain hole was opened to drop the water level by two cm. Water was then added to restore the water level to its original height. The following day the draining and refilling process was repeated. The pots were then maintained in the greenhouse. Rates of application and plant response ratings made 21 days after treatment are summarized in Table D.

In the crop response portion, twelve-cm diameter waxed paper cups were partially filled with Woodstown sandy loam. About 750 ml of water was added to each cup to bring the water level to a point 3 cm above the soil surface. Japonica rice seed was added to the pots, the seeds coming to rest on the soil surface (direct seeded rice). In addition, Japonica rice seedlings in the 2.5 leaf stage were transplanted into the same pots. Five days after seeding and transplanting compound number 1, dissolved in a small volume of acetone, was injected into the water of the simulated rice paddy. The rates of application and the crop response ratings made 10 days after treatment are shown in Table D.

TABLE D

| Rate gm/ha | 8 | 2 |
|---|---|---|
| Barnyardgrass | 60 | 30 |
| Water Chestnut | 20 | 0 |
| Arrowhead | 100 | 80 |
| Scirpus | 70 | 100 |
| Cyperus | 100 | 100 |
| Water plantain | 90 | 0 |

| | Crop Response | |
|---|---|---|
| gm/ha | Transplanting | Direct Seeded |
| 1000 | 50 | 100 |
| 0250 | 20 | 90 |
| 0063 | 40 | 90 |
| 0016 | 20 | 50 |
| 0004 | 20 | 0 |
| 0001 | 20 | 0 |
| .25 | 10 | 0 |

What is claimed is:

1. A compound of the formula

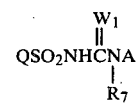

wherein

Q is

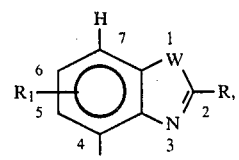

-continued

Q-2

Q-3

Q-4

$W_1$ is O or S;
$R_7$ is H or $CH_3$;
R is H, $C_1$–$C_4$ alkyl optionally substituted with 0–3 halogen atoms selected from 1–3 F, 1–2 Cl or 1 Br, $C_1$–$C_4$ alkylthio, $C_1$–$C_4$ alkoxy, $CH_2OCH_3$, $CH_2CH_2OCH_3$ or $CH_2SCH_3$;
$R_1$ is H, halogen, $C_1$–$C_3$ alkyl, $C_1$–$C_3$ haloalkyl, nitro, $C_1$–$C_3$ alkoxy, di($C_1$–$C_2$)alkylaminosulfamoyl, $C_1$–$C_3$ alkylthio, $C_1$–$C_3$ haloalkoxy, $C_1$–$C_3$ haloalkylthio, cyano, $C_1$–$C_3$ alkylsulfinyl, $C_1$–$C_3$ alkylsulfonyl, $C_2$–$C_3$ alkoxycarbonyl, $CH_2OCH_3$, $CH_2SCH_3$ or $CH_2CN$;
$R_2$ is H or $CH_3$;
W is O, S or $NR_3$;
$R_3$ is H or $CH_3$;
A is

A-1

A-2

A-3

-continued

A-4

A-7

X is H, $C_1$–$C_3$ alkyl, $C_1$–$C_3$ alkoxy, $C_1$–$C_3$ haloalkoxy, $C_1$–$C_3$ haloalkyl, $C_1$–$C_3$ haloalkylthio, $C_1$–$C_3$ alkylthio, halogen, $C_2$–$C_3$ alkoxyalkyl, $C_2$–$C_3$ alkoxyalkoxy, amino, $C_1$–$C_3$ alkylamino or di($C_1$–$C_3$)alkylamino;
Y is H, $C_1$–$C_3$ alkyl, $C_1$–$C_3$ alkoxy, $C_1$–$C_3$ haloalkoxy, $C_1$–$C_3$ haloalkylthio, $C_1$–$C_3$ alkylthio, halogen, $C_2$–$C_3$ alkoxyalkyl, $C_2$–$C_3$ alkoxyalkoxy, amino, $C_1$–$C_3$ alkylamino, di($C_1$–$C_3$)alkylamino, $C_3$ alkenyloxy, $C_3$ alkynyloxy, $C_2$–$C_3$ alkynyl, $C_2$–$C_3$ alkylthioalkyl, $C_2$–$C_3$ alkylsulfinylalkyl, $C_2$–$C_3$ alkylsulfonylalkyl, $C_1$–$C_3$ haloalkyl, cyclopropyl, $C(O)R_4$, $$-\underset{R_4}{\overset{L_1R_5}{\underset{|}{C}}}\underset{L_2R_6}{\overset{}{\text{,}}} \quad -\underset{R_4}{\overset{L_1}{\underset{|}{C}}}\underset{L_2}{\overset{}{(CH_2)_m}}, \quad \underset{L_2}{\overset{L_1}{CR_4}}\underset{}{\overset{CH_3}{\diagdown}}$$

or $N(OCH_3)CH_3$;
m is 2 or 3;
$L_1$ and $L_2$ are independently O or S;
$R_4$ is H or $CH_3$;
$R_5$ and $R_6$ are independently $C_1$–$C_2$ alkyl;
Z is CH;
$Y_1$ is O or $CH_2$;
$X_1$ is $CH_3$, $OCH_3$, $OC_2H_5$ or $OCF_2H$;
$Y_2$ is H or $CH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that
(a) when $W_1$ is S, then $R_7$ is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or (structure)

b when X is F, Cl, Br or I, then Y is $OCH_3$, $OC_2H_5$, $OCF_2H$, $NH_2$, $NHCH_3$, $N(OCH_3)CH_3$ or $N(CH_3)_2$;
c when $R_1$ is di($C_1$–$C_2$)alkylaminosulfamoyl or $C_2$–$C_3$ alkoxycarbonyl, then Q is Q-1 and $R_1$ is in the 5-position or Q is Q-2 and $R_1$ is in the 6-position; and
d when the total number of carbon atoms of X and Y is greater than four, then the number of carbon atoms of R is less than or equal to two, and the number of carbon atoms of $R_1$ is less than or equal to two.

2. The compounds of claim 1 wherein $W_1$ is O, $R_7$ is H, X is $CH_3$, $OCH_3$, $OC_2H_5$, halogen, $OCF_2H$, $CH_2F$, $OCH_2CH_2F$, $OCH_2CHF_2$, $OCH_2CF_3$ or $CF_3$, and Y is H, $CH_3$, $OCH_3$, $OC_2H_5$, $CH_2OCH_3$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $C\equiv CH$, $C\equiv CCH_3$, $CH_2OC_2H_5$, $OCH_2CH_2OCH_3$, $CH_2SCH_3$, $C(O)R_4$,

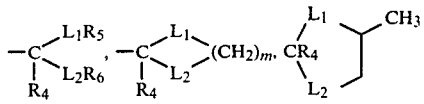

$OCF_2H$, $SCF_2H$ or cyclopropyl.

3. The compounds of claim 2 where $R_1$ is H, F, Cl, Br, $CH_3$, $OCH_3$, $OCF_2H$, $CF_3$, $CH_2OCH_3$ or $CH_2SCH_3$, R is H or $C_1$–$C_2$ alkyl, and Q is Q-1 or Q-2.

4. The compounds of claim 3 where A is A-1, X is $CH_3$, $OCH_3$, Cl, Br or $OCF_2H$, and Y is $CH_3$, $OCH_3$, $CH_2OCH_3$, $NHCH_3$, $C_2H_5$, $CH(OCH_3)_2$, cyclopropyl, $C\equiv CH$ or $C\equiv CCH_3$.

5. The compounds of claim 4 where Q is Q-1 and $R_1$ is H.

6. The compounds of claim 4 where Q is Q-2 and $R_1$ is H.

7. The compounds of claim 5 where W is O.
8. The compounds of claim 5 where W is S.
9. The compounds of claim 5 where W is $NR_3$.
10. The compounds of claim 6 where W is O.
11. The compounds of claim 6 where W is S.
12. The compounds of claim 6 where W is $NR_3$.
13. The compound of claim 1 that is N-[(4,6-dimethoxypyrimidin-2-yl)aminocarbonyl]-2-methylbenzothiazole-4-sulfonamide.

14. An agriculturally suitable composition for controlling the growth of undesired vegetation comprising an effective amount of a compound of claim 1 and at least one of the following: surfactant, solid or liquid diluent.

15. An agriculturally suitable composition for controlling the growth of undesired vegetation comprising an effective amount of a compound of claim 2 and at least one of the following: surfactant, solid or liquid diluent.

16. An agriculturally suitable composition for controlling the growth of undesired vegetation comprising an effective amount of a compound of claim 3 and at least one of the following: surfactant, solid or liquid diluent.

17. An agriculturally suitable composition for controlling the growth of undesired vegetation comprising an effective amount of a compound of claim 4 and at least one of the following: surfactant, solid or liquid diluent.

18. An agriculturally suitable composition for controlling the growth of undesired vegetation comprising an effective amount of a compound of claim 5 and at least one of the following: surfactant, solid or liquid diluent.

19. An agriculturally suitable composition for controlling the growth of undesired vegetation comprising an effective amount of a compound of claim 6 and at least one of the following: surfactant, solid or liquid diluent.

20. An agriculturally suitable composition for controlling the growth of undesired vegetation comprising an effective amount of a compound of claim 7 and at least one of the following: surfactant, solid or liquid diluent.

21. An agriculturally suitable composition for controlling the growth of undesired vegetation comprising an effective amount of a compound of claim 8 and at least one of the following: surfactant, solid or liquid diluent.

22. An agriculturally suitable composition for controlling the growth of undesired vegetation comprising an effective amount of a compound of claim 13 and at least one of the following: surfactant, solid or liquid diluent.

23. A method for controlling the growth of undesired vegetation which comprises applying to the locus to be protected an effective amount of a compound of claim 1.

24. A method for controlling the growth of undesired vegetation which comprises applying to the locus to be protected an effective amount of a compound of claim 2.

25. A method for controlling the growth of undesired vegetation which comprises applying to the locus to be protected an effective amount of a compound of claim 3.

26. A method for controlling the growth of undesired vegetation which comprises applying to the locus to be protected an effective amount of a compound of claim 4.

27. A method for controlling the growth of undesired vegetation which comprises applying to the locus to be protected an effective amount of a compound of claim 5.

28. A method for controlling the growth of undesired vegetation which comprises applying to the locus to be protected an effective amount of a compound of claim 6.

29. A method for controlling the growth of undesired vegetation which comprises applying to the locus to be protected an effective amount of a compound of claim 7.

30. A method for controlling the growth of undesired vegetation which comprises applying to the locus to be protected an effective amount of a compound of claim 8.

31. A method for controlling the growth of undesired vegetation which comprises applying to the locus to be protected an effective amount of a compound of claim 13.

* * * * *